(12) United States Patent
Appleton et al.

(10) Patent No.: US 8,318,163 B2
(45) Date of Patent: Nov. 27, 2012

(54) ANTI-PAN NEUROPILIN ANTIBODY AND BINDING FRAGMENTS THEREOF

(75) Inventors: Brent A. Appleton, San Francisco, CA (US); Christian Wiesmann, Bottmingen (CH); Yan Wu, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/598,625

(22) PCT Filed: May 17, 2007

(86) PCT No.: PCT/US2007/069185
§ 371 (c)(1),
(2), (4) Date: Feb. 25, 2010

(87) PCT Pub. No.: WO2008/143666
PCT Pub. Date: Nov. 27, 2008

(65) Prior Publication Data
US 2010/0150919 A1    Jun. 17, 2010

(51) Int. Cl.
*A61K 39/00* (2006.01)
*A61K 39/395* (2006.01)
*C07K 16/00* (2006.01)
(52) U.S. Cl. ............... 424/133.1; 424/172.1; 530/389.1
(58) Field of Classification Search ........................ None
See application file for complete search history.

(56) References Cited

U.S. PATENT DOCUMENTS

| | | | |
|---|---|---|---|
| 4,816,567 A | 3/1989 | Cabilly | |
| 5,427,908 A | 6/1995 | Dower | |
| 5,432,018 A | 7/1995 | Dower | |
| 5,498,530 A | 3/1996 | Schatz | |
| 5,580,717 A | 12/1996 | Dower | |
| 5,580,723 A | 12/1996 | Wells | |
| 5,658,727 A | 8/1997 | Barbas | |
| 5,723,286 A | 3/1998 | Dower | |
| 5,733,743 A | 3/1998 | Johnson | |
| 5,750,373 A | 5/1998 | Garrard | |
| 5,837,242 A | 11/1998 | Holliger | |
| 5,969,108 A | 10/1999 | McCafferty | |
| 6,172,197 B1 | 1/2001 | McCafferty | |
| 7,691,977 B2 * | 4/2010 | Fuh et al. ................... | 530/387.1 |

FOREIGN PATENT DOCUMENTS

| | | |
|---|---|---|
| EP | 0368684 B2 | 9/2004 |
| EP | 0817648 B1 | 12/2004 |
| GB | 2268744 | 1/1994 |
| WO | WO 92/22653 | 12/1992 |
| WO | WO 94/04679 | 3/1994 |
| WO | WO 94/10202 | 5/1994 |
| WO | WO 98/45332 A2 | 4/1997 |

OTHER PUBLICATIONS

Van Kooi et al. "Structural basis for ligand and heparin binding to neuropilin B domains", PNAS, Apr. 3, 2007 (epub), 104(15): 6152-6157.*

Adamis, et al., "Inhibition of Vacular endothelial growth factor prevents retinal ischemia-associated iris neovascularization in a nonhuman primate", Arch. Ophthalmol., 114: 66-71, (1996).
Aiello, et al., "Suppression of retinal neovascularization in vivo by inhibition of vascular endothelial growth factor (VEGF) using soluble VEGF-receptor chimeric proteins", PNAS, vol. 92, pp. 10457-10461, (1995).
Aiello, et al., "Vascular endothellial growth factor in ocular fluid of patients with diabetic retinopathy and other retinal disorders", The New England Journal, 331: 1480-1487, (1994).
Baca, et al., "Antibody humanization using monovalent phage display", The journal of Biological Chemistry, vol. 272, No. 16, pp. 10678-10684, (1997).
Barbas, et al., "In vitro evolution of a neutralizing human antibody to human immunodeficiency virus type 1 to enhace affinity and broaden strain cross-reactivity", PNAS, vol. 91, pp. 3809-3813, (1994).
Barbas, et al., "Selection and evolution of high-affinity human anitviral antibodies", Tibtech, vol. 14, pp. 230-234, (1996).
Bass, et al., "Hormone phage: An enrichment method for variant proteins with altered binding properties", Proteins: Structure, function and genetics, 8: 309-314, (1990).
Bendig, et al., "Humanization of rodent monoclonal antibodies by CDR grafting", Methods: A companion to methods in Enzymology, 8: 83-93, (1995).
Berkman, et al., "Expression of the vascular permeability factor/vascular endothelial growth factor gene in central nervous system neoplasms", The Journal of Clinical Investigation, Inc., vol. 91, pp. 153-159, (1993).
Borgstrom, et al., "Complete inhibiton of angiogenesis and growth of microtumors by anti-vascular endothelial growth factor neutralizing antibody: Novel concepts of angiostatic therapy from intravital videomicroscopy", Cancer Research, 56: 4032-4039, (1996).
Brown, et al., "Expression of vacular permeability factor (Vascular endothelial growth factor) and its receptors in adenocarcinomas of the gastrointestinal tract", Cancer Research, 53: 4727-4735, (1993).
Brown, et al., "Expression of vascular permeability factor (Vascular endothelial growth factor) and its receptors in breast cancer", Human Pathology, vol. 26, No. 1, pp. 86-91, (1995).
D'Amore, et al., "Mechanisms of retinal and choroidal neovascularization", Investigative ophthalmology & Visual science, vol. 35, No. 12, pp. 3974-3979, (1994).
Dastgheib, et al., "Vascular endothelial growth factor (VEGF) in neovascular age-related macular degeneration", Investigative Ophthalmology & Visual Science, vol. 36, No. 4, 494-402, (1995).
Deng, et al., "Selection of antibody single-chain variable fragments with improved carbohydrate binding by phage display", The Journal of Biological of Chemistry, vol. 269, No. 13, pp. 9533-9538, (1994).
Dickson, et al., "Molecular machanisms of axon guidance", Science, vol. 298, pp. 1959-1964, (2002).
Dvorak, et al., "Vascular permeability factor/vascular endothelial growth factor, microvascular hyperpermeability and angiogenesis", American Journal of Pathology, vol. 146, No. 5, pp. 1029-1039, (1995).

(Continued)

*Primary Examiner* — Gregory S Emch
(74) *Attorney, Agent, or Firm* — Janet Martineau; Alissa H. Faris; Arnold & Porter LLP

(57) ABSTRACT

The invention provides crystal structures of neuropilin 1 (Nrp1) and neuropilin 2 (Nrp2) fragments alone and in complex with anti-neuropilin antibodies, and method for their use. The invention further provides anti-Nrp antibodies and methods for their therapeutic applications.

19 Claims, 20 Drawing Sheets

OTHER PUBLICATIONS

Ferrara, et al., "The biology of vascular endothelial growth factor", Endocrine Reviews, vol. 18, No. 1, pp. 4-25, (1997).
Folkman, "Angiogenesis in cancer, vascular, rheumatoid and other disease", Natural Medicine, vol. 1, No. 1, pp. 27-31,(1995).
Folkman, "Induction of angiogenesis during the transition from hyperplasia to neoplasia", Nature, vol. 339, pp. 58-61, (1989).
Folkman, et al., "Angiogenesis", The Journal of Biological Chemistry, vol. 267, No. 16, pp. 10931-10934, (1992).
Forsberg, et al., "Identification of framework residues in a secreted recombinant antibody fragment that control production level and localization in *Escherichia coli*", vol. 272, No. 19, pp. 12430-12436, (1997).
Fujisawa, et al., "Receptors for collapsin/semaphorins", Current Opinion in Neurobilogy, 8:587-592, (1998).
Garner, "VascularDiseases", Pathobiology of Ocular Disease, Chapter 52, pp. 1625-1710, (1994).
Gerhardt, et al., "Neuropilin-1 isrequired for endothelial tip cell guidance in the develpoing central nerveous system", Develpomental Dynamics, 231: 503-509, (2004).
Griffiths, et al., "Isolation of high affinity human antibodies directly from large synthetic repertories", The EMBO Journal, vol. 13, No. 14, pp. 3245-3260, (1994).
Gu, et al., "Neuropilin-1 conveys semaphorin and VEGF signaling during neural and cardiovascular develpoment", Developmental Cell, vol. 5, pp. 45-57, (2003).
Hanahan, "Signaling vacular morphogenesis and maintenance", Science, vol. 277, pp. 48-50, (1997).
Hawkins, et al., "Selection of phage antibodies by binding affinity", J. Mo. Biol., 226: 889-896, (1992).
Herzog, et al., "Differential expression of neuropilin-1 and neuropilin-2 in arteries and veins", Mechanisms of Development, 109: 115-119, (2001).
Hogan, et al., "Molecular mechanisms of tubulogenesis", Nature Reviews, Genetics, vol. 3, pp. 513-523, (2002).
Hoogenboom, et al., "Antibody phage display technology and its applications", Immunotechnology, 4: 1-20, (1998).
Horak, et al., "Angiogenesis, assessed by platelet/endothelial cell adhesion molecule antibodies, as indicator of node metastases and survival in breast cancer", The Lancet, vol. 340, pp. 1120-1124, (1992).
Huber, et al., "Signaling at the growth cone: Ligand-receptor complexes and the control of axon growth and guidance", Annu. Rev. Neurosci., 26: 509-563, (2003).
Jackson, et al., "In vitro antibody maturation", The Journal of Immunology, 154: 3310-3319, (1995).
Jones, et al., "Replacing the complementarity-determining regions in a human antibody with those from a mouse", Nature, vol. 321, pp. 522-525, (1986).
Kawasaki, et al., "A requirement for neuropilin-1 in embryonic vessel formation", Development, 126: 4895-4902, (1999).
Kim, et al., "Inhibition of vascular endothelial growth factor-induced angiogenesis suppresses tumour growth in vivo", Nature, vol. 362, pp. 841-844, (1993).
Klagsbrun, et al., "Regulators of angiogenesis", Annu. Rev. Physiol., 53: 217-239, (1991).
Klagsbrun, et al., "The role of neuropilin in vascular and tumor biology", Adv. Exp. Med. Biol. pp. 33-48, (2002).
Knappik, et al., "Fully synthetic human combinatorial antibody libraries (HuCAL) based on modular consensus frameworks and CDRs randomized with trinucleotides", JMB, 296: 57-86, (2000).
Lopez, et al., "Transdifferentiated retinal pigment epithelial cells are immunoreactive for vascular endothelial growth factor in surgically excised age-related macular degeneration-related choroidal neovascular membranse", Invest. Opthalmol., 37: 855-868, (1996).
Lowman, et al., "Monovalent phage display: A method for selecting variant proteins from random libraries", Methods: A companion to Methods in Enzymology, vol. 3, No. 3, pp. 205-216, (1991).
Lubarsky, et al., "Tube morphogenesis: Making and chaping biological tubes", Cell, vol. 112, pp. 19-28, (2003).
Macchiarini, et al., "Relation of neovascularisation to metastasis of non-small-cell lung cancer", Lancet, 340: 145-146, (1992).
Mattern, et al., "Association of vascular endothelial growth factor expression with intratumoral microvessel density and tumor cell proliferation in human epidermoid lung carcinoma", British Journal of Cancer, 73: 931-934,(1996).
Melnyk, et al., "Vascular endothelial growth factor promotes tumor dissemination by a mechanism distinct from its effect on primary tumor growth", Cancer Research, 56, 921-924, (1996).
Ozaki, et al., "Basic fibroblast growth factor is neither necessary nor sufficient for the development of retinal neovascularization", American Journal of Pathology, vol. 153, No. 3, pp. 757-765, (1998).
Raper, "Semaphorins and their receptors in vertebrates and invertebrates", Current opinion in neurobiology, 10: 88-94, (2000).
Riechmann, et al., "Reshaping human antibodies for therapy", Nature, vol. 332, pp. 323-327, (1988).
Semaphorin Nomenclature Committee, Letter to the Editor, Cell, vol. 97, pp. 551-552, (1999).
Skerra, et al., "Assembly of a functional immunoglobulin $F_v$ fragment in *Escherichia coli*", Science, vol. 240, pp. 1038-1041, (1988).
Smith, et al., "Filamentous fusion phage: Novel expression vectors that display cloned antigens on the virion surface", Science, pp. 1315-1317, (1985).
Soker, et al., "Neuropilin-lis expressed by endothelial and tumor cells as an isoform-specific receptor for vascular endothelial growth factor", Cell, vol. 92, pp. 735-745, (1998).
Takashima, et al., Targeting of both mouse meuropilin-1 and neuropilin-2 genes severely impairs develpmental yolk sac and embryonic angiogenesis, PNAS, vol. 99, No. 6, pp. 3657-3662, (2002).
Tessier-Lavigne, et al., "Common mechanisms of nerve and blood vessel wiring", Nature Reviews, vol. 436, pp. 193-200, (2005).
Ulrich, et al., "Expression studies of catalytic antibodies", PNAS, vol. 921, pp. 11907-11911, (1995).
Vaughan, et al., "Human antibodies with sub-nanomolar affinities isolated from a large non-immunized phage display library", Nature Biotechnology, vol. 14, pp. 309-314, (1996).
Verhoeyen, et al., "Reshaping human antibodies: Grafting an antilysozyme activity", Science, vol. 239, pp. 1534-1536, (1988).
Warren, et al., "Regulation by vascular endothelial growth factor of human colon cancer tumorigenesis in a mouse model of experimenal liver metastasis", Vascular endothelial growth factor in metastic colorectal cancer, J.C.I., 95: 1789-1797, (1995).
Weidner, et al., "Tumor angiogenesis and metastasis-correlation in invasive breast carcinoma", The New England Journal of Medicine, vol. 324, No. 1, pp. 1-8, (1991).
Wildt, et al., "Antobody arrays for high-throughput screening of antibody-antigen interactions", Nature Biology, vol. 18, pp. 989-994, (2000).
Yelton, et al., "Affinity maturation of the BR96 anti-carcinoma antibody by codon-based mutagenesis", The Journal of Immunology, 155: 1994-2004, (1995).
Yuan, et al., "Abnormal lymphatic vessel develpoment in neuropilin 2 mutant mice", Development 129: pp. 4797-4806, (2002).

\* cited by examiner

DRG COLLAPSE ASSAY

FIG. 2C

| | Nrp1b1b2 | Nrp1a2b1b2 | Nrp1b1/Fab | Nrp2b1b2 | Nrp2a2b1b2 | Nrp2a1a2b1b2 | Nrp2a1a2b1b2/Fab | Nrp2a1a2b1b2/Fab |
|---|---|---|---|---|---|---|---|---|
| Data collection | | | | | | | | |
| Space group | P2₁2₁2₁ | P2₁ | H3 | P2₁2₁2₁ | P2₁ | C2 | | P3₂21 |
| Cell dimensions | | | | | | | | |
| a, b, c, (Å) | 65.9, 66.7, 74.7 | 53.2, 68.2, 66.6 | 213, 213, 45.3 | 36.5, 70.5, 122 | 50.1, 193, 66.2 | 148, 106, 92.4 | | 121, 121, 203 |
| αβγ (°) | 90, 90, 90 | 90, 102, 90 | 90, 90, 120 | 90, 90, 90 | 90, 90.1, 90 | 90, 98.8, 90 | | 90, 90, 120 |
| Wavelength (Å) | 0.979 | 0.979 | 0.979 | 1.00 | 1.00 | 1.00 | | 1.00 |
| Resolution (Å) | 50-1.8 | 50-2.0 | 50-2.2 | 50-1.95 | 50-2.3 | 50-2.75 | | 50-3.1 |
| R merge | 5.0 (51.5) | 8.6 (32.2) | 9.6 (48.5) | 8.9 (53.0) | 5.6 (34.4) | 10.4 (52.7) | | 6.1 (51.5) |
| I / σI | 26.9 (3.2) | 13.8 (2.4) | 14.3 (2.2) | 16.8 (3.1) | 20.7 (3.7) | 10.9 (3.3) | | 18.3 (2.6) |
| Completeness (%) | 97.6 (99.3) | 97.5 (88.7) | 99.0 (98.0) | 99.8 (99.9) | 94.5 (85.6) | 99.6 (100) | | 99.6 (98.9) |
| Redundancy | 4.6 (4.6) | 3.5 (3.0) | 4.4 (3.6) | 5.3 (5.2) | 4.2 (4.1) | 4.2 (4.2) | | 3.8 (3.6) |
| Refinement | | | | | | | | |
| Resolution (Å) | 20-1.8 | 20-2.0 | 20-2.2 | 20-1.95 | 20-2.3 | 20-2.75 | | 20-3.1 |
| No. Reflections | 29,017 | 29,213 | 37,085 | 22,404 | 49,667 | 34,437 | | 30,187 |
| Rwork / Rfree | 0.160 / 0.1999 | 0.186 / 0.245 | 0.163 / 0.208 | 0.175 / 0.233 | 0.193 / 0.236 | 0.194 / 0.245 | | 0.202 / 0.241 |
| No. Atoms | | | | | | | | |
| Protein | 2,552 | 3,480 | 4,540 | 2,495 | 6,768 | 7,568 | | 7,681 |
| Ligand/ion | 6 | 101 | 8 | 6 | 2 | 28 | | 0 |
| Water | 267 | 187 | 234 | 234 | 233 | 0 | | 0 |
| B-factors (Å²) | 27.3 | 35.9 | 39.4 | 25.8 | 18.3 | 89.6 | | 111 |
| R.m.s deviations | | | | | | | | |
| Bond lengths (Å) | 0.012 | 0.012 | 0.011 | 0.011 | 0.012 | 0.010 | | 0.008 |
| Bond angles (°) | 1.5 | 1.5 | 1.3 | 1.3 | 1.4 | 1.2 | | 1.2 |

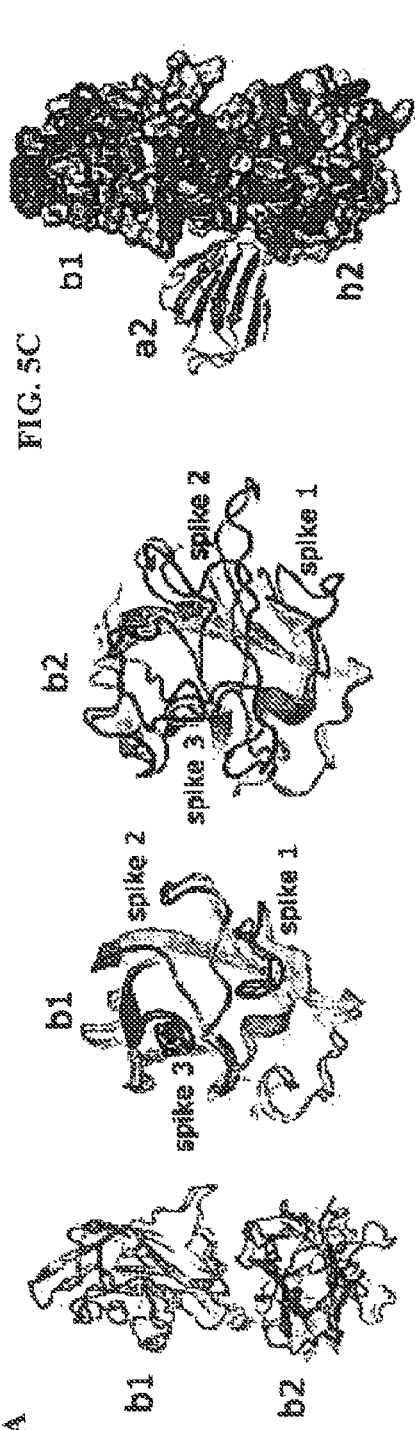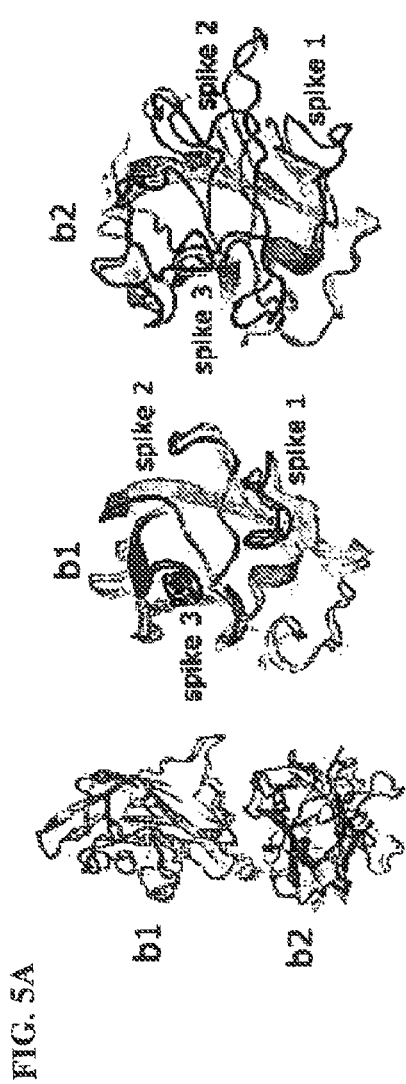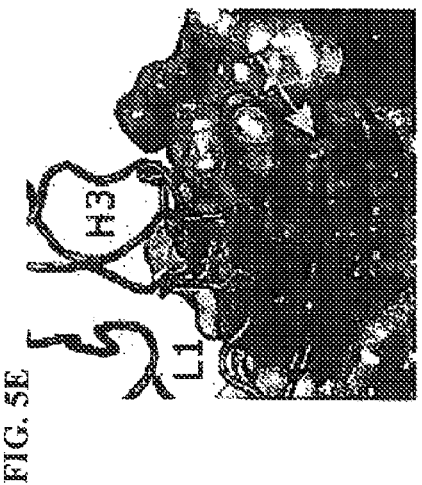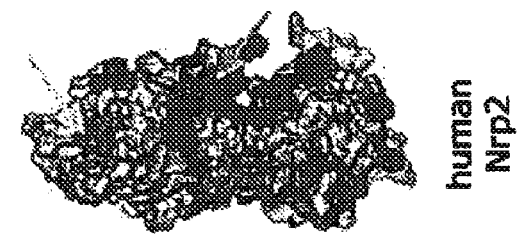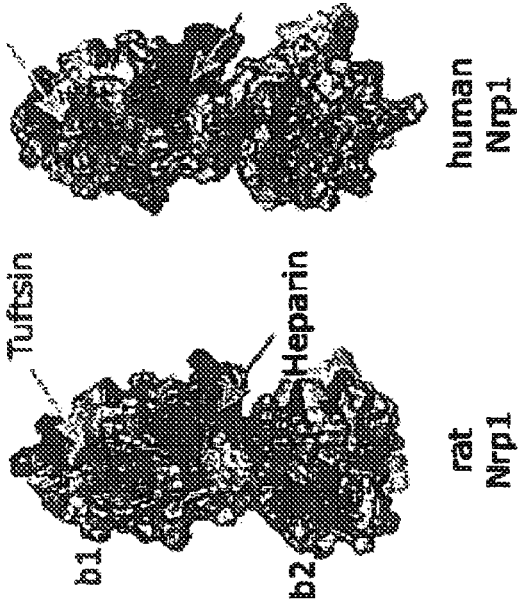

Light Chain Variable Domain Sequence Alignment of Anti-panNRP2A Clones

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | Kabat - CDR L1 | | | | | | | | | | | |
| | | | | | | | | | | | | | | | | | | | | | | | | | | | Chothia - CDR L1 | | | | | | | | | |
| | | | | | | | | | | | | | | | | | | | | | | | | | | | | Contact - CDR L1 | | | | | | | |
| huKI | D | I | Q | M | T | Q | S | P | S | S | L | S | A | S | V | G | D | R | V | T | I | T | C | R | A | S | Q | S | I | S | N | Y | L | A | W | Y | Q |
| YW68.11 | D | I | Q | M | T | Q | S | P | S | S | L | S | A | S | V | G | D | R | V | T | I | T | C | R | A | S | Q | D | V | S | T | A | V | A | W | Y | Q |
| YW68.11.26 | D | I | Q | M | T | Q | S | P | S | S | L | S | A | S | V | G | D | R | V | T | I | T | C | R | A | S | Q | D | V | S | T | A | V | A | W | Y | Q |

| Kabat# | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 |
|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | Kabat - CDR L2 | | | | | | | | | | | | | | | | | | | | | | | |
| | | | | | | | | | | | | | | | Chothia - CDR L2 | | | | | | | | | | | | | | | | | | | | | |
| | | | | | | | | | | Contact - CDR L2 | | | | | | | | | | | | | | | | | | | | | | | | | | |
| huKI | Q | K | P | G | K | A | P | K | L | L | I | Y | A | A | S | S | L | E | S | G | V | P | S | R | F | S | G | S | G | S | G | T | D | F | T | L | T |
| YW68.11 | Q | K | P | G | K | A | P | K | L | L | I | Y | S | A | S | F | L | Y | S | G | V | P | S | R | F | S | G | S | G | S | G | T | D | F | T | L | T |
| YW68.11.26 | Q | K | P | G | K | A | P | K | L | L | I | Y | S | A | S | F | L | Y | S | G | V | P | S | R | F | S | G | S | G | S | G | T | D | F | T | L | T |

| Kabat# | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | Kabat - CDR L3 | | | | | | | | | | | | | | | |
| | | | | | | | | | | | | | | | | | | | | Chothia - CDR L3 | | | | | | | | | | | | | |
| | | | | | | | | | | | | | | | | | | | | Contact - CDR L3 | | | | | | | | | | | | | |
| huKI | D | S | S | L | Q | P | E | D | F | A | T | Y | Y | C | Q | Q | Y | N | S | L | P | W | T | F | G | Q | G | T | K | V | E | I | K | R |
| YW68.11 | D | S | S | L | Q | P | E | D | F | A | T | Y | Y | C | Q | Q | S | Y | T | T | P | T | T | F | G | Q | G | T | K | V | E | I | K | R |
| YW68.11.26 | D | S | S | L | Q | P | E | D | F | A | T | Y | Y | C | Q | Q | A | W | A | Y | L | T | T | F | G | Q | G | T | K | V | E | I | K | R |

FIG. 7

Heavy Chain Variable Domain Sequence Alignment of Anti-panNRP2A Clones

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | Chothia - CDR H1 | | | | | | | | Kabat - CDR H1 | | | | | |
| | | | | | | | | | | | | | | | | | | | | | | | | | | | | | | | | | Contact - CDR H1 | | | | | | |
| hum III | E | V | Q | L | V | E | S | G | G | G | L | V | Q | P | G | G | S | L | R | L | S | C | A | A | S | G | F | T | F | S | S | Y | A | M | S | W | V | R | Q | A |
| YW68.11 | E | V | Q | L | V | E | S | G | G | G | L | V | Q | P | G | G | S | L | R | L | S | C | A | A | S | G | F | T | I | S | G | Y | G | I | H | W | V | R | Q | A |
| YW68.11.26 | E | V | Q | L | V | E | S | G | G | G | L | V | Q | P | G | G | S | L | R | L | S | C | A | A | S | G | F | T | I | S | G | Y | G | I | H | W | V | R | Q | A |

| Kabat# | 41 | 42 | 43 | 44 | 45 | 46 | 47 | 48 | 49 | 50 | 51 | 52 | A | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | Chothia - CDR H2 | | | | | | Kabat - CDR H2 | | | | | | | | | | | | | | | | | | | | | | | |
| | | | | | | | | | | | Contact - CDR H2 | | | | | | | | | | | | | | | | | | | | | | | | | | | | | |
| hum III | P | G | K | G | L | E | W | V | S | V | I | S | | G | D | G | G | S | T | Y | Y | A | D | S | V | K | G | R | F | T | I | S | A | D | T | S | K | N | T | A | Y |
| YW68.11 | P | G | K | G | L | E | W | V | A | Y | I | Y | P | D | S | G | Y | T | D | Y | A | D | S | V | K | G | R | F | T | I | S | A | D | T | S | K | N | T | A | Y |
| YW68.11.26 | P | G | K | G | L | E | W | V | A | Y | I | Y | P | D | S | G | Y | T | D | Y | A | D | S | V | K | G | R | F | T | I | S | A | D | T | S | K | N | T | A | Y |

| Kabat# | 80 | 81 | 82 | A | B | C | 83 | 84 | 85 | 86 | 87 | 88 | 89 | 90 | 91 | 92 | 93 | 94 | 95 | 96 | 97 | 98 | 99 | 100 | A | B | C | D | E | F | G | 101 | 102 | 103 | 104 | 105 | 106 | 107 |
|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | Kabat - CDR H3 | | | | | | | | | | |
| | | | | | | | | | | | | | | | | | | | | | | | | | | | | Chothia - CDR H3 | | | | | | | | | | |
| | | | | | | | | | | | | | | | | | | | | | | | | | | | | Contact - CDR H3 | | | | | | | | | | |
| hum III | L | Q | M | N | S | L | R | A | E | D | T | A | V | Y | Y | Y | C | A | R | G | | | | | | | | | | | | F | D | Y | W | G | Q | G | T |
| YW68.11 | L | Q | M | N | S | L | R | A | E | D | T | A | V | Y | Y | Y | C | A | R | E | D | F | R | N | R | R | R | L | W | Y | Y | V | M | D | Y | W | G | Q | G | T |
| YW68.11.26 | L | Q | M | N | S | L | R | A | E | D | T | A | V | Y | Y | Y | C | A | R | E | D | F | R | N | R | R | R | L | W | Y | Y | V | M | D | Y | W | G | Q | G | T |

FIG. 8

Anti-panNRP2 YW68.11 hIgG1 P1 file

DIQMTQSPSSLSASVGDRVTITC RASQDVSTAVA WYQQKPGKAPKLLIY SA
SFLYS GVPSRFSGSGSGTDFTLTISSLQPEDFATYYC QQSYTTPP TFGQGTK
VEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPV
TKSFNRGECEVQLVESGGGLVQPGGSLRLSCAAS GFTISGYGIH WVRQAPG
KGLEWVA YIYPDSGYTDYADSVKG RFTISADTSKNTAYLQMNSLRAEDTA
VYYCAR EDFRNRRRLWYVMDY WGQGTLVTVSSASTKGPSVFPLAPSSKS
TSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQ
PENNYKTTPPVLDSDGSFFLYSKLTVDKSRWQQGNVFSCSVMHEALHNHY
TQKSLSLSPGK

FIG. 9A

Anti-panNRP2 YW68.11.26 hIgG1 P1 file

DIQMTQSPSSLSASVGDRVTITC RASQDVSTAVA WYQQKPGKAPKLLIY SA
SFLYS GVPSRFSGSGSGTDFTLTISSLQPEDFATYYC QQAWAYLPT FGQGT
KVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGECEVQLVESGGGLVQPGGSLRLSCAAS GFTISGYGIH WVRQAP
GKGLEWVA YIYPDSGYTDYADSVKG RFTISADTSKNTAYLQMNSLRAEDT
AVYYCAR EDFRNRRRLWYVMDY WGQGTLVTVSSASTKGPSVFPLAPSSK
STSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNH
YTQKSLSLSPGK

| | Nrp Residue Range | Final Conc. (mg/mL) | Protein Buffer | Crystallization Buffer | Cryoprotectant |
|---|---|---|---|---|---|
| Nrp1$_{b1b2}$ | Phe$^{273}$-Glu$^{586}$ | 15 | 10 mM Tris-HCl (pH 7.5) 50 mM NaCl | 20% PEG 3,350 0.2 M Sodium Fluoride | Well solution + 20% glycerol |
| Nrp1$_{a2b1b2}$ | Phe$^{141}$-Glu$^{586}$ | 11 | 10 mM Tris-HCl (pH 7.5) 50 mM NaCl | 0.1 M MES (pH 6.5) 12% PEG 20,000 | Well solution + 20% ethylene glycol |
| Nrp1$_{b1}$/Fab (anti-Nrp1$^B$) | Phe$^{273}$-Thr$^{427}$ | 15 | 10 mM Hepes (pH 7.2) 100 mM NaCl | 25% PEG 1,500 4% tert-butanol | 10 mM Hepes (pH 7.2) 25% PEG 1,500 10% ethylene glycol |
| Nrp2$_{b1b2}$ | Phe$^{275}$-Thr$^{595}$ | 12 | 25 mM Tris-HCl (pH 7.5) 150 mM NaCl | 0.1 M Bis-Tris (pH 6.5) 20% PEG 5,000 MME | Well solution + 20% glycerol |
| Nrp2$_{a2b1b2}$ | Gly$^{145}$-Thr$^{595}$ | 15 | 20 mM Tris-HCl (pH 7.5) 300 mM NaCl 1 mM CaCl$_2$ | 0.1 M Hepes (pH 7.5) 10% PEG 8,000 | Well solution + 20% ethylene glycol |
| Nrp2$_{a1a2b1b2}$/Fab (anti-panNrp$^A$) Monoclinic form | Met$^1$-Thr$^{595}$ | 13 | 25 mM Tris-HCl (pH 7.5) 200 mM NaCl | 0.1 M Hepes (pH 7.5) 22% polyacrylic acid 5100 0.02 M MgCl$_2$ | Well solution + 20% glycerol |
| Nrp2$_{a1a2b1b2}$/Fab (anti-panNrp$^A$) Trigonal form | Met$^1$-Thr$^{595}$ | 13 | 25 mM Tris-HCl (pH 7.5) 200 mM NaCl | 10% PEG 1,000 10% PEG 8,000 | Well solution + 20% glycerol |

FIG. 13A

SEQUENCE LISTING

<160> NUMBER OF SEQ ID NOS: 39

<210> SEQ ID NO 1
<211> LENGTH: 568
<212> TYPE: PRT
<213> ORGANISM: Homo sapiens

<400> SEQUENCE: 1

Cys Gly Gly Arg Leu Asn Ser Lys Asp Ala Gly Tyr Ile Thr Ser Pro
1               5                   10                  15

Gly Tyr Pro Gln Asp Tyr Pro Ser His Gln Asn Cys Glu Trp Ile Val
            20                  25                  30

Tyr Ala Pro Glu Pro Asn Gln Lys Ile Val Leu Asn Phe Asn Pro His
        35                  40                  45

Phe Glu Ile Glu Lys His Asp Cys Lys Tyr Asp Phe Ile Glu Ile Arg
    50                  55                  60

Asp Gly Asp Ser Glu Ser Ala Asp Leu Leu Gly Lys His Cys Gly Asn
65                  70                  75                  80

Ile Ala Pro Pro Thr Ile Ile Ser Ser Gly Ser Met Leu Tyr Ile Lys

```
                    85                  90                  95
Phe Thr Ser Asp Tyr Ala Arg Gln Gly Ala Gly Phe Ser Leu Arg Tyr
            100                 105                 110

Glu Ile Phe Lys Thr Gly Ser Glu Asp Cys Ser Lys Asn Phe Thr Ser
            115                 120                 125

Pro Asn Gly Thr Ile Glu Ser Pro Gly Phe Pro Lys Tyr Pro His
            130                 135                 140

Asn Leu Asp Cys Thr Phe Thr Ile Leu Ala Lys Pro Lys Met Glu Ile
145                 150                 155                 160

Ile Leu Gln Phe Leu Ile Phe Asp Leu Glu His Asp Pro Leu Gln Val
                165                 170                 175

Gly Glu Gly Asp Cys Lys Tyr Asp Trp Leu Asp Ile Trp Asp Gly Ile
                180                 185                 190

Pro His Val Gly Pro Leu Ile Gly Lys Tyr Cys Gly Thr Lys Thr Pro
            195                 200                 205

Ser Glu Leu Arg Ser Ser Thr Gly Ile Leu Ser Leu Thr Phe His Thr
            210                 215                 220

Asp Met Ala Val Ala Lys Asp Gly Phe Ser Ala Arg Tyr Tyr Leu Val
225                 230                 235                 240

His Gln Glu Pro Leu Glu Asn Phe Gln Cys Asn Val Pro Leu Gly Met
                245                 250                 255

Glu Ser Gly Arg Ile Ala Asn Glu Gln Ile Ser Ala Ser Ser Thr Tyr
                260                 265                 270

Ser Asp Gly Arg Trp Thr Pro Gln Gln Ser Arg Leu His Gly Asp Asp
            275                 280                 285

Asn Gly Trp Thr Pro Asn Leu Asp Ser Asn Lys Glu Tyr Leu Gln Val
            290                 295                 300

Asp Leu Arg Phe Leu Thr Met Leu Thr Ala Ile Ala Thr Gln Gly Ala
305                 310                 315                 320

Ile Ser Arg Glu Thr Gln Asn Gly Tyr Tyr Val Lys Ser Tyr Lys Leu
                325                 330                 335

Glu Val Ser Thr Asn Gly Glu Asp Trp Met Val Tyr Arg His Gly Lys
            340                 345                 350

Asn His Lys Val Phe Gln Ala Asn Asn Asp Ala Thr Glu Val Val Leu
            355                 360                 365

Asn Lys Leu His Ala Pro Leu Leu Thr Arg Phe Val Arg Ile Arg Pro
            370                 375                 380

Gln Thr Trp His Ser Gly Ile Ala Leu Arg Leu Glu Leu Phe Gly Cys
385                 390                 395                 400

Arg Val Thr Asp Ala Pro Cys Ser Asn Met Leu Gly Met Leu Ser Gly
                405                 410                 415

Leu Ile Ala Asp Ser Gln Ile Ser Ala Ser Ser Thr Gln Glu Tyr Leu
            420                 425                 430

Trp Ser Pro Ser Ala Ala Arg Leu Val Ser Ser Arg Ser Gly Trp Phe
            435                 440                 445

Pro Arg Ile Pro Gln Ala Gln Pro Gly Glu Glu Trp Leu Gln Val Asp
            450                 455                 460

Leu Gly Thr Pro Lys Thr Val Lys Gly Val Ile Ile Gln Gly Ala Arg
465                 470                 475                 480

Gly Gly Asp Ser Ile Thr Ala Val Glu Ala Arg Ala Phe Val Arg Lys
                485                 490                 495

Phe Lys Val Ser Tyr Ser Leu Asn Gly Lys Asp Trp Glu Tyr Ile Gln
            500                 505                 510
```

```
Asp Pro Arg Thr Gln Gln Pro Lys Leu Phe Glu Gly Asn Met His Tyr
        515                 520                 525
Asp Thr Pro Asp Ile Arg Arg Phe Asp Pro Ile Pro Ala Gln Tyr Val
        530                 535                 540
Arg Val Tyr Pro Glu Arg Trp Ser Pro Ala Gly Ile Gly Met Arg Leu
545                 550                 555                 560
Glu Val Leu Gly Cys Asp Trp Thr
                565

<210> SEQ ID NO 2
<211> LENGTH: 558
<212> TYPE: PRT
<213> ORGANISM: Homo sapiens

<400> SEQUENCE: 2

Cys Gly Asp Thr Ile Lys Ile Glu Ser Pro Gly Tyr Leu Thr Ser Pro
1               5                   10                  15
Gly Tyr Pro His Ser Tyr His Pro Ser Glu Lys Cys Glu Trp Leu Ile
                20                  25                  30
Gln Ala Pro Asp Pro Tyr Gln Arg Ile Met Ile Asn Phe Asn Pro His
            35                  40                  45
Phe Asp Leu Glu Asp Arg Asp Cys Lys Tyr Asp Tyr Val Glu Val Phe
    50                  55                  60
Asp Gly Glu Asn Glu Asn Gly His Phe Arg Gly Lys Phe Cys Gly Lys
65                  70                  75                  80
Ile Ala Pro Pro Val Val Ser Ser Gly Pro Phe Leu Phe Ile Lys
                85                  90                  95
Phe Val Ser Asp Tyr Glu Thr His Gly Ala Gly Phe Ser Ile Arg Tyr
                100                 105                 110
Glu Ile Phe Lys Arg Gly Pro Glu Cys Ser Gln Asn Tyr Thr Thr Pro
            115                 120                 125
Ser Gly Val Ile Lys Ser Pro Gly Phe Pro Glu Lys Tyr Pro Asn Ser
    130                 135                 140
Leu Glu Cys Thr Tyr Ile Val Phe Ala Pro Lys Met Ser Glu Ile Ile
145                 150                 155                 160
Leu Glu Phe Glu Ser Phe Asp Leu Pro Asp Ser Asn Pro Pro Gly Gly
                165                 170                 175
Met Phe Cys Arg Tyr Arg Leu Glu Ile Trp Asp Gly Phe Pro Asp Val
            180                 185                 190
Gly Pro His Ile Gly Arg Tyr Cys Gly Gln Lys Thr Pro Gly Arg Ile
        195                 200                 205
Arg Ser Ser Ser Gly Ile Leu Ser Met Val Phe Tyr Thr Asp Ser Ala
    210                 215                 220
Ile Ala Lys Glu Gly Phe Ser Ala Asn Tyr Ser Val Leu Gln Ser Ser
225                 230                 235                 240
Val Ser Glu Asp Phe Lys Cys Met Glu Ala Leu Gly Met Glu Ser Gly
                245                 250                 255
Glu Ile His Ser Asp Gln Ile Thr Ala Ser Ser Gln Tyr Ser Thr Asn
            260                 265                 270
Trp Ser Ala Glu Arg Ser Arg Leu Asn Tyr Pro Glu Asn Gly Trp Thr
        275                 280                 285
Pro Gly Glu Asp Ser Tyr Arg Glu Trp Ile Gln Val Asp Leu Gly Leu
    290                 295                 300
Leu Arg Phe Val Thr Ala Val Gly Thr Gln Gly Ala Ile Ser Lys Glu
305                 310                 315                 320
```

Thr Lys Lys Lys Tyr Tyr Val Lys Thr Tyr Lys Ile Asp Val Ser Ser
            325                 330                 335

Asn Gly Glu Asp Trp Ile Thr Ile Lys Glu Gly Asn Lys Pro Val Leu
            340                 345                 350

Phe Gln Gly Asn Thr Asn Pro Thr Asp Val Val Ala Val Phe Pro
            355                 360                 365

Lys Pro Leu Ile Thr Arg Phe Val Arg Ile Lys Pro Ala Thr Trp Glu
            370                 375                 380

Thr Gly Ile Ser Met Arg Phe Glu Val Tyr Gly Cys Lys Ile Thr Asp
385                 390                 395                 400

Tyr Pro Cys Ser Gly Met Leu Gly Met Val Ser Gly Leu Ile Ser Asp
            405                 410                 415

Ser Gln Ile Thr Ser Ser Asn Gln Gly Asp Arg Asn Trp Met Pro Glu
            420                 425                 430

Asn Ile Arg Leu Val Thr Ser Arg Ser Gly Trp Ala Leu Pro Pro Ala
            435                 440                 445

Pro His Ser Tyr Ile Asn Glu Trp Leu Gln Ile Asp Leu Gly Glu Glu
            450                 455                 460

Lys Ile Val Arg Gly Ile Ile Gln Gly Gly Lys His Arg Glu Asn
465                 470                 475                 480

Lys Val Phe Met Arg Lys Phe Lys Ile Gly Tyr Ser Asn Asn Gly Ser
            485                 490                 495

Asp Trp Lys Met Ile Met Asp Asp Ser Lys Arg Lys Ala Lys Ser Phe
            500                 505                 510

Glu Gly Asn Asn Asn Tyr Asp Thr Pro Glu Leu Arg Thr Phe Pro Ala
            515                 520                 525

Leu Ser Thr Arg Glu Ile Arg Ile Tyr Pro Glu Arg Ala Thr His Gly
            530                 535                 540

Gly Leu Gly Leu Arg Met Glu Leu Leu Gly Cys Glu Val Glu
545                 550                 555

<210> SEQ ID NO 3
<211> LENGTH: 108
<212> TYPE: PRT
<213> ORGANISM: Homo sapiens

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
            35                  40                  45

Tyr Ala Ala Ser Ser Leu Glu Ser Gly Val Pro Ser Arg Phe Ser Gly
        50                  55                  60

Ser Gly Ser Gly Thr Asp Phe Thr Leu Thr Asp Ser Ser Leu Gln Pro
65                  70                  75                  80

Glu Asp Phe Ala Thr Tyr Tyr Cys Gln Gln Tyr Asn Ser Leu Pro Trp
            85                  90                  95

Thr Phe Gly Gln Gly Thr Lys Val Glu Ile Lys Arg
            100                 105

<210> SEQ ID NO 4
<211> LENGTH: 108
<212> TYPE: PRT
<213> ORGANISM: Homo sapiens -continued

```
<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Asp Ser Ser Leu Gln Pro
65                  70                  75                  80

Glu Asp Phe Ala Thr Tyr Tyr Cys Gln Gln Ser Tyr Thr Thr Pro Thr
                85                  90                  95

Thr Phe Gly Gln Gly Thr Lys Val Glu Ile Lys Arg
            100                 105

<210> SEQ ID NO 5
<211> LENGTH: 108
<212> TYPE: PRT
<213> ORGANISM: Homo sapiens

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Asp Ser Ser Leu Gln Pro
65                  70                  75                  80

Glu Asp Phe Ala Thr Tyr Tyr Cys Gln Gln Ala Trp Ala Tyr Leu Thr
                85                  90                  95

Thr Phe Gly Gln Gly Thr Lys Val Glu Ile Lys Arg
            100                 105

<210> SEQ ID NO 6
<211> LENGTH: 107
<212> TYPE: PRT
<213> ORGANISM: Homo sapiens

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Asp Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Phe Asp Tyr Trp Gly Gln Gly Thr
            100                 105
```

<210> SEQ ID NO 7
<211> LENGTH: 118
<212> TYPE: PRT
<213> ORGANISM: Homo sapiens

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Gly Tyr
            20                  25                  30

Gly Ile His Trp Val Arg Gln Ala Pro Gly Lys Gly Leu Glu Trp Val
        35                  40                  45

Ala Tyr Ile Tyr Pro Asp Ser Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Asp Phe Arg Asn Arg Arg Leu Trp Tyr Val Met Asp
            100                 105                 110

Tyr Trp Gly Gln Gly Thr
        115

<210> SEQ ID NO 8

<400> SEQUENCE: 8

000

<210> SEQ ID NO 9
<211> LENGTH: 668
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Val Gln Leu Val Glu Ser Gly Gly Gly
    210                 215                 220
Leu Val Gln Pro Gly Gly Ser Leu Arg Leu Ser Cys Ala Ala Ser Gly
225                 230                 235                 240
Phe Thr Ile Ser Gly Tyr Gly Ile His Trp Val Arg Gln Ala Pro Gly
                245                 250                 255
Lys Gly Leu Glu Trp Val Ala Tyr Ile Tyr Pro Asp Ser Gly Tyr Thr
            260                 265                 270
Asp Tyr Ala Asp Ser Val Lys Gly Arg Phe Thr Ile Ser Ala Asp Thr
        275                 280                 285
Ser Lys Asn Thr Ala Tyr Leu Gln Met Asn Ser Leu Arg Ala Glu Asp
    290                 295                 300
Thr Ala Val Tyr Tyr Cys Ala Arg Glu Asp Phe Arg Asn Arg Arg
305                 310                 315                 320
Leu Trp Tyr Val Met Asp Tyr Trp Gly Gln Gly Thr Leu Val Thr Val
                325                 330                 335
Ser Ser Ala Ser Thr Lys Gly Pro Ser Val Phe Pro Leu Ala Pro Ser
            340                 345                 350
Ser Lys Ser Thr Ser Gly Gly Thr Ala Ala Leu Gly Cys Leu Val Lys
        355                 360                 365
Asp Tyr Phe Pro Glu Pro Val Thr Val Ser Trp Asn Ser Gly Ala Leu
    370                 375                 380
Thr Ser Gly Val His Thr Phe Pro Ala Val Leu Gln Ser Ser Gly Leu
385                 390                 395                 400
Tyr Ser Leu Ser Ser Val Val Thr Val Pro Ser Ser Ser Leu Gly Thr
                405                 410                 415
Gln Thr Tyr Ile Cys Asn Val Asn His Lys Pro Ser Asn Thr Lys Val
            420                 425                 430
Asp Lys Lys Val Glu Pro Lys Ser Cys Asp Lys Thr His Thr Cys Pro
        435                 440                 445
Pro Cys Pro Ala Pro Glu Leu Leu Gly Gly Pro Ser Val Phe Leu Phe
    450                 455                 460
Pro Pro Lys Pro Lys Asp Thr Leu Met Ile Ser Arg Thr Pro Glu Val
465                 470                 475                 480
Thr Cys Val Val Val Asp Val Ser His Glu Asp Pro Glu Val Lys Phe
                485                 490                 495
Asn Trp Tyr Val Asp Gly Val Glu Val His Asn Ala Lys Thr Lys Pro
            500                 505                 510
Arg Glu Glu Gln Tyr Asn Ser Thr Tyr Arg Val Val Ser Val Leu Thr
        515                 520                 525
Val Leu His Gln Asp Trp Leu Asn Gly Lys Glu Tyr Lys Cys Lys Val
    530                 535                 540
Ser Asn Lys Ala Leu Pro Ala Pro Ile Glu Lys Thr Ile Ser Lys Ala
545                 550                 555                 560
Lys Gly Gln Pro Arg Glu Pro Gln Val Tyr Thr Leu Pro Pro Ser Arg
                565                 570                 575
Glu Glu Met Thr Lys Asn Gln Val Ser Leu Thr Cys Leu Val Lys Gly
            580                 585                 590
Phe Tyr Pro Ser Asp Ile Ala Val Glu Trp Glu Ser Asn Gly Gln Pro
```

-continued

```
                595                 600                 605
Glu Asn Asn Tyr Lys Thr Thr Pro Pro Val Leu Asp Ser Asp Gly Ser
            610                 615                 620

Phe Phe Leu Tyr Ser Lys Leu Thr Val Asp Lys Ser Arg Trp Gln Gln
625                 630                 635                 640

Gly Asn Val Phe Ser Cys Ser Val Met His Glu Ala Leu His Asn His
                645                 650                 655

Tyr Thr Gln Lys Ser Leu Ser Leu Ser Pro Gly Lys
            660                 665

<210> SEQ ID NO 10
<211> LENGTH: 668
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Trp Ala Tyr Leu Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Val Gln Leu Val Glu Ser Gly Gly Gly
    210                 215                 220

Leu Val Gln Pro Gly Gly Ser Leu Arg Leu Ser Cys Ala Ala Ser Gly
225                 230                 235                 240

Phe Thr Ile Ser Gly Tyr Gly Ile His Trp Val Arg Gln Ala Pro Gly
                245                 250                 255

Lys Gly Leu Glu Trp Val Ala Tyr Ile Tyr Pro Asp Ser Gly Tyr Thr
            260                 265                 270

Asp Tyr Ala Asp Ser Val Lys Gly Arg Phe Thr Ile Ser Ala Asp Thr
        275                 280                 285

Ser Lys Asn Thr Ala Tyr Leu Gln Met Asn Ser Leu Arg Ala Glu Asp
    290                 295                 300

Thr Ala Val Tyr Tyr Cys Ala Arg Glu Asp Phe Arg Asn Arg Arg
```

```
                305                 310                 315                 320
Leu Trp Tyr Val Met Asp Tyr Trp Gly Gln Gly Thr Leu Val Thr Val
                    325                 330                 335
Ser Ser Ala Ser Thr Lys Gly Pro Ser Val Phe Pro Leu Ala Pro Ser
                340                 345                 350
Ser Lys Ser Thr Ser Gly Gly Thr Ala Ala Leu Gly Cys Leu Val Lys
            355                 360                 365
Asp Tyr Phe Pro Glu Pro Val Thr Val Ser Trp Asn Ser Gly Ala Leu
        370                 375                 380
Thr Ser Gly Val His Thr Phe Pro Ala Val Leu Gln Ser Ser Gly Leu
385                 390                 395                 400
Tyr Ser Leu Ser Ser Val Val Thr Val Pro Ser Ser Ser Leu Gly Thr
                405                 410                 415
Gln Thr Tyr Ile Cys Asn Val Asn His Lys Pro Ser Asn Thr Lys Val
                420                 425                 430
Asp Lys Lys Val Glu Pro Lys Ser Cys Asp Lys Thr His Thr Cys Pro
            435                 440                 445
Pro Cys Pro Ala Pro Glu Leu Leu Gly Gly Pro Ser Val Phe Leu Phe
        450                 455                 460
Pro Pro Lys Pro Lys Asp Thr Leu Met Ile Ser Arg Thr Pro Glu Val
465                 470                 475                 480
Thr Cys Val Val Val Asp Val Ser His Glu Asp Pro Glu Val Lys Phe
                485                 490                 495
Asn Trp Tyr Val Asp Gly Val Glu Val His Asn Ala Lys Thr Lys Pro
                500                 505                 510
Arg Glu Glu Gln Tyr Asn Ser Thr Tyr Arg Val Val Ser Val Leu Thr
            515                 520                 525
Val Leu His Gln Asp Trp Leu Asn Gly Lys Glu Tyr Lys Cys Lys Val
        530                 535                 540
Ser Asn Lys Ala Leu Pro Ala Pro Ile Glu Lys Thr Ile Ser Lys Ala
545                 550                 555                 560
Lys Gly Gln Pro Arg Glu Pro Gln Val Tyr Thr Leu Pro Pro Ser Arg
                565                 570                 575
Glu Glu Met Thr Lys Asn Gln Val Ser Leu Thr Cys Leu Val Lys Gly
                580                 585                 590
Phe Tyr Pro Ser Asp Ile Ala Val Glu Trp Glu Ser Asn Gly Gln Pro
            595                 600                 605
Glu Asn Asn Tyr Lys Thr Thr Pro Pro Val Leu Asp Ser Asp Gly Ser
        610                 615                 620
Phe Phe Leu Tyr Ser Lys Leu Thr Val Asp Lys Ser Arg Trp Gln Gln
625                 630                 635                 640
Gly Asn Val Phe Ser Cys Ser Val Met His Glu Ala Leu His Asn His
                645                 650                 655
Tyr Thr Gln Lys Ser Leu Ser Leu Ser Pro Gly Lys
                660                 665

<210> SEQ ID NO 11
<211> LENGTH: 116
<212> TYPE: PRT
<213> ORGANISM: Homo sapiens

<400> SEQUENCE: 11

Cys Gly Asp Thr Ile Lys Ile Glu Ser Pro Gly Tyr Leu Thr Ser Pro
1               5                   10                  15

Gly Tyr Pro His Ser Tyr His Pro Ser Glu Lys Cys Glu Trp Leu Ile
```

```
                20                  25                  30
Gln Ala Pro Asp Pro Tyr Gln Arg Ile Met Ile Asn Phe Asn Pro His
        35                  40                  45
Phe Asp Leu Glu Asp Arg Asp Cys Lys Tyr Asp Tyr Val Glu Val Phe
    50                  55                  60
Asp Gly Glu Asn Glu Asn Gly His Phe Arg Gly Lys Phe Cys Gly Lys
65                  70                  75                  80
Ile Ala Pro Pro Val Val Ser Ser Gly Pro Phe Leu Phe Ile Lys
                85                  90                  95
Phe Val Ser Asp Tyr Glu Thr His Gly Ala Gly Phe Ser Ile Arg Tyr
            100                 105                 110
Glu Ile Phe Lys
        115

<210> SEQ ID NO 12
<211> LENGTH: 116
<212> TYPE: PRT
<213> ORGANISM: Homo sapiens

<400> SEQUENCE: 12

Cys Gly Gly Arg Leu Asn Ser Lys Asp Ala Gly Tyr Ile Thr Ser Pro
1               5                   10                  15
Gly Tyr Pro Gln Asp Tyr Pro Ser His Gln Asn Cys Glu Trp Ile Val
                20                  25                  30
Tyr Ala Pro Glu Pro Asn Gln Lys Ile Val Leu Asn Phe Asn Pro His
        35                  40                  45
Phe Glu Ile Glu Lys His Asp Cys Lys Tyr Asp Phe Ile Glu Ile Arg
    50                  55                  60
Asp Gly Asp Ser Glu Ser Ala Asp Leu Leu Gly Lys His Cys Gly Asn
65                  70                  75                  80
Ile Ala Pro Pro Thr Ile Ile Ser Ser Gly Ser Met Leu Tyr Ile Lys
                85                  90                  95
Phe Thr Ser Asp Tyr Ala Arg Gln Gly Ala Gly Phe Ser Leu Arg Tyr
            100                 105                 110
Glu Ile Phe Lys
        115

<210> SEQ ID NO 13
<211> LENGTH: 120
<212> TYPE: PRT
<213> ORGANISM: Homo sapiens

<400> SEQUENCE: 13

Cys Ser Gln Asn Tyr Thr Thr Pro Ser Gly Val Ile Lys Ser Pro Gly
1               5                   10                  15
Phe Pro Glu Lys Tyr Pro Asn Ser Leu Glu Cys Thr Tyr Ile Val Phe
                20                  25                  30
Ala Pro Lys Met Ser Glu Ile Ile Leu Glu Phe Glu Ser Phe Asp Leu
        35                  40                  45
Glu Pro Asp Ser Asn Pro Gly Gly Met Phe Cys Arg Tyr Asp Arg
    50                  55                  60
Leu Glu Ile Trp Asp Gly Phe Pro Asp Val Gly Pro His Ile Gly Arg
65                  70                  75                  80
Tyr Cys Gly Gln Lys Thr Pro Gly Arg Ile Arg Ser Ser Gly Ile
                85                  90                  95
Leu Ser Met Val Phe Tyr Thr Asp Ser Ala Ile Ala Lys Glu Gly Phe
            100                 105                 110
```

Ser Ala Asn Tyr Ser Val Leu Gln
        115                 120

<210> SEQ ID NO 14
<211> LENGTH: 110
<212> TYPE: PRT
<213> ORGANISM: Homo sapiens

<400> SEQUENCE: 14

Cys Ser Lys Asn Phe Thr Ser Pro Asn Gly Thr Ile Glu Ser Pro Gly
1               5                   10                  15

Phe Pro Glu Lys Tyr Pro His Asn Leu Asp Cys Thr Phe Thr Ile Leu
            20                  25                  30

Ala Lys Pro Lys Met Glu Ile Ile Leu Gln Phe Leu Ile Phe Asp Leu
        35                  40                  45

Glu Cys Lys Tyr Asp Trp Leu Asp Ile Trp Asp Gly Ile Pro His Val
    50                  55                  60

Gly Pro Leu Ile Gly Lys Tyr Cys Gly Thr Lys Thr Pro Asp Glu Leu
65                  70                  75                  80

Arg Ser Ser Thr Gly Ile Leu Ser Leu Thr Phe His Thr Asp Met Ala
                85                  90                  95

Val Ala Lys Asp Gly Phe Ser Ala Arg Tyr Tyr Leu Val His
            100                 105                 110

<210> SEQ ID NO 15
<211> LENGTH: 568
<212> TYPE: PRT
<213> ORGANISM: Homo sapiens

<400> SEQUENCE: 15

Cys Gly Gly Arg Leu Asn Ser Lys Asp Ala Gly Tyr Ile Thr Ser Pro
1               5                   10                  15

Gly Tyr Pro Gln Asp Tyr Pro Ser His Gln Asn Cys Glu Trp Ile Val
            20                  25                  30

Tyr Ala Pro Glu Pro Asn Gln Lys Ile Val Leu Asn Phe Asn Pro His
        35                  40                  45

Phe Glu Ile Glu Lys His Asp Cys Lys Tyr Asp Phe Ile Glu Ile Arg
    50                  55                  60

Asp Gly Asp Ser Glu Ser Ala Asp Leu Leu Gly Lys His Cys Gly Asn
65                  70                  75                  80

Ile Ala Pro Pro Thr Ile Ile Ser Ser Gly Ser Met Leu Tyr Ile Lys
                85                  90                  95

Phe Thr Ser Asp Tyr Ala Arg Gln Gly Ala Gly Phe Ser Leu Arg Tyr
            100                 105                 110

Glu Ile Phe Lys Thr Gly Ser Glu Asp Cys Ser Lys Asn Phe Thr Ser
        115                 120                 125

Pro Asn Gly Thr Ile Glu Ser Pro Gly Phe Pro Glu Lys Tyr Pro His
    130                 135                 140

Asn Leu Asp Cys Thr Phe Thr Ile Leu Ala Lys Pro Lys Met Glu Ile
145                 150                 155                 160

Ile Leu Gln Phe Leu Ile Phe Asp Leu Glu His Asp Pro Leu Gln Val
                165                 170                 175

Gly Glu Gly Asp Cys Lys Tyr Asp Trp Leu Asp Ile Trp Asp Gly Ile
            180                 185                 190

Pro His Val Gly Pro Leu Ile Gly Lys Tyr Cys Gly Thr Lys Thr Pro
        195                 200                 205

```
Ser Glu Leu Arg Ser Ser Thr Gly Ile Leu Ser Leu Thr Phe His Thr
    210                 215                 220

Asp Met Ala Val Ala Lys Asp Gly Phe Ser Ala Arg Tyr Tyr Leu Val
225                 230                 235                 240

His Gln Glu Pro Leu Glu Asn Phe Gln Cys Asn Val Pro Leu Gly Met
                245                 250                 255

Glu Ser Gly Arg Ile Ala Asn Glu Gln Ile Ser Ala Ser Ser Thr Tyr
            260                 265                 270

Ser Asp Gly Arg Trp Thr Pro Gln Gln Ser Arg Leu His Gly Asp Asp
        275                 280                 285

Asn Gly Trp Thr Pro Asn Leu Asp Ser Asn Lys Glu Tyr Leu Gln Val
    290                 295                 300

Asp Leu Arg Phe Leu Thr Met Leu Thr Ala Ile Ala Thr Gln Gly Ala
305                 310                 315                 320

Ile Ser Arg Glu Thr Gln Asn Gly Tyr Tyr Val Lys Ser Tyr Lys Leu
                325                 330                 335

Glu Val Ser Thr Asn Gly Glu Asp Trp Met Val Tyr Arg His Gly Lys
            340                 345                 350

Asn His Lys Val Phe Gln Ala Asn Asn Asp Ala Thr Glu Val Val Leu
    355                 360                 365

Asn Lys Leu His Ala Pro Leu Leu Thr Arg Phe Val Arg Ile Arg Pro
370                 375                 380

Gln Thr Trp His Ser Gly Ile Ala Leu Arg Leu Glu Leu Phe Gly Cys
385                 390                 395                 400

Arg Val Thr Asp Ala Pro Cys Ser Asn Met Leu Gly Met Leu Ser Gly
                405                 410                 415

Leu Ile Ala Asp Ser Gln Ile Ser Ala Ser Ser Thr Gln Glu Tyr Leu
            420                 425                 430

Trp Ser Pro Ser Ala Ala Arg Leu Val Ser Ser Arg Ser Gly Trp Phe
        435                 440                 445

Pro Arg Ile Pro Gln Ala Gln Pro Gly Glu Glu Trp Leu Gln Val Asp
    450                 455                 460

Leu Gly Thr Pro Lys Thr Val Lys Gly Val Ile Ile Gln Gly Ala Arg
465                 470                 475                 480

Gly Gly Asp Ser Ile Thr Ala Val Glu Ala Arg Ala Phe Val Arg Lys
                485                 490                 495

Phe Lys Val Ser Tyr Ser Leu Asn Gly Lys Asp Trp Glu Tyr Ile Gln
            500                 505                 510

Asp Pro Arg Thr Gln Gln Pro Lys Leu Phe Glu Gly Asn Met His Tyr
        515                 520                 525

Asp Thr Pro Asp Ile Arg Arg Phe Asp Pro Ile Pro Ala Gln Tyr Val
    530                 535                 540

Arg Val Tyr Pro Glu Arg Trp Ser Pro Ala Gly Ile Gly Met Arg Leu
545                 550                 555                 560

Arg Val Leu Gly Cys Asp Trp Thr
                565

<210> SEQ ID NO 16
<211> LENGTH: 568
<212> TYPE: PRT
<213> ORGANISM: Mus musculus

<400> SEQUENCE: 16

Cys Gly Gly Arg Pro Asn Ser Lys Asp Ala Gly Tyr Ile Thr Ser Pro
1               5                   10                  15
```

-continued

```
Gly Tyr Pro Gln Asp Tyr Pro Ser His Gln Asn Cys Glu Trp Ile Val
             20                  25                  30

Tyr Ala Pro Glu Pro Asn Gln Lys Ile Val Leu Asn Phe Asn Pro His
         35                  40                  45

Phe Glu Ile Glu Lys His Asp Cys Lys Tyr Asp Phe Ile Glu Ile Arg
 50                  55                  60

Asp Gly Asp Ser Glu Ser Ala Asp Leu Leu Gly Lys His Cys Gly Asn
 65                  70                  75                  80

Ile Ala Pro Pro Thr Ile Ile Ser Ser Gly Ser Val Leu Tyr Ile Lys
                 85                  90                  95

Phe Thr Ser Asp Tyr Ala Arg Gln Gly Ala Gly Phe Ser Leu Arg Tyr
         100                 105                 110

Glu Ile Phe Lys Thr Gly Ser Glu Asp Cys Ser Lys Asn Phe Thr Ser
         115                 120                 125

Pro Asn Gly Thr Ile Glu Ser Pro Gly Phe Pro Glu Lys Tyr Pro His
         130                 135                 140

Asn Leu Asp Cys Thr Phe Thr Ile Leu Ala Lys Pro Arg Met Glu Ile
145                 150                 155                 160

Ile Leu Gln Phe Leu Thr Phe Asp Leu Glu His Asp Pro Leu Gln Val
                 165                 170                 175

Gly Glu Gly Asp Cys Lys Tyr Asp Trp Leu Asp Ile Trp Asp Gly Ile
         180                 185                 190

Pro His Val Gly Pro Leu Ile Gly Lys Tyr Cys Gly Thr Lys Thr Pro
         195                 200                 205

Ser Lys Leu Arg Ser Ser Thr Gly Ile Leu Ser Leu Thr Phe His Thr
         210                 215                 220

Asp Met Ala Val Ala Lys Asp Gly Phe Ser Ala Arg Tyr Tyr Leu Ile
225                 230                 235                 240

His Gln Glu Pro Pro Glu Asn Phe Gln Cys Asn Val Pro Leu Gly Met
                 245                 250                 255

Glu Ser Gly Arg Ile Ala Asn Glu Gln Ile Ser Ala Ser Ser Thr Phe
         260                 265                 270

Ser Asp Gly Arg Trp Thr Pro Gln Gln Ser Arg Leu His Gly Asp Asp
         275                 280                 285

Asn Gly Trp Thr Pro Asn Leu Asp Ser Asn Lys Glu Tyr Leu Gln Val
         290                 295                 300

Asp Leu Arg Phe Leu Thr Met Leu Thr Ala Ile Ala Thr Gln Gly Ala
305                 310                 315                 320

Ile Ser Arg Glu Thr Gln Lys Gly Tyr Tyr Val Lys Ser Tyr Lys Leu
                 325                 330                 335

Glu Val Ser Thr Asn Gly Glu Asp Trp Met Val Tyr Arg His Gly Lys
         340                 345                 350

Asn His Lys Ile Phe Gln Ala Asn Asn Asp Ala Thr Glu Val Val Leu
         355                 360                 365

Asn Lys Leu His Met Pro Leu Leu Thr Arg Phe Ile Arg Ile Arg Pro
         370                 375                 380

Gln Thr Trp His Leu Gly Ile Ala Leu Arg Leu Glu Leu Phe Gly Cys
385                 390                 395                 400

Arg Val Thr Asp Ala Pro Cys Ser Asn Met Leu Gly Met Leu Ser Gly
                 405                 410                 415

Leu Ile Ala Asp Thr Gln Ile Ser Ala Ser Ser Thr Arg Glu Tyr Leu
         420                 425                 430

Trp Ser Pro Ser Ala Ala Arg Leu Val Ser Ser Arg Ser Gly Trp Phe
         435                 440                 445
```

```
Pro Arg Asn Pro Gln Ala Gln Pro Gly Glu Glu Trp Leu Gln Val Asp
    450                 455                 460
Leu Gly Thr Pro Lys Thr Val Lys Gly Val Ile Ile Gln Gly Ala Arg
465                 470                 475                 480
Gly Gly Asp Ser Ile Thr Ala Val Glu Ala Arg Ala Phe Val Arg Lys
                485                 490                 495
Phe Lys Val Ser Tyr Ser Leu Asn Gly Lys Asp Trp Glu Tyr Ile Gln
            500                 505                 510
Asp Pro Arg Thr Gln Gln Pro Lys Leu Phe Glu Gly Asn Met His Tyr
        515                 520                 525
Asp Thr Pro Asp Ile Arg Arg Phe Asp Pro Val Pro Ala Gln Tyr Val
    530                 535                 540
Arg Val Tyr Pro Glu Arg Trp Ser Pro Ala Gly Ile Gly Met Arg Leu
545                 550                 555                 560
Glu Val Leu Gly Cys Asp Trp Thr
                565
```

<210> SEQ ID NO 17
<211> LENGTH: 568
<212> TYPE: PRT
<213> ORGANISM: Rattus norvegicus

<400> SEQUENCE: 17

```
Cys Gly Gly Arg Leu Asn Ser Lys Asp Ala Gly Tyr Ile Thr Ser Pro
1               5                   10                  15
Gly Tyr Pro Gln Asp Tyr Pro Ser His Gln Asn Cys Glu Trp Val Val
            20                  25                  30
Tyr Ala Pro Glu Pro Asn Gln Lys Ile Val Leu Asn Phe Asn Pro His
        35                  40                  45
Phe Glu Ile Glu Lys His Asp Cys Lys Tyr Asp Phe Ile Glu Ile Arg
    50                  55                  60
Asp Gly Asp Ser Glu Ser Ala Asp Leu Leu Gly Lys His Cys Gly Asn
65                  70                  75                  80
Ile Ala Pro Pro Thr Ile Ile Ser Ser Gly Ser Val Leu Tyr Ile Lys
                85                  90                  95
Phe Thr Ser Asp Tyr Ala Arg Gln Gly Ala Gly Phe Ser Leu Arg Tyr
            100                 105                 110
Glu Ile Phe Lys Thr Gly Ser Glu Asp Cys Ser Lys Asn Phe Thr Ser
        115                 120                 125
Pro Asn Gly Thr Ile Glu Ser Pro Gly Phe Pro Glu Lys Tyr Pro His
    130                 135                 140
Asn Leu Asp Cys Thr Phe Thr Ile Leu Ala Lys Pro Arg Met Glu Ile
145                 150                 155                 160
Ile Leu Gln Phe Leu Thr Phe Asp Leu Glu His Asp Pro Leu Gln Val
                165                 170                 175
Gly Glu Gly Asp Cys Lys Tyr Asp Trp Leu Asp Ile Trp Asp Gly Ile
            180                 185                 190
Pro His Val Gly Pro Leu Ile Gly Lys Tyr Cys Gly Thr Lys Thr Pro
        195                 200                 205
Ser Lys Leu Arg Ser Ser Thr Gly Ile Leu Ser Leu Thr Phe His Thr
    210                 215                 220
Asp Met Ala Val Ala Lys Asp Gly Phe Ser Ala Arg Tyr Tyr Leu Val
225                 230                 235                 240
His Gln Glu Pro Pro Glu Asn Phe Gln Cys Asn Ala Pro Leu Gly Met
                245                 250                 255
```

```
Glu Ser Gly Arg Ile Ala Asn Glu Gln Ile Ser Ala Ser Ser Thr Phe
            260                 265                 270

Ser Asp Gly Arg Trp Thr Pro Gln Gln Ser Arg Leu His Gly Asp Asp
        275                 280                 285

Asn Gly Trp Thr Pro Asn Val Asp Ser Asn Lys Glu Tyr Leu Gln Val
290                 295                 300

Asp Leu Arg Phe Leu Thr Met Leu Thr Ala Ile Ala Thr Gln Gly Ala
305                 310                 315                 320

Ile Ser Arg Glu Thr Gln Lys Gly Tyr Tyr Val Lys Ser Tyr Lys Leu
            325                 330                 335

Glu Val Ser Thr Asn Gly Glu Asp Trp Met Val Tyr Arg His Gly Lys
        340                 345                 350

Asn His Lys Val Phe Gln Ala Asn Asn Asp Ala Thr Glu Leu Val Leu
                355                 360                 365

Asn Lys Leu His Thr Pro Leu Leu Thr Arg Phe Ile Arg Ile Arg Pro
370                 375                 380

Gln Thr Trp His Leu Gly Ile Ala Leu Arg Leu Glu Leu Phe Gly Cys
385                 390                 395                 400

Arg Val Thr Asp Ala Pro Cys Ser Asn Met Leu Gly Met Leu Ser Gly
                405                 410                 415

Leu Ile Ala Asp Thr Gln Ile Ser Ala Ser Thr Arg Glu Tyr Leu
                420                 425                 430

Trp Ser Pro Ser Ala Ala Arg Leu Val Ser Ser Arg Ser Gly Trp Phe
        435                 440                 445

Pro Arg Asn Pro Gln Ala Gln Pro Gly Glu Glu Trp Leu Gln Val Asp
450                 455                 460

Leu Gly Thr Pro Lys Thr Val Lys Gly Val Ile Ile Gln Gly Ala Arg
465                 470                 475                 480

Gly Gly Asp Ser Ile Thr Ala Met Glu Ala Arg Ala Phe Val Arg Lys
            485                 490                 495

Phe Lys Val Ser Tyr Ser Leu Asn Gly Lys Asp Trp Glu Tyr Ile Gln
        500                 505                 510

Asp Pro Arg Thr Gln Gln Pro Lys Leu Phe Glu Gly Asn Met His Tyr
        515                 520                 525

Asp Thr Pro Asp Ile Arg Arg Phe Glu Pro Ile Pro Ala Gln Tyr Val
        530                 535                 540

Arg Val Tyr Pro Glu Arg Trp Ser Pro Ala Gly Ile Gly Met Arg Leu
545                 550                 555                 560

Glu Val Leu Gly Cys Asp Trp Thr
                565

<210> SEQ ID NO 18
<211> LENGTH: 568
<212> TYPE: PRT
<213> ORGANISM: Gallus domesticus

<400> SEQUENCE: 18

Cys Gly Gly Arg Leu Asn Ser Lys Asp Ala Gly Tyr Ile Thr Ser Pro
1               5                   10                  15

Gly Tyr Pro Asn Asp Tyr Pro Ser His Gln Asn Cys Glu Trp Val Ile
            20                  25                  30

Tyr Ala Pro Glu Pro Asn Gln Lys Ile Ile Leu Asn Phe Asn Pro His
        35                  40                  45

Phe Glu Ile Glu Lys His Asp Cys Lys Tyr Asp Phe Ile Glu Ile Arg
    50                  55                  60
```

-continued

```
Asp Gly Asp Ser Glu Ala Ala Asp Leu Leu Gly Lys His Cys Gly Asn
 65                  70                  75                  80

Ile Ala Pro Pro Thr Ile Ile Ser Ser Gly Ser Ser Leu Tyr Ile Lys
                 85                  90                  95

Phe Thr Ser Asp Tyr Ala Arg Gln Gly Ala Gly Phe Ser Leu Arg Tyr
            100                 105                 110

Glu Ile Phe Lys Thr Gly Ser Glu Asp Cys Ser Lys Asn Phe Thr Ala
            115                 120                 125

Ser Asn Gly Thr Ile Glu Ser Pro Gly Phe Pro Asp Lys Tyr Pro His
        130                 135                 140

Asn Leu Asp Cys Val Phe Thr Ile Ile Ala Lys Pro Lys Thr Glu Ile
145                 150                 155                 160

Leu Leu His Phe Val Thr Phe Asp Leu Glu His Asp Pro Leu Gln Ala
                165                 170                 175

Gly Glu Gly Asp Cys Lys Tyr Asp Trp Leu Asp Ile Trp Asp Gly Ile
            180                 185                 190

Pro Gln Val Gly Pro Leu Ile Gly Arg Tyr Cys Gly Thr Lys Met Pro
            195                 200                 205

Ser Asp Ile Arg Ser Thr Thr Gly Val Leu Ser Leu Thr Phe His Thr
210                 215                 220

Asp Leu Ala Val Ala Lys Asp Gly Phe Ser Ala Gln Tyr Tyr Leu Ile
225                 230                 235                 240

Gln Gln Glu Val Pro Glu Asn Phe Gln Cys Asn Val Pro Leu Gly Met
                245                 250                 255

Glu Ser Gly Arg Ile Ser Asn Met Gln Ile Ser Ala Ser Ser Thr Tyr
            260                 265                 270

Ser Asp Gly Arg Trp Thr Pro Gln Gln Ser Arg Leu Asn Ser Asp Asp
        275                 280                 285

Asn Gly Trp Thr Pro Asn Val Asp Ser Asn Lys Glu Tyr Leu Gln Val
        290                 295                 300

Asp Leu His Phe Leu Thr Val Leu Thr Ala Ile Ala Thr Gln Gly Ala
305                 310                 315                 320

Ile Ser Arg Glu Thr Gln Asn Gly Tyr Tyr Val Arg Thr Tyr Lys Leu
                325                 330                 335

Glu Val Ser Thr Asn Gly Glu Asp Trp Met Val Tyr Arg His Gly Lys
            340                 345                 350

Asn His Lys Thr Phe Gln Ala Asn Glu Asp Ala Thr Glu Val Val Leu
        355                 360                 365

Asn Lys Ile His Ser Pro Val Leu Thr Arg Phe Val Arg Ile Arg Pro
370                 375                 380

Gln Ser Trp His Asn Gly Ile Ala Leu Arg Leu Glu Leu Tyr Gly Cys
385                 390                 395                 400

Arg Ile Thr Asp Ser Pro Cys Ser Asn Leu Leu Gly Met Leu Ser Gly
                405                 410                 415

Leu Ile Pro Asp Ser Gln Ile Ser Ala Ser Ser Ile Arg Gly Tyr Asp
            420                 425                 430

Trp Ser Pro Ser Met Ala Arg Leu Val Ser Ser Arg Ser Gly Trp Phe
        435                 440                 445

Pro Arg Ile Pro Gln Ala Gln Pro Gly Glu Glu Trp Leu Gln Val Asp
        450                 455                 460

Leu Gly Val Pro Lys Asn Val Lys Gly Val Ile Ile Gln Gly Ala Arg
465                 470                 475                 480

Gly Gly Asp Ser Val Thr Thr Thr Glu Ser Arg Ser Phe Val Lys Lys
```

```
                        485                 490                 495
Phe Lys Val Ala Tyr Ser Met Asn Gly Lys Asp Trp Glu Phe Ile Gln
            500                 505                 510

Asp Pro Lys Thr Met Gln Ala Lys Leu Phe Glu Gly Asn Ile His Tyr
        515                 520                 525

Asp Ile Pro Glu Ile Arg Arg Phe Asp Pro Val Pro Ala Gln Tyr Val
    530                 535                 540

Arg Val His Pro Glu Arg Trp Ser Pro Ala Gly Ile Gly Met Arg Leu
545                 550                 555                 560

Glu Val Leu Gly Cys Asp Trp Thr
                565

<210> SEQ ID NO 19
<211> LENGTH: 568
<212> TYPE: PRT
<213> ORGANISM: Xenopus laevis

<400> SEQUENCE: 19

Cys Gly Gly Arg Leu Asn Ala Lys Asp Ala Gly Tyr Ile Thr Ser Pro
1               5                  10                  15

Gly Tyr Pro Asn Asp Tyr Pro Pro His Gln Asn Cys Glu Trp Ile Ile
            20                  25                  30

Ser Ala Pro Glu Pro Asn Gln Lys Ile Val Leu Asn Phe Asn Pro His
        35                  40                  45

Phe Asp Ile Glu Lys His Asp Cys Lys Tyr Asp Phe Ile Glu Ile Arg
    50                  55                  60

Asp Gly Asp Ser Glu Ser Ala Glu Leu Leu Gly Lys His Cys Gly Asn
65                  70                  75                  80

Ile Ala Pro Ser Thr Ile Thr Ser Ser Gly Ser Gln Met Tyr Ile Arg
                85                  90                  95

Phe Thr Ser Asp Tyr Ala Arg Gln Gly Ala Gly Phe Ser Leu Arg Tyr
            100                 105                 110

Glu Ile Phe Lys Thr Gly Ser Glu Asp Cys Ser Lys Asn Phe Thr Asn
        115                 120                 125

Ser Asn Gly Thr Ile Glu Ser Pro Gly Phe Pro Asp Lys Tyr Pro His
    130                 135                 140

Asn Leu Asp Cys Val Phe Thr Ile Val Ala Lys Pro Lys Met Glu Ile
145                 150                 155                 160

Ile Leu Gln Phe His Thr Phe Asp Leu Glu His Asp Pro Leu Gln Val
                165                 170                 175

Gly Glu Gly Asp Cys Lys Tyr Asp Trp Leu Asp Ile Trp Asp Gly Val
            180                 185                 190

Pro Ser Val Gly Pro Leu Ile Gly Arg Tyr Cys Gly Thr Lys Thr Pro
        195                 200                 205

Ser Glu Ile Arg Ser Ser Thr Gly Ile Leu Ser Leu Thr Phe His Thr
    210                 215                 220

Asp Met Ala Val Ala Lys Asp Gly Phe Ser Ala Arg Tyr Tyr Leu Ala
225                 230                 235                 240

Pro Gln Glu Val Pro Glu Thr Phe Gln Cys Asn Val Pro Leu Gly Met
                245                 250                 255

Glu Ser Gly Arg Ile Ser Asn Glu Gln Ile Thr Ala Ser Ser Thr Tyr
            260                 265                 270

Ser Asp Gly Arg Trp Thr Ala Gln Gln Ser Arg Leu Asn Ser Asp Asp
        275                 280                 285

Asn Gly Trp Thr Pro Asn Val Asp Thr Asn Arg Glu Tyr Leu Gln Ile
```

```
                290                 295                 300
Asp Leu Arg Phe Leu Phe Leu Thr Ala Ile Ala Thr Gln Gly Ala
305                 310                 315                 320

Ile Ser Arg Glu Thr Gln Thr Pro Tyr Tyr Val Lys Ser Tyr Lys Leu
                325                 330                 335

Glu Val Ser Thr Asn Gly Glu Asp Trp Met Val Phe Arg His Gly Lys
                340                 345                 350

Asn His Lys Ile Phe Gln Gly Asn Thr Asp Pro Thr Glu Val Val Leu
                355                 360                 365

Asn Lys Ile His Gln Pro Val Leu Ala Arg Phe Ile Arg Phe Arg Pro
370                 375                 380

Gln Thr Trp Asp Thr Gly Ile Ala Met Arg Val Glu Leu Tyr Gly Cys
385                 390                 395                 400

Gln Ile Thr Asp Ser Pro Cys Ser Asn Met Leu Gly Met Met Ser Gly
                405                 410                 415

Leu Ile Ser Asp Ser Gln Ile Thr Ala Ser Ser Thr Arg Glu Tyr Leu
                420                 425                 430

Trp Ser Ser Gly Val Ala Arg Leu Val Ser Ser Arg Ser Gly Trp Tyr
435                 440                 445

Thr His Ile Ser Pro Gly Gln Ile Gly Lys Glu Trp Leu Gln Val Asp
450                 455                 460

Leu Gly Thr Val Lys Thr Val Arg Gly Val Ile Ile Gln Gly Ala Arg
465                 470                 475                 480

Gly Gly Asp Ser Leu Pro Thr Thr Glu Asn Arg Ala Phe Val Arg Lys
                485                 490                 495

Phe Lys Val Ala His Ser Leu Asn Gly Asn Asp Trp Glu Tyr Ile Leu
                500                 505                 510

Asp Ser Lys Thr Glu Gln Ala Lys Gln Phe Glu Gly Asn Met His Tyr
                515                 520                 525

Asp Thr Pro Glu Val Arg Arg Phe Glu Pro Val Ala Ala Gln Phe Val
                530                 535                 540

Arg Val Tyr Pro Glu Arg Trp Ser Pro Ala Gly Met Gly Met Arg Met
545                 550                 555                 560

Glu Val Leu Gly Cys Asp Arg Gln
                565

<210> SEQ ID NO 20
<211> LENGTH: 567
<212> TYPE: PRT
<213> ORGANISM: Danio rerio

<400> SEQUENCE: 20

Cys Gly Gly Ser Phe Asp Ala Ser Asp Ala Gly Tyr Ile Thr Thr Pro
1               5                   10                  15

Gly Tyr Pro Leu Glu Tyr Pro Pro His Gln Asn Cys Arg Trp Val Ile
                20                  25                  30

Thr Ala Pro Glu Pro Ser Gln Arg Ile Val Leu Asn Phe Asn Pro His
                35                  40                  45

Phe Glu Leu Glu Lys Leu Asp Cys Arg Tyr Asp Phe Ile Glu Ile Arg
                50                  55                  60

Asp Gly Asn Ser Asp Gly Ala Asp Leu Leu Gly Arg His Cys Ser Asn
65                  70                  75                  80

Ile Ala Pro Pro Ala Ile Ile Ser Ser Gly Pro Val Leu His Ile Lys
                85                  90                  95

Phe Val Ser Asp Tyr Ala His Gln Gly Ala Gly Phe Ser Leu Arg Tyr
```

```
                100              105              110
Glu Ile Tyr Lys Thr Gly Ser Asp Cys Ser Arg Asn Phe Thr Ser Pro
            115              120              125
Ser Gly Val Ile Glu Ser Pro Gly Phe Pro Asp Lys Tyr Pro His Asn
130              135              140
Leu Glu Cys Thr Phe Ile Ile Val Val Pro Pro His Met Asp Val Thr
145              150              155              160
Leu Thr Phe Leu Thr Phe Asp Leu Glu Asn Asp Pro Leu Gln Gly Ser
            165              170              175
Glu Gly Glu Cys Lys Tyr Asp Trp Leu Glu Val Trp Asp Gly Leu Pro
            180              185              190
Gln Val Gly Pro Leu Ile Gly Arg His Cys Gly Thr Lys Ile Pro Ser
            195              200              205
Glu Ile Gln Ser Ser Thr Gly Ile Leu Ser Leu Ser Phe His Thr Asp
            210              215              220
Met Ala Val Ala Lys Asp Gly Phe Ser Ala Arg Tyr Asn Met Thr Leu
225              230              235              240
Lys Glu Val Asn Asp Asn Phe His Cys Ser Asn Asp Leu Gly Met Glu
            245              250              255
Ser Gly Lys Ile Ser Asp Asp Gln Ile Ser Ala Ser Ser Ser Phe Tyr
            260              265              270
Asp Gly Arg Trp Ser Pro Arg Gln Ala Arg Leu Asn Phe Asp Asp Asn
            275              280              285
Ala Trp Thr Pro Asn Glu Asp Ser Asn Lys Glu Tyr Ile Gln Val Asp
            290              295              300
Leu His Phe Leu Lys Val Leu Thr Gly Ile Ala Thr Gln Gly Ala Val
305              310              315              320
Ser Lys Glu Thr His Lys Ser Tyr Phe Val Thr Thr Phe Lys Leu Glu
            325              330              335
Val Ser Thr Asn Gly Glu Asp Trp Met Ile Tyr Arg Phe Gly Lys Asn
            340              345              350
His Lys Val Phe His Ala Asn Ala Asp Ala Ser Glu Val Val Leu Asn
            355              360              365
Arg Ile Pro Gln Pro Val Leu Ala Arg Phe Val Arg Ile Arg Pro Gln
370              375              380
Ser Trp Lys Asn Gly Ile Ala Leu Arg Phe Glu Leu Tyr Gly Cys Gln
385              390              395              400
Ile Thr Asp Ala Pro Cys Ser Glu Met Gln Gly Met Leu Ser Gly Leu
            405              410              415
Ile Pro Asp Ser Gln Ile Ser Ala Ser Ser Met Arg Asp Ile His Gly
            420              425              430
Ala Thr Gly Ala Ala Arg Leu Val Ala Ser Arg Ser Gly Trp Phe Pro
            435              440              445
Ser Pro Thr Gln Ala Val Ala Gly Glu Glu Trp Leu Gln Val Asp Leu
            450              455              460
Gly Val Pro Lys Thr Val Arg Gly Ile Ile Gln Gly Ala Arg Gly
465              470              475              480
Val Asp Ser Ser Thr Ser Ala Glu Asn Arg Ala Phe Val Arg Lys Tyr
            485              490              495
Lys Leu Ala His Ser Leu Asn Gly Lys Asp Leu Ser Tyr Ile Ile Asp
            500              505              510
Pro Lys Thr Asn Leu Pro Lys Ile Phe Glu Gly Asn Thr His Tyr Asp
            515              520              525
```

```
Thr Pro Glu Ile Arg Arg Phe Asp Glu Ile Val Ala Gln Phe Ile Arg
        530                 535                 540

Val Tyr Pro Glu Arg Trp Ser Pro Ala Gly Ile Gly Met Arg Met Glu
545                 550                 555                 560

Ile Leu Ala Cys Asp Leu Pro
                565

<210> SEQ ID NO 21
<211> LENGTH: 560
<212> TYPE: PRT
<213> ORGANISM: Homo sapiens

<400> SEQUENCE: 21

Cys Gly Asp Thr Ile Lys Ile Glu Ser Pro Gly Tyr Leu Thr Ser Pro
1               5                   10                  15

Gly Tyr Pro His Ser Tyr His Pro Ser Glu Lys Cys Glu Trp Leu Ile
                20                  25                  30

Gln Ala Pro Asp Pro Tyr Gln Arg Ile Met Ile Asn Phe Asn Pro His
                35                  40                  45

Phe Asp Leu Glu Asp Arg Asp Cys Lys Tyr Asp Tyr Val Glu Val Phe
    50                  55                  60

Asp Gly Glu Asn Glu Asn Gly His Phe Arg Gly Lys Phe Cys Gly Lys
65              70                  75                  80

Ile Ala Pro Pro Pro Val Val Ser Ser Gly Pro Phe Leu Phe Ile Arg
                85                  90                  95

Phe Val Ser Asp Tyr Glu Thr His Gly Ala Gly Phe Ser Ile Arg Tyr
                100                 105                 110

Glu Ile Phe Lys Arg Gly Pro Glu Cys Ser Gln Asn Tyr Thr Thr Pro
                115                 120                 125

Ser Gly Val Ile Lys Ser Pro Gly Phe Pro Asp Lys Tyr Pro Asn Ser
    130                 135                 140

Leu Glu Cys Thr Tyr Ile Val Phe Ala Pro Lys Met Ser Glu Ile Ile
145                 150                 155                 160

Leu Glu Phe Glu Ser Phe Asp Leu Glu Pro Asp Ser Asn Pro Pro Gly
                165                 170                 175

Gly Met Phe Cys Arg Tyr Asp Arg Leu Glu Ile Trp Asp Gly Phe Pro
                180                 185                 190

Asp Val Gly Pro His Ile Gly Arg Tyr Cys Gly Gln Lys Thr Pro Gly
            195                 200                 205

Arg Ile Arg Ser Ser Ser Gly Ile Leu Ser Met Val Phe Tyr Thr Asp
    210                 215                 220

Ser Ala Ile Ala Lys Glu Gly Phe Ser Ala Asn Tyr Ser Val Leu Gln
225                 230                 235                 240

Ser Ser Val Ser Glu Asp Phe Lys Cys Met Glu Ala Leu Gly Met Glu
                245                 250                 255

Ser Gly Glu Ile His Ser Asp Gln Ile Thr Ala Ser Ser Gln Tyr Ser
                260                 265                 270

Thr Asn Trp Ser Ala Glu Arg Ser Arg Leu Asn Tyr Pro Asp Asn Gly
            275                 280                 285

Trp Thr Pro Gly Glu Asp Ser Tyr Arg Glu Trp Ile Gln Val Asp Leu
    290                 295                 300

Gly Leu Leu Arg Phe Val Thr Ala Val Gly Thr Gln Gly Ala Ile Ser
305                 310                 315                 320

Lys Glu Thr Lys Lys Lys Tyr Tyr Val Lys Thr Tyr Lys Ile Asp Val
                325                 330                 335
```

Ser Ser Asn Gly Glu Asp Trp Ile Thr Ile Lys Glu Gly Asn Lys Pro
            340                 345                 350

Val Leu Phe Gln Gly Asn Thr Asn Pro Thr Asp Val Val Ala Val
            355                 360                 365

Phe Pro Lys Pro Leu Ile Thr Arg Phe Val Arg Ile Lys Pro Ala Thr
370                 375                 380

Trp Glu Thr Gly Ile Ser Met Arg Phe Glu Val Tyr Gly Cys Lys Ile
385                 390                 395                 400

Thr Asp Tyr Pro Cys Ser Gly Met Leu Gly Met Val Ser Gly Leu Ile
            405                 410                 415

Ser Asp Ser Gln Ile Thr Ala Ser Asn Gln Gly Asp Arg Asn Trp Met
            420                 425                 430

Pro Glu Asn Ile Arg Leu Val Thr Ser Arg Ser Gly Trp Ala Leu Pro
            435                 440                 445

Pro Ala Pro His Ser Tyr Ile Asn Glu Trp Leu Gln Ile Asp Leu Gly
            450                 455                 460

Glu Glu Lys Ile Val Arg Gly Ile Ile Gln Gly Lys His Arg
465                 470                 475                 480

Glu Asn Lys Val Phe Met Arg Lys Phe Lys Ile Gly Tyr Ser Asn Asn
            485                 490                 495

Gly Ser Asp Trp Lys Met Ile Met Asp Asp Ser Lys Arg Lys Ala Lys
            500                 505                 510

Ser Phe Glu Gly Asn Asn Asn Tyr Asp Thr Pro Glu Leu Arg Thr Phe
            515                 520                 525

Pro Ala Leu Ser Thr Arg Phe Ile Arg Ile Tyr Pro Glu Arg Ala Thr
            530                 535                 540

His Gly Gly Leu Gly Leu Arg Met Glu Leu Leu Gly Cys Glu Val Glu
545                 550                 555                 560

<210> SEQ ID NO 22
<211> LENGTH: 560
<212> TYPE: PRT
<213> ORGANISM: Rattus norvegicus

<400> SEQUENCE: 22

Cys Gly Gly Thr Ile Lys Ile Glu Asn Pro Gly Tyr Leu Thr Ser Pro
1               5                   10                  15

Gly Tyr Pro His Ser Tyr His Pro Ser Glu Lys Cys Glu Trp Leu Ile
            20                  25                  30

Gln Ala Pro Glu Pro Tyr Gln Arg Ile Met Ile Asn Phe Asn Pro His
            35                  40                  45

Phe Asp Leu Glu Asp Arg Asp Cys Lys Tyr Asp Tyr Val Glu Val Ile
    50                  55                  60

Asp Gly Glu Asn Glu Gly Gly Arg Leu Trp Gly Lys Phe Cys Gly Lys
65                  70                  75                  80

Ile Ala Pro Ser Pro Val Val Ser Gly Pro Phe Leu Phe Ile Arg
                85                  90                  95

Phe Val Ser Asp Tyr Glu Thr His Gly Ala Gly Phe Ser Ile Arg Tyr
            100                 105                 110

Glu Ile Phe Lys Arg Gly Pro Glu Cys Ser Gln Asn Tyr Thr Ala Pro
            115                 120                 125

Thr Gly Val Ile Lys Ser Pro Gly Phe Pro Glu Lys Tyr Pro Asn Ser
        130                 135                 140

Leu Glu Cys Thr Tyr Ile Ile Phe Ala Pro Lys Met Ser Glu Ile Ile
145                 150                 155                 160

```
Leu Glu Phe Glu Ser Phe Asp Leu Glu Gln Asp Ser Asn Pro Pro Gly
            165                 170                 175

Gly Val Phe Cys Arg Tyr Asp Arg Leu Glu Ile Trp Asp Gly Phe Pro
        180                 185                 190

Glu Val Gly Pro His Ile Gly Arg Tyr Cys Gly Gln Lys Thr Pro Gly
    195                 200                 205

Arg Ile Arg Ser Ser Ser Gly Ile Leu Ser Met Val Phe Tyr Thr Asp
    210                 215                 220

Ser Ala Ile Ala Lys Glu Gly Phe Ser Ala Asn Tyr Ser Val Leu Gln
225                 230                 235                 240

Ser Ser Ile Ser Glu Asp Phe Lys Cys Met Glu Ala Leu Gly Met Glu
            245                 250                 255

Ser Gly Glu Ile His Ser Asp Gln Ile Thr Ala Ser Ser Gln Tyr Gly
            260                 265                 270

Thr Asn Trp Ser Val Glu Arg Ser Arg Leu Asn Tyr Pro Glu Asn Gly
            275                 280                 285

Trp Thr Pro Gly Glu Asp Ser Tyr Arg Glu Trp Ile Gln Val Asp Leu
    290                 295                 300

Gly Leu Leu Arg Phe Val Thr Ala Val Gly Thr Gln Gly Ala Ile Ser
305                 310                 315                 320

Lys Glu Thr Lys Lys Lys Tyr Tyr Val Lys Thr Tyr Arg Val Asp Ile
                325                 330                 335

Ser Ser Asn Gly Glu Asp Trp Ile Thr Leu Lys Glu Gly Asn Lys Ala
            340                 345                 350

Ile Ile Phe Gln Gly Asn Thr Asn Pro Thr Asp Val Val Phe Gly Val
            355                 360                 365

Phe Pro Lys Pro Leu Ile Thr Arg Phe Val Arg Ile Lys Pro Ala Ser
370                 375                 380

Trp Glu Thr Gly Ile Ser Met Arg Phe Glu Val Tyr Gly Cys Lys Ile
385                 390                 395                 400

Thr Asp Tyr Pro Cys Ser Gly Met Leu Gly Met Val Ser Gly Leu Ile
                405                 410                 415

Ser Asp Ser Gln Ile Thr Ala Ser Asn Gln Gly Asp Arg Asn Trp Met
            420                 425                 430

Pro Glu Asn Ile Arg Leu Val Thr Ser Arg Thr Gly Trp Ala Leu Pro
                435                 440                 445

Pro Ser Pro His Pro Tyr Ile Asn Glu Trp Leu Gln Val Asp Leu Gly
            450                 455                 460

Asp Glu Lys Ile Val Arg Gly Val Ile Ile Gln Gly Gly Lys His Arg
465                 470                 475                 480

Glu Asn Lys Val Phe Met Arg Lys Phe Lys Ile Ala Tyr Ser Asn Asn
                485                 490                 495

Gly Ser Asp Trp Lys Met Ile Met Asp Asp Ser Lys Arg Lys Ala Lys
            500                 505                 510

Ser Phe Glu Gly Asn Asn Asn Tyr Asp Thr Pro Glu Leu Arg Ala Phe
    515                 520                 525

Thr Pro Leu Ser Thr Arg Phe Ile Arg Ile Tyr Pro Glu Arg Ala Thr
    530                 535                 540

His Ser Gly Leu Gly Leu Arg Met Glu Leu Leu Gly Cys Glu Val Glu
545                 550                 555                 560

<210> SEQ ID NO 23
<211> LENGTH: 560
<212> TYPE: PRT
<213> ORGANISM: Mus musculus
```

<400> SEQUENCE: 23

```
Cys Gly Gly Thr Ile Lys Ile Glu Asn Pro Gly Tyr Leu Thr Ser Pro
1               5                   10                  15

Gly Tyr Pro His Ser Tyr His Pro Ser Glu Lys Cys Glu Trp Leu Ile
            20                  25                  30

Gln Ala Pro Glu Pro Tyr Gln Arg Ile Ile Ile Asn Phe Asn Pro His
        35                  40                  45

Phe Asp Leu Glu Asp Arg Asp Cys Lys Tyr Asp Tyr Val Glu Val Ile
50                  55                  60

Asp Gly Glu Asn Glu Gly Arg Leu Trp Gly Lys Phe Cys Gly Lys
65                  70                  75                  80

Ile Ala Pro Ser Pro Val Val Ser Ser Gly Pro Phe Leu Phe Ile Arg
                85                  90                  95

Phe Val Ser Asp Tyr Glu Thr His Gly Ala Gly Phe Ser Ile Arg Tyr
            100                 105                 110

Glu Ile Phe Lys Arg Gly Pro Glu Cys Ser Gln Asn Tyr Thr Ala Pro
            115                 120                 125

Thr Gly Val Ile Lys Ser Pro Gly Phe Pro Glu Lys Tyr Pro Asn Cys
    130                 135                 140

Leu Glu Cys Thr Tyr Ile Ile Phe Ala Pro Lys Met Ser Glu Ile Ile
145                 150                 155                 160

Leu Glu Phe Glu Ser Phe Asp Leu Glu Gln Asp Ser Asn Pro Pro Gly
                165                 170                 175

Gly Met Phe Cys Arg Tyr Asp Arg Leu Glu Ile Trp Asp Gly Phe Pro
            180                 185                 190

Glu Val Gly Pro His Ile Gly Arg Tyr Cys Gly Gln Lys Thr Pro Gly
        195                 200                 205

Arg Ile Arg Ser Ser Ser Gly Val Leu Ser Met Val Phe Tyr Thr Asp
210                 215                 220

Ser Ala Ile Ala Lys Glu Gly Phe Ser Ala Asn Tyr Ser Val Leu Gln
225                 230                 235                 240

Ser Ser Ile Ser Glu Asp Phe Lys Cys Met Glu Ala Leu Gly Met Glu
                245                 250                 255

Ser Gly Glu Ile His Ser Asp Gln Ile Thr Ala Ser Ser Gln Tyr Gly
            260                 265                 270

Thr Asn Trp Ser Val Glu Arg Ser Arg Leu Asn Tyr Pro Glu Asn Gly
        275                 280                 285

Trp Thr Pro Gly Glu Asp Ser Tyr Lys Glu Trp Ile Gln Val Asp Leu
290                 295                 300

Gly Leu Leu Arg Phe Val Thr Ala Val Gly Thr Gln Gly Ala Ile Ser
305                 310                 315                 320

Lys Glu Thr Lys Lys Lys Tyr Tyr Val Lys Thr Tyr Arg Val Asp Ile
                325                 330                 335

Ser Ser Asn Gly Glu Asp Trp Ile Ser Leu Lys Glu Gly Asn Lys Ala
            340                 345                 350

Ile Ile Phe Gln Gly Asn Thr Asn Pro Thr Asp Val Val Leu Gly Val
        355                 360                 365

Phe Ser Lys Pro Leu Ile Thr Arg Phe Val Arg Ile Lys Pro Val Ser
370                 375                 380

Trp Glu Thr Gly Ile Ser Met Arg Phe Glu Val Tyr Gly Cys Lys Ile
385                 390                 395                 400

Thr Asp Tyr Pro Cys Ser Gly Met Leu Gly Met Val Ser Gly Leu Ile
                405                 410                 415
```

```
Ser Asp Ser Gln Ile Thr Ala Ser Asn Gln Ala Asp Arg Asn Trp Met
            420                 425                 430

Pro Glu Asn Ile Arg Leu Val Thr Ser Arg Thr Gly Trp Ala Leu Pro
            435                 440                 445

Pro Ser Pro His Pro Tyr Thr Asn Glu Trp Leu Gln Val Asp Leu Gly
            450                 455                 460

Asp Glu Lys Ile Val Arg Gly Val Ile Ile Gln Gly Lys His Arg
465                 470                 475                 480

Glu Asn Lys Val Phe Met Arg Lys Phe Lys Ile Ala Tyr Ser Asn Asn
                485                 490                 495

Gly Ser Asp Trp Lys Thr Ile Met Asp Asp Ser Lys Arg Lys Ala Lys
                500                 505                 510

Ser Phe Glu Gly Asn Asn Tyr Asp Thr Pro Glu Leu Arg Thr Phe
                515                 520                 525

Ser Pro Leu Ser Thr Arg Phe Ile Arg Ile Tyr Pro Glu Arg Ala Thr
            530                 535                 540

His Ser Gly Leu Gly Leu Arg Met Glu Leu Leu Gly Cys Glu Val Glu
545                 550                 555                 560

<210> SEQ ID NO 24
<211> LENGTH: 560
<212> TYPE: PRT
<213> ORGANISM: Gallus domesticus

<400> SEQUENCE: 24

Cys Gly Asp Thr Ile Lys Ile Leu Ser Pro Gly Tyr Leu Thr Ser Pro
1               5                   10                  15

Gly Tyr Pro Gln Ser Tyr His Pro Ser Gln Lys Cys Glu Trp Leu Ile
                20                  25                  30

Gln Ala Pro Glu Pro Tyr Gln Arg Ile Met Ile Asn Phe Asn Pro His
            35                  40                  45

Phe Asp Leu Glu Asp Arg Asp Cys Lys Tyr Asp Tyr Val Glu Val Ile
50                  55                  60

Asp Gly Asp Asn Ala Glu Gly Arg Leu Trp Gly Lys Tyr Cys Gly Lys
65                  70                  75                  80

Ile Ala Pro Pro Leu Val Ser Ser Gly Pro Tyr Leu Phe Ile Arg
                85                  90                  95

Phe Val Ser Asp Tyr Glu Thr His Gly Ala Gly Phe Ser Ile Arg Tyr
            100                 105                 110

Glu Ile Phe Lys Arg Gly Pro Glu Cys Ser Arg Asn Phe Thr Ser Ser
            115                 120                 125

Ser Gly Met Ile Lys Ser Pro Gly Phe Pro Glu Lys Tyr Pro Asn Ser
            130                 135                 140

Leu Glu Cys Thr Tyr Ile Ile Phe Ala Pro Lys Met Ser Glu Ile Ile
145                 150                 155                 160

Leu Glu Phe Glu Ser Phe Glu Leu Glu Pro Asp Ser Asn Thr Pro Gly
                165                 170                 175

Gly Ala Phe Cys Arg Tyr Asp Arg Leu Glu Ile Trp Asp Gly Phe Pro
            180                 185                 190

Asp Val Gly Pro His Ile Gly Arg Tyr Cys Gly Gln Asn Asn Pro Gly
            195                 200                 205

Arg Val Arg Ser Ser Thr Gly Ile Leu Ser Met Val Phe Tyr Thr Asp
            210                 215                 220

Ser Ala Ile Ala Lys Glu Gly Phe Ser Ala Asn Tyr Ser Val Ser Gln
225                 230                 235                 240
```

```
Ser Ser Val Ser Glu Asp Phe Gln Cys Met Glu Pro Leu Gly Met Glu
            245                 250                 255

Ser Gly Glu Ile His Ser Asp Gln Ile Thr Val Ser Ser Gln Tyr Ser
            260                 265                 270

Ala Ile Trp Ser Ser Glu Arg Ser Arg Leu Asn Tyr Pro Glu Asn Gly
            275                 280                 285

Trp Thr Pro Gly Glu Asp Ser Val Arg Glu Trp Ile Gln Val Asp Leu
            290                 295                 300

Gly Leu Leu Arg Phe Val Ser Val Gly Thr Gln Gly Ala Ile Ser
305                 310                 315                 320

Lys Glu Thr Lys Lys Glu Tyr Tyr Leu Lys Thr Tyr Arg Val Asp Val
                    325                 330                 335

Ser Ser Asn Gly Glu Asp Trp Ile Thr Leu Lys Glu Gly Asn Lys Pro
                340                 345                 350

Val Val Phe Gln Gly Asn Ser Asn Pro Thr Asp Val Val Tyr Arg Pro
                355                 360                 365

Phe Pro Lys Pro Val Leu Thr Arg Phe Val Arg Ile Lys Pro Val Ser
            370                 375                 380

Trp Glu Asn Gly Val Ser Leu Arg Phe Glu Val Tyr Gly Cys Lys Ile
385                 390                 395                 400

Thr Asp Tyr Pro Cys Ser Gly Met Leu Gly Met Val Ser Gly Leu Ile
                405                 410                 415

Pro Asp Ser Gln Ile Thr Ala Ser Thr Gln Val Asp Arg Asn Trp Ile
            420                 425                 430

Pro Glu Asn Ala Arg Leu Ile Thr Ser Arg Ser Gly Trp Ala Leu Pro
            435                 440                 445

Pro Thr Thr His Pro Tyr Thr Asn Glu Trp Leu Gln Ile Asp Leu Gly
            450                 455                 460

Glu Glu Lys Ile Val Arg Gly Ile Ile Val Gln Gly Gly Lys His Arg
465                 470                 475                 480

Glu Asn Lys Val Phe Met Lys Lys Phe Lys Ile Gly Tyr Ser Asn Asn
                485                 490                 495

Gly Ser Asp Trp Lys Met Ile Met Asp Ser Ser Lys Lys Lys Ile Lys
            500                 505                 510

Thr Phe Glu Gly Asn Thr Asn Tyr Asp Thr Pro Glu Leu Arg Thr Phe
            515                 520                 525

Glu Pro Val Ser Thr Arg Ile Ile Arg Val Tyr Pro Glu Arg Ala Thr
            530                 535                 540

His Ala Gly Leu Gly Leu Arg Met Glu Leu Leu Gly Cys Glu Leu Glu
545                 550                 555                 560

<210> SEQ ID NO 25
<211> LENGTH: 561
<212> TYPE: PRT
<213> ORGANISM: Xenopus laevis

<400> SEQUENCE: 25

Cys Gly Asp Thr Ile Lys Ile Thr Ser Pro Ser Tyr Leu Thr Ser Ala
1               5                   10                  15

Gly Tyr Pro His Ser Tyr Pro Pro Ser Gln Arg Cys Glu Trp Leu Ile
                20                  25                  30

Gln Ala Pro Glu His Tyr Gln Arg Ile Met Ile Asn Phe Asn Pro His
            35                  40                  45

Phe Asp Leu Glu Asp Arg Glu Cys Lys Tyr Asp Tyr Val Glu Val Ile
50                  55                  60
```

```
Asp Gly Asp Asn Ala Asn Gly Gln Ile Leu Gly Lys Tyr Cys Gly Lys
 65                  70                  75                  80

Ile Ala Pro Ser Pro Leu Val Ser Thr Gly Pro Ser Ile Phe Ile Arg
                 85                  90                  95

Phe Val Ser Asp Tyr Glu Thr Pro Gly Ala Gly Phe Ser Ile Arg Tyr
            100                 105                 110

Glu Ile Phe Lys Arg Gly Pro Glu Cys Ser Arg Asn Phe Thr Ser Ser
        115                 120                 125

Asn Gly Val Ile Lys Ser Pro Lys Tyr Pro Glu Lys Tyr Pro Asn Ala
    130                 135                 140

Leu Glu Cys Thr Tyr Ile Ile Phe Ala Pro Lys Met Gln Glu Ile Val
145                 150                 155                 160

Leu Glu Phe Glu Ser Phe Glu Leu Glu Ala Asp Ser Asn Ala Pro Gly
                165                 170                 175

Gly Gln Thr Cys Arg Tyr Asp Trp Leu Gly Ile Trp Asp Gly Phe Pro
            180                 185                 190

Gly Val Gly Pro His Ile Gly Arg Tyr Cys Gly Gln Asn Thr Pro Gly
        195                 200                 205

Arg Val Arg Ser Phe Thr Gly Ile Leu Ser Met Ile Phe His Thr Asp
    210                 215                 220

Ser Ala Ile Ala Lys Glu Gly Phe Phe Ala Asn Phe Ser Val Val Gln
225                 230                 235                 240

Ser Asn Thr Asp Glu Asp Phe Gln Cys Lys Glu Ala Leu Gly Met Glu
                245                 250                 255

Ser Gly Glu Ile His Phe Asp Gln Ile Ser Val Ser Ser Gln Tyr Ser
            260                 265                 270

Met Asn Trp Ser Ala Glu Arg Ser Arg Leu Asn Tyr Val Glu Asn Gly
        275                 280                 285

Trp Thr Pro Gly Glu Asp Thr Tyr Lys Glu Trp Ile Gln Val Asp Leu
    290                 295                 300

Glu Asn Leu Arg Phe Val Ser Gly Ile Gly Thr Gln Gly Ala Ile Ser
305                 310                 315                 320

Lys Glu Thr Lys Lys Lys Tyr Phe Val Lys Ser Tyr Lys Val Asp Ile
                325                 330                 335

Ser Ser Asn Gly Glu Asp Trp Ile Thr Leu Lys Asp Gly Asn Lys His
            340                 345                 350

Leu Val Phe Thr Gly Asn Thr Asp Ala Thr Asp Val Val Tyr Arg Pro
        355                 360                 365

Phe Ser Lys Pro Val Ile Thr Arg Phe Val Arg Ile Arg Pro Val Thr
    370                 375                 380

Trp Glu Asn Gly Ile Ser Leu Arg Phe Glu Leu Tyr Gly Cys Lys Ile
385                 390                 395                 400

Thr Asp Tyr Pro Cys Ser Arg Met Leu Gly Met Val Ser Gly Leu Ile
                405                 410                 415

Ser Asp Ser Gln Ile Thr Ala Ser Ser Gln Val Asp Arg Asn Trp Val
            420                 425                 430

Pro Glu Leu Ala Arg Leu Val Thr Ser Arg Ser Gly Trp Ala Leu Pro
        435                 440                 445

Pro Ser Asn Thr His Pro Tyr Thr Asn Glu Trp Leu Gln Ile Asp Leu
    450                 455                 460

Ala Glu Glu Lys Ile Val Arg Gly Val Ile Gln Gly Gly Lys His
465                 470                 475                 480

Arg Glu Asn Lys Val Phe Met Arg Lys Phe Lys Ile Gly Tyr Ser Asn
```

```
                            485                 490                 495
Asn Gly Thr Glu Trp Glu Met Ile Met Asp Ser Ser Lys Asn Lys Pro
            500                 505                 510
Lys Thr Phe Glu Gly Asn Thr Asn Tyr Asp Thr Pro Glu Leu Arg Thr
            515                 520                 525
Phe Ala His Ile Thr Thr Gly Phe Ile Arg Ile Pro Glu Arg Ala
            530                 535                 540
Ser Ala Ser Gly Leu Ala Leu Arg Leu Glu Leu Leu Gly Cys Glu Val
545                 550                 555                 560
Glu

<210> SEQ ID NO 26
<211> LENGTH: 560
<212> TYPE: PRT
<213> ORGANISM: Danio rerio

<400> SEQUENCE: 26

Cys Gly Asp Asn Ile Arg Ile Thr Ser Ala Asn Tyr Leu Thr Ser Pro
1               5                   10                  15
Gly Tyr Pro Val Ser Tyr Pro Ser Gln Lys Cys Ile Trp Val Ile
            20                  25                  30
Thr Ala Pro Gly Pro Asn Gln Arg Ile Leu Ile Asn Phe Asn Pro His
            35                  40                  45
Phe Asp Leu Glu Asp Arg Glu Cys Lys Tyr Asp Tyr Val Glu Val Arg
        50                  55                  60
Asp Gly Val Asp Glu Asn Gly Gln Leu Val Gly Lys Tyr Cys Gly Lys
65                  70                  75                  80
Ile Ala Pro Ser Pro Val Val Ser Ser Gly Asn Gln Leu Phe Ile Lys
                85                  90                  95
Phe Val Ser Asp Tyr Glu Thr His Gly Ala Gly Phe Ser Ile Arg Tyr
            100                 105                 110
Glu Ile Phe Lys Arg Gly Pro Glu Cys Ser Arg Asn Phe Thr Ser Ser
            115                 120                 125
Ser Gly Val Ile Lys Ser Pro Gly Phe Pro Glu Lys Tyr Pro Asn Asn
        130                 135                 140
Leu Asp Cys Thr Phe Met Ile Phe Ala Pro Lys Met Ser Glu Ile Val
145                 150                 155                 160
Leu Glu Phe Glu Ser Phe Glu Leu Glu Pro Asp Thr Gln Pro Pro Ala
                165                 170                 175
Gly Val Phe Cys Arg Tyr Asp Arg Leu Glu Ile Trp Asp Gly Phe Pro
            180                 185                 190
Gly Val Gly Pro Tyr Ile Gly Arg Tyr Cys Gly Gln Asn Thr Pro Gly
            195                 200                 205
Arg Ile Ile Ser Tyr Thr Gly Thr Leu Ala Met Thr Ile Asn Thr Asp
        210                 215                 220
Ser Ala Ile Ala Lys Glu Gly Phe Ser Ala Asn Phe Thr Val Leu Glu
225                 230                 235                 240
Arg Thr Val Pro Asp Asp Phe Asp Cys Thr Glu Pro Leu Gly Met Glu
                245                 250                 255
Thr Gly Glu Ile His Ser Asp Gln Ile Met Ala Ser Ser Gln Tyr Ser
            260                 265                 270
Asn Ser Trp Ser Ala Glu Arg Ser Arg Leu Asn Asn Pro Glu Asn Gly
            275                 280                 285
Trp Thr Pro Leu Lys Asp Thr Asn Lys Glu Trp Ile Gln Val Asp Leu
        290                 295                 300
```

Gly Phe Leu Arg Phe Val Ser Ala Ile Gly Thr Gln Gly Ala Ile Ser
305                 310                 315                 320

Gln Glu Thr Lys Lys Tyr Val Lys Glu Tyr Lys Val Asp Val
            325                 330                 335

Ser Ser Asn Gly Glu Asp Trp Ile Thr Ile Lys Ser Gly Pro Lys Gln
                340                 345                 350

Lys Leu Phe Gln Gly Asn Thr Asn Ala Thr Asp Val Val Lys Ala Lys
            355                 360                 365

Phe Pro Lys Pro Thr Leu Thr Arg Tyr Leu Arg Ile Arg Pro Ile Asn
370                 375                 380

Trp Glu Thr Gly Ile Ala Leu Arg Phe Glu Val Tyr Gly Cys Lys Ile
385                 390                 395                 400

Ser Glu Tyr Pro Cys Ser Gly Met Leu Gly Met Val Ser Gly Leu Ile
                405                 410                 415

Thr Asp Ser Gln Ile Thr Val Ser Ser His Ile Glu Arg Thr Trp Val
                420                 425                 430

Ser Glu Asn Ala Arg Leu Leu Thr Ser Arg Ser Gly Trp Met Leu Leu
            435                 440                 445

Pro Gln Ser Gln Pro Tyr Ala Asp Glu Trp Leu Gln Ile Asp Leu Ala
450                 455                 460

Glu Glu Lys Leu Val Lys Gly Leu Ile Ile Gln Gly Gly Lys His Arg
465                 470                 475                 480

Asp Asn Lys Val Phe Met Lys Lys Phe Arg Leu Gly Tyr Ser Asn Asn
                485                 490                 495

Gly Ser Asp Trp Lys Leu Val Met Asp Ala Thr Gly Asn Lys Pro Lys
            500                 505                 510

Ile Phe Glu Gly Asn Leu Asn Tyr Asp Thr Pro Ala Leu Arg Thr Met
            515                 520                 525

Glu Pro Val Leu Thr Arg Phe Val Arg Ile Tyr Pro Glu Arg Gly Thr
530                 535                 540

Pro Ala Gly Met Gly Leu Arg Leu Glu Leu Leu Gly Cys Glu Met Glu
545                 550                 555                 560

<210> SEQ ID NO 27
<211> LENGTH: 11
<212> TYPE: PRT
<213> ORGANISM: Homo sapiens

<400> SEQUENCE: 27

Arg Ala Ser Gln Ser Ile Ser Asn Tyr Leu Ala
1               5                   10

<210> SEQ ID NO 28
<211> LENGTH: 11
<212> TYPE: PRT
<213> ORGANISM: Homo sapiens

<400> SEQUENCE: 28

Arg Ala Ser Gln Asp Val Ser Thr Ala Val Ala
1               5                   10

<210> SEQ ID NO 29
<211> LENGTH: 7
<212> TYPE: PRT
<213> ORGANISM: Homo sapiens

<400> SEQUENCE: 29

Ala Ala Ser Ser Leu Glu Ser

<210> SEQ ID NO 30
<211> LENGTH: 7
<212> TYPE: PRT
<213> ORGANISM: Homo sapiens

<400> SEQUENCE: 30

Ser Ala Ser Phe Leu Tyr Ser
1               5

<210> SEQ ID NO 31
<211> LENGTH: 9
<212> TYPE: PRT
<213> ORGANISM: Homo sapiens

<400> SEQUENCE: 31

Gln Gln Tyr Asn Ser Leu Pro Trp Thr
1               5

<210> SEQ ID NO 32
<211> LENGTH: 9
<212> TYPE: PRT
<213> ORGANISM: Homo sapiens

<400> SEQUENCE: 32

Gln Gln Ser Tyr Thr Thr Pro Thr Thr
1               5

<210> SEQ ID NO 33
<211> LENGTH: 9
<212> TYPE: PRT
<213> ORGANISM: Homo sapiens

<400> SEQUENCE: 33

Gln Gln Ala Trp Ala Tyr Leu Thr Thr
1               5

<210> SEQ ID NO 34
<211> LENGTH: 10
<212> TYPE: PRT
<213> ORGANISM: Homo sapiens

<400> SEQUENCE: 34

Gly Phe Thr Phe Ser Ser Tyr Ala Met Ser
1               5                   10

<210> SEQ ID NO 35
<211> LENGTH: 10
<212> TYPE: PRT
<213> ORGANISM: Homo sapiens

<400> SEQUENCE: 35

Gly Phe Thr Ile Ser Gly Tyr Gly Ile His
1               5                   10

<210> SEQ ID NO 36
<211> LENGTH: 17
<212> TYPE: PRT
<213> ORGANISM: Homo sapiens

<400> SEQUENCE: 36

Val Ile Ser Gly Asp Gly Gly Ser Thr Tyr Tyr Ala Asp Ser Val Lys
1               5                   10                  15

Gly

```
<210> SEQ ID NO 37
<211> LENGTH: 18
<212> TYPE: PRT
<213> ORGANISM: Homo sapiens

<400> SEQUENCE: 37

Ala Tyr Ile Tyr Pro Asp Ser Gly Tyr Thr Asp Tyr Ala Asp Ser Val
1               5                   10                  15

Lys Gly

<210> SEQ ID NO 38
<211> LENGTH: 4
<212> TYPE: PRT
<213> ORGANISM: Homo sapiens

<400> SEQUENCE: 38

Gly Phe Asp Tyr
1

<210> SEQ ID NO 39
<211> LENGTH: 15
<212> TYPE: PRT
<213> ORGANISM: Homo sapiens

<400> SEQUENCE: 39

Glu Asp Phe Arg Asn Arg Arg Arg Leu Trp Tyr Val Met Asp Tyr
1               5                   10                  15
```

ANTI-PAN NEUROPILIN ANTIBODY AND BINDING FRAGMENTS THEREOF

This is a National Stage of International Application No. PCT/US2007/069185, filed on May 17, 2007, the disclosure of which is incorporated by reference in its entirety herein.

SEQUENCE LISTING

The instant application contains a Sequence Listing which has been submitted in ASCII format via EFS-Web and is hereby incorporated by reference in its entirety. Said ASCII copy, created on May 24, 2011, is named GNE241US.txt and is 92,777 bytes in size.

FIELD OF THE INVENTION

The present invention provides crystal structures of neuropilin 1 (Nrp1) and neuropilin 2 (Nrp2) fragments alone and in complex with anti-neuropilin antibodies, and their uses. The invention further provides antibodies binding to Nrp1 and/or Nrp2 and methods for their use.

BACKGROUND OF THE INVENTION

Development of a vascular system is a fundamental requirement for many physiological and pathological processes. Actively growing tissues such as embryos and tumors require adequate blood supply. They satisfy this need by producing pro-angiogenic factors, which promote new blood vessel formation and maintenance via a process generally referred to as angiogenesis. Vascular formation is a complex but orderly biological event involving all or many of the following steps: a) Endothelial cells (ECs) proliferate from existing ECs or differentiate from progenitor cells; b) ECs migrate and coalesce to form cord-like structures; c) vascular cords then undergo tubulogenesis to form vessels with a central lumen d) existing cords or vessels send out sprouts to form secondary vessels; e) primitive vascular plexus undergo further remodeling and reshaping; and f) peri-endothelial cells are recruited to encase the endothelial tubes, providing maintenance and modulatory functions to the vessels; such cells including pericytes for small capillaries, smooth muscle cells for larger vessels, and myocardial cells in the heart. Hanahan, D. *Science* 277:48-50 (1997); Hogan, B. L. & Kolodziej, P. A. *Nature Reviews Genetics.* 3:513-23 (2002); Lubarsky, B. & Krasnow, M. A. *Cell.* 112:19-28 (2003).

It is now well established that angiogenesis is implicated in the pathogenesis of a variety of disorders. These include solid tumors and metastasis, atherosclerosis, retrolental fibroplasia, hemangiomas, chronic inflammation, intraocular neovascular diseases such as proliferative retinopathies, e.g., diabetic retinopathy, age-related macular degeneration (AMD), neovascular glaucoma, immune rejection of transplanted corneal tissue and other tissues, rheumatoid arthritis, and psoriasis. Folkman et al., J. Biol. Chem., 267:10931-10934 (1992); Klagsbrun et al., Annu. Rev. Physiol. 53:217-239 (1991); and Garner A., "Vascular diseases", In: Pathobiology of Ocular Disease. A Dynamic Approach, Garner A., Klintworth G K, eds., 2nd Edition (Marcel Dekker, NY, 1994), pp 1625-1710.

In the case of tumor growth, angiogenesis appears to be crucial for the transition from hyperplasia to neoplasia, and for providing nourishment for the growth and metastasis of the tumor. Folkman et al., *Nature* 339:58 (1989). The neovascularization allows the tumor cells to acquire a growth advantage and proliferative autonomy compared to the normal cells. A tumor usually begins as a single aberrant cell which can proliferate only to a size of a few cubic millimeters due to the distance from available capillary beds, and it can stay 'dormant' without further growth and dissemination for a long period of time. Some tumor cells then switch to the angiogenic phenotype to activate endothelial cells, which proliferate and mature into new capillary blood vessels. These newly formed blood vessels not only allow for continued growth of the primary tumor, but also for the dissemination and recolonization of metastatic tumor cells. Accordingly, a correlation has been observed between density of microvessels in tumor sections and patient survival in breast cancer as well as in several other tumors. Weidner et al., *N. Engl. J. Med* 324:1-6 (1991); Horak et al., *Lancet* 340:1120-1124 (1992); Macchiarini et al., *Lancet* 340:145-146 (1992). The precise mechanisms that control the angiogenic switch is not well understood, but it is believed that neovascularization of tumor mass results from the net balance of a multitude of angiogenesis stimulators and inhibitors (Folkman, 1995, *Nat Med* 1(1): 27-31).

The process of vascular development is tightly regulated. To date, a significant number of molecules, mostly secreted factors produced by surrounding cells, have been shown to regulate EC differentiation, proliferation, migration and coalescence into cord-like structures. For example, vascular endothelial growth factor (VEGF) has been identified as the key factor involved in stimulating angiogenesis and in inducing vascular permeability. Ferrara et al., *Endocr. Rev.* 18:4-25 (1997). The finding that the loss of even a single VEGF allele results in embryonic lethality points to an irreplaceable role played by this factor in the development and differentiation of the vascular system. Furthermore, VEGF has been shown to be a key mediator of neovascularization associated with tumors and intraocular disorders. Ferrara et al., *Endocr. Rev.* supra. The VEGF mRNA is overexpressed by the majority of human tumors examined. Berkman et al., *J. Clin. Invest.* 91:153-159 (1993); Brown et al., *Human Pathol.* 26:86-91 (1995); Brown et al., *Cancer Res.* 53:4727-4735 (1993); Mattern et al., *Brit. J. Cancer* 73:931-934 (1996); Dvorak et al., *Am. J. Pathol.* 146:1029-1039 (1995).

Also, the concentration levels of VEGF in eye fluids are highly correlated to the presence of active proliferation of blood vessels in patients with diabetic and other ischemia-related retinopathies. Aiello et al., *N Engl. J. Med.* 331:1480-1487 (1994). Furthermore, studies have demonstrated the localization of VEGF in choroidal neovascular membranes in patients affected by AMD. Lopez et al., *Invest. Opthalmol. Vis. Sci.* 37:855-868 (1996).

Anti-VEGF neutralizing antibodies suppress the growth of a variety of human tumor cell lines in nude mice (Kim et al., *Nature* 362:841-844 (1993); Warren et al., *J. Clin. Invest.* 95:1789-1797 (1995); Borgström et al., *Cancer Res.* 56:4032-4039 (1996); Melnyk et al., *Cancer Res.* 56:921-924 (1996)) and also inhibit intraocular angiogenesis in models of ischemic retinal disorders. Adamis et al., *Arch. Opthalmol.* 114:66-71 (1996). Therefore, anti-VEGF monoclonal antibodies or other inhibitors of VEGF action are promising candidates for the treatment of tumors and various intraocular neovascular disorders. Such antibodies are described, for example, in EP 817,648 published Jan. 14, 1998; and in WO98/45331 and WO98/45332, both published Oct. 15, 1998. One of the anti-VEGF antibodies, bevacizumab, has been approved by the FDA for use in combination with a chemotherapy regimen to treat metastatic colorectal cancer (CRC) and non-small cell lung cancer (NSCLC). And bevacizumab is being investigated in many ongoing clinical trials for treating various cancer indications.

During development of the nervous system, neurons send out cable-like axons that migrate over long distances in order to reach their targets. See review by Carmeliet and Tessier-Lavigne (2005) *Nature* 436:193-200. At the leading tip of a growing axon is a highly motile, sensory structure called growth cone. Through dynamic cycles of extension and retraction of filopodial extensions, the growth cone continually senses and asseses from a myriad of guidance cues in its spatial environment, and accurately selects a correct track for extension towards its final target.

Over the past decade, considerable progress has been made in understanding axon guidance mechanisms. See review by Dickson (2002) *Science* 298:1959-64. Guidance cues come in four varieties: attractants and repellents; which may act either at short range (i.e., cell- or matrix-associated) or at longer range (i.e., diffusible). So far, four major families of axon guidance molecules have been identified: the netrins, semaphorins, ephrins and slits. See review by Huber et al (2003) *Annu Rev Neurosci* 26:509-63.

The semaphorins (Sema), also called collapsins, belong to a large family of phylogenetically conserved secreted and membrane-associated proteins. Members of the semaphorin family are capable of mediating both repulsive and attractive axon guidance events during neural development. Raper (2000) *Curr Opin Neurobiol* 10:88-94. The more than thirty semaphorins identified to date all share a conserved N-terminal Sema domain of about 500 amino acids. Semaphorin members are classified into eight subfamilies depending on their structural similarities and species of origin. For more details on unified nomenclature for semaphorins, see Semaphorin Nomenclature Committee (1999) *Cell* 97:551-552.

The neuropilin (NRP) family is comprised of two homologous proteins, neuropilin-1 (NRP1) and neuropilin-2 (NRP2). NRP1 was first identified as a type I 130-kDa transmembrane glycoprotein expressed in growth cones of growing axons. NRP2 was subsequently identified by expression cloning. Fujisawa and Kitsukawa (1998) *Curr Opin Neurobiol* 8:587-592. NRPs are found to be receptors for a subset of semaphorins, the class 3 semaphorins. It was suggested that NRPs function as non-signaling co-receptors along with another semaphorin receptor family, plexins.

Although initially described as a mediator of axon guidance, NRPs have also been found to play critical roles in vascular development. Carmeliet and Tessier-Lavigne (2005). It is identified as an isoform-specific VEGF receptor expressed on tumor and endothelial cells, prompting considerable efforts to understand the role of NRPs in vascular and tumor biology. Soker et al (1998) *Cell* 92:735-745; Klagsbrun et al (2002) *Adv Exp Med Biol* 515:33-48. Genetic studies have provided strong evidence that Nrp1 is required for vascular morphogenesis. Loss of Nrp1 function results in vascular remodeling and branching defects, a phenotype that can be further enhanced by the loss of Nrp2 function. Kawasaki et al. (1999) *Development* 126:4895-4902; Takashima et al. (2002) *Proc Natl Acad Sci USA* 99:3657-3662. These results suggest that early in development Nrp1 and Nrp2 may have overlapping functions. However, the expression of each Nrp is partitioned later in development, with Nrp1 being expressed primarily in arteries, and Nrp2 in veins and lymphatic vessels. Yuan et al (2002) *Development* 129:4797-4806; Herzog et al. (2001) *Mech Dev* 109:115-119. Notably, loss of Nrp2 function alone specifically impairs lymphatic development.

As Nrp1 is expressed in many other cell types during development, the role of vascular Nrp1 was addressed through the generation of an EC-specific knock-out, which resulted in similar vascular defects to those seen in the null allele. Gu et al. (2003) *Dev Cell* 5:45-57. Interestingly, this study also showed that Sema3A binding to NRP1 is not required for vascular development. In another study, defects were observed in the guidance of endothelial tip cells in the developing hindbrain in Nrp1 KO embryos. Gerhardt et al. (2004) *Dev Dyn* 231:503-509.

Despite the extensive studies in NRP1's role in vascular development, it remains unclear as to whether NRP1 exerts its vascular function exclusively via the VEGF-VEGF Receptor 2 (VEGFR2) pathway, as an enhancer for VEGF binding to VEGFR2 and thereby for VEGFR2 signaling, or via a signaling pathway independent of VEGFR2, or a combination of both.

Monoclonal antibodies can be manufactured using recombinant DNA technology. Widespread use has been made of monoclonal antibodies, particularly those derived from rodents, however nonhuman antibodies are frequently antigenic in humans. The art has attempted to overcome this problem by constructing "chimeric" antibodies in which a nonhuman antigen-binding domain is coupled to a human constant domain (Cabilly et al., U.S. Pat. No. 4,816,567). The isotype of the human constant domain may be selected to tailor the chimeric antibody for participation in antibody-dependent cellular cytotoxicity (ADCC) and complement-dependent cytotoxicity. In a further effort to resolve the antigen binding functions of antibodies and to minimize the use of heterologous sequences in human antibodies, humanized antibodies have been generated for various antigens in which substantially less than an intact human variable domain has been substituted at regions by the corresponding sequence from a non-human species. For example, rodent residues have been substituted for the corresponding segments of a human antibody. In practice, humanized antibodies are typically human antibodies in which some complementarity determining region (CDR) residues and possibly some framework region (FR) residues are substituted by residues from analogous sites in rodent antibodies. Jones et al. (1986) *Nature* 321:522-525; Riechmann et al. (1988) *Nature* 332:323-327; Verhoeyen et al. (1988) *Science* 239:1534-1536.

Prior to administering a therapeutic antibody to human, preclinical studies in nonhuman mammals are generally desired to evaluate the efficacy and/or toxicity of the antibody. Ideally, the antibodies subject to these studies are capable of recognizing and reacting with high potency to a target antigen endogenous to the host animal such as mouse or nonhuman primate.

Phage display technology has provided a powerful tool for generating and selecting novel proteins that bind to a ligand, such as an antigen. Using the technique of phage display, large libraries of protein variants can be generated and rapidly sorted for those sequences that bind to a target antigen with high affinity. Nucleic acids encoding variant polypeptides are fused to a nucleic acid sequence encoding a viral coat protein, such as the gene III protein or the gene VIII protein. Monovalent phage display systems where the nucleic acid sequence encoding the protein or polypeptide is fused to a nucleic acid sequence encoding a portion of the gene III protein have been developed. (Bass, S. (1990) *Proteins* 8:309; Lowman and Wells (1991) *Methods: A Companion to Methods in Enzymology* 3:205). In a monovalent phage display system, the gene fusion is expressed at low levels and wild type gene III proteins are also expressed so that infectivity of the particles is retained. Methods of generating peptide libraries and screening those libraries have been disclosed in many patents (e.g., U.S. Pat. No. 5,723,286, U.S. Pat. No. 5,432,018, U.S. Pat. No. 5,580,717, U.S. Pat. No. 5,427,908 and U.S. Pat. No. 5,498,530).

The demonstration of expression of peptides on the surface of filamentous phage and the expression of functional antibody fragments in the periplasm of *E. coli* was important in the development of antibody phage display libraries. (Smith et al. (1985) *Science* 228:1315; Skerra and Pluckthun (1988) *Science* 240:1038). Libraries of antibodies or antigen binding polypeptides have been prepared in a number of ways including by altering a single gene by inserting random DNA sequences or by cloning a family of related genes. Methods for displaying antibodies or antigen binding fragments using phage display have been described in U.S. Pat. Nos. 5,750,373, 5,733,743, 5,837,242, 5,969,108, 6,172,197, 5,580,717, and 5,658,727. The library is then screened for expression of antibodies or antigen binding proteins with desired characteristics.

Phage display technology has several advantages over conventional hybridoma and recombinant methods for preparing antibodies with the desired characteristics. This technology allows the development of large libraries of antibodies with diverse sequences in less time and without the use of animals. Preparation of hybridomas or preparation of humanized antibodies can easily require several months of preparation. In addition, since no immunization is required, phage antibody libraries can be generated for antigens which are toxic or have low antigenicity (Hogenboom (1988) *Immunotechniques* 4:1-20). Phage antibody libraries can also be used to generate and identify novel therapeutic antibodies.

Phage display libraries have been used to generate human antibodies from immunized, non-immunized humans, germ line sequences, or naïve B cell Ig repertoires (Barbas & Burton (1996) *Trends Biotech* 14:230; Griffiths et al. (1994) *EMBO J.* 13:3245; Vaughan et al. (1996) *Nat. Biotech.* 14:309; Winter EP 0368 684 B1). Naïve, or nonimmune, antigen binding libraries have been generated using a variety of lymphoidal tissues. Some of these libraries are commercially available, such as those developed by Cambridge Antibody Technology and Morphosys (Vaughan et al. (1996) *Nature Biotech* 14:309; Knappik et al. (1999) *J. Mol. Biol.* 296:57). However, many of these libraries have limited diversity.

The ability to identify and isolate high affinity antibodies from a phage display library is important in isolating novel antibodies for therapeutic use. Isolation of high affinity antibodies from a library is dependent on the size of the library, the efficiency of production in bacterial cells and the diversity of the library. See, for e.g., Knappik et al. (1999) *J. Mol. Biol.* 296:57. The size of the library is decreased by inefficiency of production due to improper folding of the antibody or antigen binding protein and the presence of stop codons. Expression in bacterial cells can be inhibited if the antibody or antigen binding domain is not properly folded. Expression can be improved by mutating residues in turns at the surface of the variable/constant interface, or at selected CDR residues. (Deng et al. (1994) *J. Biol. Chem.* 269:9533, Ulrich et al. (1995) *PNAS*, 92:11907-11911; Forsberg et al. (1997 *J. Biol. Chem.* 272:12430). The sequence of the framework region is a factor in providing for proper folding when antibody phage libraries are produced in bacterial cells.

Generating a diverse library of antibodies or antigen binding proteins is also important to isolation of high affinity antibodies. Libraries with diversification in limited CDRs have been generated using a variety of approaches. See, e.g., Tomlinson (2000) *Nature Biotech.* 18:989-994. CDR3 regions are of interest in part because they often are found to participate in antigen binding. CDR3 regions on the heavy chain vary greatly in size, sequence and structural conformation.

Others have also generated diversity by randomizing CDR regions of the variable heavy and light chains using all 20 amino acids at each position. It was thought that using all 20 amino acids would result in a large diversity of sequences of variant antibodies and increase the chance of identifying novel antibodies. (Barbas (1994) *PNAS* 91:3809; Yelton, D E (1995) *J. Immunology* 155:1994; Jackson, J. R. (1995) *J. Immunology* 154:3310 and Hawkins, R E (1992) *J. Mol. Biology* 226:889).

SUMMARY OF THE INVENTION

The present invention provides crystal structures of neuropilin-1 and neuropilin-2 (Nrp1 and Nrp2) fragments alone and in complex with antibodies that selectively block either semaphorin- or VEGF-binding. Nrps adopt an unexpected domain arrangement in which the a2, b1, and b2 domains form a tightly packed core. The locations of the antibody epitopes together with in vitro experiments show that VEGF and semaphorins do not directly compete for Nrp binding. Based on a crystallographic Nrp dimer mediated by the a1 domain, the present invention additionally provides models for receptor dimerization and ligand binding.

Based on these results, in one aspect, the present invention provides a crystal formed by an $Nrp1_{b1b2}$ fragment that diffracts x-ray radiation to produce a diffraction pattern representing the three-dimensional structure of said fragment, having approximately the following cell constants a=65.9 Å, b=66.7 Å, c=74.7 Å, and a space group of $P2_12_12_1$.

In another aspect, the invention concerns a crystal formed by an $Nrp1_{a2b1b2}$ fragment that diffracts x-ray radiation to produce a diffraction pattern representing the three-dimensional structure of said fragment, having approximately the following cell constants a=53.2 Å, b=68.2 Å, c=66.6 Å, and a space group of $P2_1$.

In yet another aspect, the invention concerns a crystal of a complex formed between an $Nrp1_{b1}$ fragment and a Fab fragment of anti-$Nrp1^B$ antibody (YW107.4.87) that inhibits binding of vascular endothelial growth factor (VEGF) to Nrp1, wherein said crystal diffracts x-ray radiation to produce a diffraction pattern representing the three-dimensional structure of said complex, having approximately the following cell constants a=213 Å, b=213 Å, c=45.3 Å, and a space group of H3.

In a further aspect, the invention concerns a crystal formed by an $Nrp2_{b1b2}$ fragment that diffracts x-ray radiation to produce a diffraction pattern representing the three-dimensional structure of said fragment, having approximately the following cell constants a=36.5 Å, b=70.5 Å, c=122 Å, and a space group of $P2_12_12_1$.

In a still further aspect, the invention concerns a crystal formed by an $Nrp2_{a2b1b2}$ fragment that diffracts x-ray radiation to produce a diffraction pattern representing the three-dimensional structure of said fragment, having approximately the following cell constants a=50.1 Å, b=193 Å, c=66.2 Å, and a space group of $P2_1$.

In another aspect, the invention concerns a crystal of a complex formed between an $Nrp2_{a1a2b1b2}$ fragment and a Fab fragment of anti-$panNrp^A$ antibody that inhibits semaphorin binding to Nrp2, wherein said crystal diffracts x-ray radiation to produce a diffraction pattern representing the three-dimensional structure of said complex, having approximately the following cell constants a=148 Å, b=106 Å, c=92.4 Å, and a space group of C2.

The invention further concerns a crystal of a complex formed between an $Nrp2_{a1a2b1b2}$ fragment and a Fab fragment of anti-$panNrp^A$ antibody that inhibits semaphorin binding to Nrp2, wherein said crystal diffracts x-ray radiation to produce a diffraction pattern representing the three-dimensional structure of said complex, having approximately the following cell constants a=121 Å, b=121 Å, c=203 Å, and a space group of P3$_2$21.

In another aspect, the invention concerns an anti-panNrp$^A$ antibody comprising a light chain variable domain sequence shown in FIG. 7 and/or a heavy chain variable domain sequence shown in FIG. 8, or a fragment thereof.

In yet another aspect, the invention concerns an anti-panNrp$^A$ YW68.11 antibody Fab fragment comprising the sequence shown in FIG. 9A.

In a further aspect, the invention concerns an anti-panNrp$^A$ YW68.11.26 antibody Fab fragment comprising the sequence shown in FIG. 9B.

In a still further aspect, the invention concerns an anti-Nrp antibody that competes for Nrp binding with the anti-panNrp$^A$ antibody.

In one embodiment, the anti-Nrp antibody binds essentially to the same epitope as the anti-panNrp$^A$ antibody.

In another embodiment, the anti-Nrp antibody binds to an epitope comprising at least part of an interface defined by amino acid residues Y39, Y45, P46, Q47, F72, N73 P74, H75, F76, A133, and R138 of the Nrp2$_{a1a2b1b2}$ amino acid sequence.

In yet another embodiment, the anti-Nrp antibody binds to both Nrp1 and Nrp2.

In further embodiments, the anti-Nrp antibody has a binding affinity of at least about 0.10 nM for both Nrp1 and Nrp2, or at least about 0.15 nM for both Nrp1 and Nrp2, or at least about 0.20 nM for both Nrp1 and Nrp2, or at least about 0.25 nM for both Nrp1 and Nrp2, or at least about 0.30 nM for both Nrp1 and Nrp2.

In another embodiment, the anti-Nrp antibody blocks Sema3 binding to both Nrp1 and Nrp2.

In yet another embodiment, the anti-Nrp antibody does not block VEGF binding to Nrp1 or Nrp2.

In a different embodiment, the anti-Nrp antibody inhibits semaphorin biological activity in vitro.

In an additional embodiment, the anti-Nrp antibody inhibits semaphorin biological activity in vivo.

In another aspect, the invention concerns a method of preparing a semaphorin antagonist, comprising designing a molecule binding to a site comprising at least part of an interface defined by amino acid residues Y39, Y45, P46, Q47, F72, N73 P74, H75, F76, A133, and R138 of the Nrp2$_{a1a2b1b2}$ amino acid sequence, synthesizing the compound, and confirming that the compound blocks semaphorin binding to Nrp1 and Nrp2.

In one embodiment, the antagonist does not interfere with the binding of VEGF to Nrp1 or Nrp2, and the method may comprise an additional step of confirming that said antagonist does not interfere with the binding of VEGF to Nrp1 or Nrp2.

In another embodiment, the method further comprises the step of confirming that the antagonist does not interfere with VEGF biological activity.

The antagonist may, for example, be selected from the group consisting of antibodies, antibody fragments, binding polypeptides, peptides, and non-peptide small molecules, and preferably is an antibody or an antibody fragment, where the antibody fragments include, without limitation, Fab, Fab', F(ab')$_2$, scFv, (scFv)$_2$, dAb, linear antibodies, single-chain antibody molecules, minibodies, diabodies, and multispecific antibodies formed from antibody fragments.

In another aspect, the invention concerns a method of preparing a VEGF antagonist, comprising using a three-dimensional structure derived from a crystal of a complex formed between an Nrp1$_{b1}$ fragment and a Fab fragment of anti-Nrp1$^B$ antibody (YW107.4.87), wherein the crystal diffracts x-ray radiation to produce a diffraction pattern representing the three-dimensional structure of said complex, having approximately the following cell constants a=213 Å, b=213 Å, c=45.3 Å, and a space group of H3, to design a molecule binding to a site comprising at least part of the epitope bound by said Nrp1$^B$ antibody, synthesizing the compound, and confirming that the compound inhibits VEGF binding to Nrp1.

In one embodiment, the antagonist does not interfere with semaphorin binding to Nrp1, and the method may additionally include a step confirming this.

In another embodiment, the antagonist inhibits VEGF biological activity.

In yet another embodiment, the method further comprises the step of confirming that the antagonist inhibits a VEGF biological activity.

In a further embodiment, the antagonist inhibits vascular remodeling.

In a still further embodiment, the antagonist is selected from the group consisting of antibodies, antibody fragments, binding polypeptides, peptides, and non-peptide small molecules, and preferably is an antibody or an antibody fragment, where the antibody fragment can, for example, be a Fab, Fab', F(ab')$_2$, scFv, (scFv)$_2$, dAb, linear antibody, single-chain antibody molecule, minibody, diabody, or multispecific antibody formed from antibody fragments.

The invention further concerns a method for the treatment of cancer comprising administering to a mammalian subject in need an effective amount of a VEGF antagonist prepared by the foregoing method of the present invention. The cancer may, for example, be selected from the group consisting of breast cancer, colorectal cancer, non-small cell lung cancer, non-Hodgkins lymphoma (NHL), renal cancer, prostate cancer, liver cancer, head and neck cancer, melanoma, ovarian cancer, mesothelioma, and multiple myeloma.

In another embodiment, the treatment further comprises a second therapeutic agent, where the second therapeutic agent can be, without limitation, an agent selected from the group consisting of an anti-angiogenic agent, an anti-neoplastic composition, a chemotherapeutic agent and a cytotoxic agent, such as a further VEGF antagonist.

In a further embodiment, the further VEGF antagonist is an anti-hVEGF antibody or a fragment thereof.

The anti-hVEGF antibody can, for example, be capable of binding to the same VEGF epitope as the antibody A4.6.1, and specifically bevacizumab or ranibizumab.

In other embodiments, the second therapeutic agent is a receptor tyrosine kinase inhibitor selected from the group consisting of vatalanib (PTK787), erlotinib (TARCEVA®), OSI-7904, ZD6474 (ZACTIMA®), ZD6126 (ANG453), ZD1839, sunitinib (SUTENT®), semaxanib (SU5416), AMG706, AG013736, Imatinib (GLEEVEC®), MLN-518, CEP-701, PKC-412, Lapatinib (GSK572016), VELCADE®, AZD2171, sorafenib (NEXAVAR®), XL880, and CHIR-265.

BRIEF DESCRIPTION OF THE DRAWINGS

FIG. 5—Features of the Nrp VEGF- and heparin-binding domains. A) Superposition of the Nrp b1b2 crystal structures (Nrp1, yellow (b1) and red (b2); Nrp2, grey). Blue (Nrp1) and green (Nrp2) residues highlight conformational differences in the "spikes" of b2, but not b1. B) The molecular surface of the rat (PDB accession no. 2ORZ) (Vancer Kooi, C. W., et al., Proc Natl Acad Sci USA (2007)) and human b1b2 crystal structures are colored by electrostatic potential. Yellow arrows indicate an acidic groove that is formed by the "spikes" in the b1 domain and that represents the Tuftsin-binding site in the rat structure (Vander Kooi et al., supra). Green arrows indicate the approximate location of the heparin-binding patch. C) The relative sequence conservation (green, 100%; yellow, ≧75%) of the b1b2 domains among twelve Nrps (FIG. S3) was mapped onto the surface of the human Nrp1 b1b2 structure. Two highly conserved patches are delineated in orange. Residues outlined in cyan indicate those residues that contact the Fab in the anti-Nrp1[B]-Fab/b1 complex. The a2 domain (wheat) is shown by using a superposition of the b1b2 and a2b1b2 structures from Nrp1. D) Ribbon representation of the anti-Nrp1[B]-Fab/b1 complex (yellow, b1; orange, heavy chain; grey, light chain). E) The anti-Nrp1[B]/b1 interface. The b1 domain is cartooned as a molecular surface according to the electrostatic potential; the yellow arrow indicates the VEGF tail binding groove. Only CDRs H3 and L1 contact b1.

FIG. 7—Light Chain Variable Domain Sequence Alignment of Anti-panNrp[4] Clones YW68.11 (SEQ ID NO: 4) and YW68.11.26 (SEQ ID NO: 5), in alignment with a human KappaI light chain sequence (huKI, SEQ ID NO: 3). The light chain CDRL1, CDR2, and CDRL3 sequences are boxed, and assigned the following SEQ ID NOs: huKI CDRL1: SEQ ID NO: 27; YW68.11 CDRL1: SEQ ID NO 28; YW68.11.26 CDRL1: SEQ ID NO: 28; huKI CDRL2: SEQ ID NO: 29; YW68.11 CDRL2: SEQ ID NO: 30; YW68.11.26 CDRL2: SEQ ID NO: 30; huKI CDRL3: SEQ ID NO: 31; YW68.11 DRL3: SEQ ID NO: 32; YW68.11.26 CDRL3: SEQ ID NO: 33.

FIG. 8—Heavy Chain Variable Domain Sequence Alignment of Anti-panNrp[4] Clones YW68.11 (SEQ ID NO: 7) and YW68.11.26 (SEQ ID NO: 7), in alignment with a heavy chain subgroup III (humIII) sequence (SEQ ID NO: 6). The heavy chain CDRH1, CDRH2 and CDRH3 sequences are boxed and assigned the following SEQ ID NOs: humIII CDRH1: SEQ ID NO: 34; YW68.11 CDRH1: SEQ ID NO: 35; YW68.11.26 CDRH1: SEQ ID NO: 35; humIII CDRH2: SEQ ID NO: 36; YW68.11 CDRH2: SEQ ID NO: 37; YW68.11.26 CDRH2: SEQ ID NO: 37; humIII CDRH3: SEQ ID NO: 38; YW68.11 CDRH3: SEQ ID NO: 39; and YW68.11.26 CDRH3: SEQ ID NO: 39.

FIG. 9A—Complete Sequence of Human Anti-panNrp[4] IgG1 antibody YW68.11 (SEQ ID NO: 9).

FIG. 9B—Complete Sequence of Huma Anti-panNrp[4] IgG1 antibody YW68.11.26 (SEQ ID NO: 10).

FIG. 10—Conditions Used for Crystallization and Cryoprotection.

DETAILED DESCRIPTION OF THE INVENTION

Figure 1A:
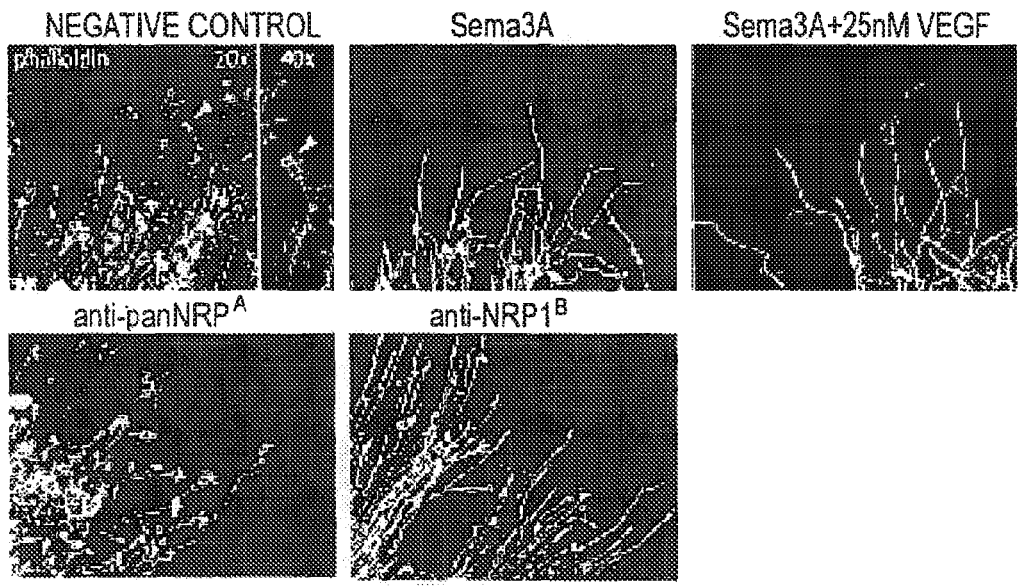
FIG. 1—VEGF Does Not Block Sema3A-Induced Growth Cone Collapse of DRG Neurons A) Images of axon growth cones. Untreated DRG's have large actin-rich growth cones (arrowhead) that are significantly reduced upon addition of Sema3A. Anti-Nrp antibodies were added at 50 μg/ml. B) Quantification of Sema3A-induced growth cone collapse. The percentage of collapsed growth cones were calculated by counting collapsed and uncollapsed growth cones (N=4 explants per condition). Error bars represent standard error of the mean.

The present invention relates to novel crystal structures, compositions, methods for modulating NRP mediated biological activities, and screening assays to identify candidates capable of modulating NRP mediated biological activities.

DEFINITIONS

"Neuropilin" or NRP refers collectively to neuropilin-1 (NRP1), neuropilin-2 (NRP2) and their isoforms and variants, as described in Rossignol et al. (2000) *Genomics* 70:211-222. Neuropilins are 120 to 130 kDa non-tyrosine kinase receptors. There are multiple NRP-1 and NRP-2 splice variants and soluble isoforms. The basic structure of neuropilins comprises five domains: three extracellular domains (a1a2, b1b2 and c), a transmembrane domain, and a cytoplasmic domain. The a1a2 domain is homologous to complement components C1r and C1s (CUB), which generally contains four cysteine residues that form two disculfid bridges. The b1b2 domain is homologous to coagulation factors V and VIII. The central portion of the c domain is designated as MAM due to its homology to meprin, A5 and receptor tyrosine phosphotase proteins. The a1a2 and b1b2 domains are responsible for ligand binding, whereas the c domain is critical for homodimerization or heterodimerization. Gu et al. (2002) *J. Biol. Chem.* 277:18069-76; He and Tessier-Lavigne (1997) *Cell* 90:739-51.

"Neuropilin mediated biological activity" refers in general to physiological or pathological events in which neuropilin-1 and/or neuropilin-2 plays a substantial role. Non-limiting examples of such activities are axon guidance during embryonic nervous system development or neuron-regeneration, angiogenesis (including vascular modeling), tumorgenesis and tumor metastasis.

The term "antibody" is used in the broadest sense and specifically covers monoclonal antibodies (including full length monoclonal antibodies), polyclonal antibodies, multi-specific antibodies (e.g., bispecific antibodies), and antibody fragments so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352:624-628 and Marks et al. (1991) *J. Mol. Biol.* 222:581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) *Proc. Natl. Acad. Sci. USA* 81:6851-6855).

"Humanized" forms of non-human (e.g., murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al. (1986) *Nature* 321:522-525; Riechmann et al. (1988) *Nature* 332:323-329; and Presta (1992) *Curr. Op. Struct. Biol.* 2:593-596.

A "species-dependent antibody" is one which has a stronger binding affinity for an antigen from a first mammalian species than it has for a homologue of that antigen from a second mammalian species. Normally, the species-dependent antibody "binds specifically" to a human antigen (i.e. has a binding affinity ($K_d$) value of no more than about $1 \times 10^{-7}$ M, preferably no more than about $1 \times 10^{-8}$ M and most preferably no more than about $1 \times 10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but preferably is a humanized or human antibody.

As used herein, "antibody mutant" or "antibody variant" refers to an amino acid sequence variant of the species-dependent antibody wherein one or more of the amino acid residues of the species-dependent antibody have been modified. Such mutants necessarily have less than 100% sequence identity or similarity with the species-dependent antibody. In a preferred embodiment, the antibody mutant will have an amino acid sequence having at least 75% amino acid sequence identity or similarity with the amino acid sequence of either the heavy or light chain variable domain of the species-dependent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e same residue) or similar (i.e. amino acid residue from the same group based on common side-chain properties, see below) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, "antibody variable domain" refers to the portions of the light and heavy chains of antibody molecules that include amino acid sequences of Complementarity Determining Regions (CDRs; ie., CDR1, CDR2, and CDR3), and Framework Regions (FRs). $V_H$ refers to the variable domain of the heavy chain. $V_L$ refers to the variable domain of the light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

As used herein, the term "Complementarity Determining Regions (CDRs; ie., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk (1987) *J. Mol. Biol.* 196:901-917). In some instances, a complementarity determining region can include amino acids from both a CDR region defined according to Kabat and a hypervariable loop. For example, the CDRH1 of the heavy chain of antibody 4D5 includes amino acids 26 to 35.

"Framework regions" (hereinafter FR) are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

As used herein, "codon set" refers to a set of different nucleotide triplet sequences used to encode desired variant amino acids. A set of oligonucleotides can be synthesized, for example, by solid phase synthesis, including sequences that represent all possible combinations of nucleotide triplets provided by the codon set and that will encode the desired group of amino acids. A standard form of codon designation is that of the IUB code, which is known in the art and described herein. A codon set typically is represented by 3 capital letters in italics, eg. NNK, NNS, XYZ DVK and the like. A "non-random codon set", as used herein, thus refers to a codon set that encodes select amino acids that fulfill partially, preferably completely, the criteria for amino acid selection as described herein. Synthesis of oligonucleotides with selected nucleotide "degeneracy" at certain positions is well known in that art, for example the TRIM approach (Knappek et al. (1999) *J. Mol. Biol.* 296:57-86); Garrard & Henner (1993)

*Gene* 128:103). Such sets of oligonucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can, but does not necessarily, include restriction enzyme sites useful for, for example, cloning purposes.

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

The "Fab" fragment contains a variable and constant domain of the light chain and a variable domain and the first constant domain (CH1) of the heavy chain. $F(ab')_2$ antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the $V_H$ and $V_L$ domains of antibody, wherein these domains are present in a single polypeptide chain. Generally the Fv polypeptide further comprises a polypeptide linker between the $V_H$ and $V_L$ domains, which enables the scFv to form the desired structure for antigen binding. For a review of scFv, see Pluckthun in *The Pharmacology of Monoclonal Antibodies*, Vol 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444-6448.

The expression "linear antibodies" refers to the antibodies described in Zapata et al. (1995 *Protein Eng*, 8(10):1057-1062). Briefly, these antibodies comprise a pair of tandem Fd segments ($V_H$-$C_H$1-$V_H$-$C_H$1) which, together with complementary light chain polypeptides, form a pair of antigen binding regions. Linear antibodies can be bispecific or monospecific.

As used herein, "library" refers to a plurality of antibody or antibody fragment sequences (for example, polypeptides of the invention), or the nucleic acids that encode these sequences, the sequences being different in the combination of variant amino acids that are introduced into these sequences according to the methods of the invention.

"Phage display" is a technique by which variant polypeptides are displayed as fusion proteins to at least a portion of coat protein on the surface of phage, e.g., filamentous phage, particles. A utility of phage display lies in the fact that large libraries of randomized protein variants can be rapidly and efficiently sorted for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman (1992) *Curr. Opin. Struct Biol*. 3:355-362, and references cited therein. In a monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells (1991) *Methods: A companion to Methods in Enzymology* 3:205-0216.

A "phagemid" is a plasmid vector having a bacterial origin of replication, e.g., ColE1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

As used herein, "solvent accessible position" refers to a position of an amino acid residue in the variable regions of the heavy and light chains of a source antibody or antigen binding fragment that is determined, based on structure, ensemble of structures and/or modeled structure of the antibody or antigen binding fragment, as potentially available for solvent access and/or contact with a molecule, such as an antibody-specific antigen. These positions are typically found in the CDRs and on the exterior of the protein. The solvent accessible positions of an antibody or antigen binding fragment, as defined herein, can be determined using any of a number of algorithms known in the art. Preferably, solvent accessible positions are determined using coordinates from a 3-dimensional model of an antibody, preferably using a computer program such as the InsightII program (Accelrys, San Diego, Calif.). Solvent accessible positions can also be determined using algorithms known in the art (e.g., Lee and Richards (1971) *J. Mol. Biol*. 55, 379 and Connolly (1983) *J. Appl. Cryst*. 16, 548). Determination of solvent accessible positions can be performed using software suitable for protein modeling and 3-dimensional structural information obtained from an antibody. Software that can be utilized for these purposes includes SYBYL Biopolymer Module software (Tripos Associates). Generally and preferably, where an algorithm (program) requires a user input size parameter, the "size" of a probe which is used in the calculation is set at about 1.4 Angstrom or smaller in radius. In addition, determination of solvent accessible regions and area methods using software for personal computers has been described by Pacios (1994) *Comput. Chem.* 18(4): 377-386.

An "angiogenic factor or agent" is a growth factor which stimulates the development of blood vessels, e.g., promote angiogenesis, endothelial cell growth, stability of blood vessels, and/or vasculogenesis, etc. For example, angiogenic factors, include, but are not limited to, e.g., VEGF and members of the VEGF family, PlGF, PDGF family, fibroblast growth factor family (FGFs), TIE ligands (Angiopoietins), ephrins, Del-1, fibroblast growth factors: acidic (aFGF) and basic (bFGF), Follistatin, Granulocyte colony-stimulating factor (G-CSF), Hepatocyte growth factor (HGF)/scatter factor (SF), Interleukin-8 (IL-8), Leptin, Midkine, neuropilins, Placental growth factor, Platelet-derived endothelial cell growth factor (PD-ECGF), Platelet-derived growth factor, especially PDGF-BB or PDGFR-beta, Pleiotrophin (PTN), Progranulin, Proliferin, Transforming growth factor-alpha (TGF-alpha), Transforming growth factor-beta (TGF-beta), Tumor necrosis factor-alpha (TNF-alpha), etc. It would also include factors that accelerate wound healing, such as growth hormone, insulin-like growth factor-I (IGF-I), VIGF, epidermal growth factor (EGF), CTGF and members of its family, and TGF-alpha and TGF-beta. See, e.g., Klagsbrun and D'Amore (1991) *Annu. Rev. Physiol.* 53:217-39; Streit and Detmar (2003) *Oncogene* 22:3172-3179; Ferrara & Alitalo (1999) *Nature Medicine* 5(12):1359-1364; Tonini et al. (2003) *Oncogene* 22:6549-6556 (e.g., Table 1 listing known angiogenic factors); and, Sato (2003) *Int. J. Clin. Oncol.* 8:200-206.

An "anti-angiogenesis agent" or "angiogenesis inhibitor" refers to a small molecular weight substance, an polynucleotide, an polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent as defined above, e.g., antibodies to VEGF-A or to the VEGF-A receptor (e.g., KDR receptor or Flt-1 receptor), anti-PDGFR inhibitors such as Gleevec™ (Imatinib Mesylate). Anti-angiogensis agents also include native angiogenesis inhibitors, e.g., angiostatin, endostatin, etc. See, e.g., Klagsbrun and D'Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12): 1359-1364; Tonini et al. (2003) *Oncogene* 22:6549-6556 (e.g., Table 2 listing known antiangiogenic factors); and, Sato (2003) *Int. J. Clin. Oncol.* 8:200-206 (e.g., Table 1 listing anti-angiogenic agents used in clinical trials).

The term "VEGF" or "VEGF-A" as used herein refers to the 165-amino acid human vascular endothelial cell growth factor and related 121-, 189-, and 206-amino acid human vascular endothelial cell growth factors, as described by Leung et al. (1989) *Science* 246:1306, and Houck et al. (1991) *Mol. Endocrin,* 5:1806, together with the naturally occurring allelic and processed forms thereof. The term "VEGF" also refers to VEGFs from non-human species such as mouse, rat or primate. Sometimes the VEGF from a specific species are indicated by terms such as hVEGF for human VEGF, mVEGF for murine VEGF, and etc. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)" or "VEGF$_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

An "anti-VEGF antibody" is an antibody that binds to VEGF with sufficient affinity and specificity. Preferably, the anti-VEGF antibody of the invention can be used as a therapeutic agent in targeting and interfering with diseases or conditions wherein the VEGF activity is involved. An anti-VEGF antibody will usually not bind to other VEGF homologues such as VEGF-B or VEGF-C, nor other growth factors such as PlGF, PDGF or bFGF. A preferred anti-VEGF antibody is a monoclonal antibody that binds to the same epitope as the monoclonal anti-VEGF antibody A4.6.1 produced by hybridoma ATCC HB 10709. More preferably the anti-VEGF antibody is a recombinant humanized anti-VEGF monoclonal antibody generated according to Presta et al. (1997) *Cancer Res.* 57:4593-4599, including but not limited to the antibody known as bevacizumab (BV; Avastin™).

The anti-VEGF antibody "Bevacizumab (BV)", also known as "rhuMAb VEGF" or "Avastin®, is a recombinant humanized anti-VEGF monoclonal antibody generated according to Presta et al. (1997) *Cancer Res.* 57:4593-4599. It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of Bevacizumab, including most of the framework regions, is derived from human IgG1, and about 7% of the sequence is derived from the murine antibody A4.6.1. Bevacizumab has a molecular mass of about 149,000 daltons and is glycosylated.

A "VEGF antagonist" refers to a molecule capable of neutralizing, blocking, inhibiting, abrogating, reducing or interfering with VEGF activities including, but not limited to, its binding to one or more VEGF receptors. VEGF antagonists include, without limitation, anti-VEGF antibodies and antigen-binding fragments thereof, receptor molecules and derivatives which bind specifically to VEGF thereby sequestering its binding to one or more receptors, anti-VEGF receptor antibodies and VEGF receptor antagonists such as small molecule inhibitors of the VEGFR tyrosine kinases. The term "VEGF antagonist," as used herein, specifically includes molecules, including antibodies, antibody fragments, other binding polypeptides, peptides, and non-peptide small molecules, that bind to neutropilin-1 and/or neutropilin-2 (Nrp-1 and/or Nrp-2) and are capable of neutralizing, blocking, inhibiting, abrogating, reducing or interfering with VEGF activities including, but not limited to, anti-Nrp1 and anti-Nrp2 antibodies and antibodies cross-reacting with Nrp1 and Nrp2, provided they are capable of neutralizing, blocking, inhibiting, abrogating, reducing or interfering with VEGF activities. Thus, the term "VEGF activities" specifically includes neuropilin mediated biological activities (as hereinabove defined) of VEGF.

A "semaphorin antagonists" refers to a molecule capable of neutralizing, blocking, inhibiting, abrogating, reducing or interfering with semaphorin activities including, but not limited to, its binding to one or more semaphorin receptors. Semaphorin antagonists include, without limitation, anti-semaphorin antibodies and antigen-binding fragments thereof, receptor molecules and derivatives which bind specifically to semaphorin thereby sequestering its binding to one or more receptors, anti-semaphorin receptor antibodies and semaphorin receptor antagonists such as small molecule inhibitors of semaphorins. The term "semaphorin antagonist," as used herein, specifically includes molecules, including antibodies, antibody fragments, other binding polypeptides, peptides, and non-peptide small molecules, that bind to neutropilin-1 and/or neutropilin-2 (Nrp-1 and/or Nrp-2) and are capable of neutralizing, blocking, inhibiting, abrogating, reducing or interfering with semaphorin activities including, but not limited to, anti-Nrp1 and anti-Nrp2 antibodies and antibodies cross-reacting with Nrp1 and Nrp2, provided they are capable of neutralizing, blocking, inhibiting, abrogating, reducing or interfering with semaphorin activities. Thus, the term "semaphorin activities" specifically includes neuropilin mediated biological activities (as hereinabove defined) of class 3 semaphorins. Such biological activities include, for example, neurite growth inhibitory effect during embryonic nervous system development and neuron-regeneration.

"Treatment" refers to both therapeutic treatment and prophylactic or preventative measures. Those in need of treatment include those already with the disorder as well as those in which the disorder is to be prevented.

A "disorder" is any condition that would benefit from treatment. For example, mammals who suffer from or need prophylaxis against abnormal angiogenesis (excessive, inappropriate or uncontrolled angiogenesis) or vascular permeability. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, angiogenic and immunologic disorders.

Abnormal angiogenesis occurs when new blood vessels either grow excessively, insufficiently or inappropriately (e.g., the location, timing or onset of the angiogenesis being undesired from a medical standpoint) in a diseased state or such that it causes a diseased state. Excessive, inappropriate or uncontrolled angiogenesis occurs when there is new blood vessel growth that contributes to the worsening of the diseased state or causes a diseased state, such as in cancer, especially vascularized solid tumors and metastatic tumors (including colon, lung cancer (especially small-cell lung cancer), or prostate cancer), diseases caused by ocular neovascularisation, especially diabetic blindness, retinopathies, primarily diabetic retinopathy or age-related macular degeneration (AMD), psoriasis, psoriatic arthritis, haemangioblastoma such as haemangioma; inflammatory renal diseases, such as glomerulonephritis, especially mesangioproliferative glomerulonephritis, haemolytic uremic syndrome, diabetic nephropathy or hypertensive nephrosclerosis; various inflammatory diseases, such as arthritis, especially rheumatoid arthritis, inflammatory bowel disease, psoriasis, sarcoidosis, arterial arteriosclerosis and diseases occurring after transplants, endometriosis or chronic asthma and more than 70 other conditions. The new blood vessels can feed the diseased tissues, destroy normal tissues, and in the case of cancer, the new vessels can allow tumor cells to escape into the circulation and lodge in other organs (tumor metastases). Insufficient angiogenesis occurs when there is inadequate blood vessels growth that contributes to the worsening of a diseased state, e.g., in diseases such as coronary artery disease, stroke, and delayed wound healing. Further, ulcers, strokes, and heart attacks can result from the absence of angiogenesis that normally required for natural healing. The present invention contemplates treating those patients that are at risk of developing the above-mentioned illnesses.

Other patients that are candidates for receiving the antibodies or other molecules of this invention have, or are at risk for developing, abnormal proliferation of fibrovascular tissue, acne rosacea, acquired immune deficiency syndrome, artery occlusion, atopic keratitis, bacterial ulcers, Bechets disease, blood borne tumors, carotid obstructive disease, choroidal neovascularization, chronic inflammation, chronic retinal detachment, chronic uveitis, chronic vitritis, contact lens overwear, corneal graft rejection, corneal neovascularization, corneal graft neovascularization, Crohn's disease, Eales disease, epidemic keratoconjunctivitis, fungal ulcers, Herpes simplex infections, Herpes zoster infections, hyperviscosity syndromes, Kaposi's sarcoma, leukemia, lipid degeneration, Lyme's disease, marginal keratolysis, Mooren ulcer, Mycobacteria infections other than leprosy, myopia, ocular neovascular disease, optic pits, Osler-Weber syndrome (Osler-Weber-Rendu, osteoarthritis, Pagets disease, pars planitis, pemphigoid, phylectenulosis, polyarteritis, post-laser complications, protozoan infections, pseudoxanthoma elasticum, pterygium keratitis sicca, radial keratotomy, retinal neovascularization, retinopathy of prematurity, retrolental fibroplasias, sarcoid, scleritis, sickle cell anemia, Sogrens syndrome, solid tumors, Stargarts disease, Steven's Johnson disease, superior limbic keratitis, syphilis, systemic lupus, Terrien's marginal degeneration, toxoplasmosis, trauma, tumors of Ewing sarcoma, tumors of neuroblastoma, tumors of osteosarcoma, tumors of retinoblastoma, tumors of rhabdomyosarcoma, ulcerative colitis, vein occlusion, Vitamin A deficiency and Wegeners sarcoidosis, undesired angiogenesis associated with diabetes, parasitic diseases, abnormal wound healing, hypertrophy following surgery, injury or trauma, inhibition of hair growth, inhibition of ovulation and corpus luteum formation, inhibition of implantation and inhibition of embryo development in the uterus.

Anti-angiogenesis therapies are useful in the general treatment of graft rejection, lung inflammation, nephrotic syndrome, preeclampsia, pericardial effusion, such as that associated with pericarditis, and pleural effusion, diseases and disorders characterized by undesirable vascular permeability, e.g., edema associated with brain tumors, ascites associated with malignancies, Meigs' syndrome, lung inflammation, nephrotic syndrome, pericardial effusion, pleural effusion, permeability associated with cardiovascular diseases such as the condition following myocardial infarctions and strokes and the like.

Other angiogenesis-dependent diseases according to this invention include angiofibroma (abnormal blood of vessels which are prone to bleeding), neovascular glaucoma (growth of blood vessels in the eye), arteriovenous malformations (abnormal communication between arteries and veins), nonunion fractures (fractures that will not heal), atherosclerotic plaques (hardening of the arteries), pyogenic granuloma (common skin lesion composed of blood vessels), scleroderma (a form of connective tissue disease), hemangioma (tumor composed of blood vessels), trachoma (leading cause of blindness in the third world), hemophilic joints, vascular adhesions and hypertrophic scars (abnormal scar formation).

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

The term "anti-neoplastic composition" refers to a composition useful in treating cancer comprising at least one active therapeutic agent, e.g., "anti-cancer agent." Examples of therapeutic agents (anti-cancer agents) include, but are limited to, e.g., chemotherapeutic agents, growth inhibitory agents, cytotoxic agents, agents used in radiation therapy, anti-angiogenesis agents, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew (1994) *Chem Intl. Ed. Engl.* 33:183-186); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin);

topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (Tarceva™)) and VEGF-A that reduce cell proliferation and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON™ toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman (1986) "Prodrugs in Cancer Chemotherapy" *Biochemical Society Transactions*, 14, pp. 375-382, 615th Meeting Belfast and Stella et al. (1985). "Prodrugs: A Chemical Approach to Targeted Drug Delivery," *Directed Drug Delivery*, Borchardt et al, (ed.), pp. 247-267, Humana Press. The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

Diseases and conditions that can be treated with semaphorin antagonists include, without limitation, neurological diseases and diseases requiring or benefiting from neuroregeneration.

A "small molecule" is defined herein to have a molecular weight below about 500 Daltons.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

MODES FOR CARRYING OUT THE INVENTION

Based on the domain architecture and the functional properties, the extra-cellular domains of Nrps are typically divided into three functional units: a1a2, b1b2, and c, representing their primary semaphorin-binding, VEGF-binding, and dimerization regions, respectively (Ellis, L. M., *Mol Cancer Ther* 5, 1099-107 (2006)). Although structure-function studies delineate the overall domain requirements for neuropilin function, the molecular details of these receptor/ligand complexes remain poorly understood. To date, structural information of Nrps is limited to the b1b2 domain of Nrp1 (Vander Kooi et al., supra; Lee, C. et al., *J Biol Chem* 281, 5702-10 (2006)). The crystal structure of Nrp1 b1b2 in complex with Tuftsin, a tetrapeptide homologous to the C-terminus of $VEGF_{165}$, provided the first structural information on the interaction of Nrp with its binding partner VEGF (Vander Kooi, et al., supra; von Wronski, M. A., et al., *J. Biol Chem* 281, 5702-10 (2006)).

The present invention provides the crystal structure of Nrp2 a1a2b1b2 in complex with a Fab fragment of an antibody that can block Sema3 binding to both Nrp1 and Nrp2 in vitro. Structures of the a2b1b2 and b1b2 fragments of both Nrp isoforms are also compared and contrasted. In addition, the structure of the b1 domain of Nrp1 combined with the Fab fragment of a recently described phage-derived antibody that specifically inhibits VEGF$_{165}$ binding to Nrp1 in vivo (Liang, W. C., et al., *J Mol Biol* 366, 815-29 (2007); Pan, Q et al., *Cancer Cell* 11, 53-67 (2007) is also provided and evaluated. Together, these structures present a detailed picture of a large portion of the Nrp extracellular domain and suggest models for VEGF and semaphorin binding. Based on a Nrp2 dimer present in two different crystal forms, a novel mechanism is proposed for Nrp dimerization and ligand binding.

Details of the crystallograhic studies are provided in the Examples below. General methods for producing anti-NRP antibodies are described herein and in Example 1.

Production of Anti-NRP Antibodies

The invention herein includes the production and use of anti-NRP antibodies. Exemplary methods for generating antibodies are described in more detail in the following sections.

Anti-NRP antibodies are selected using an NRP (e.g. NRP1 and/or NRP2) antigen derived from a mammalian species. Preferably the antigen is human NRP (hNRP). However, NRPs from other species such as murine NRP (mNRP) can also be used as the target antigen. The NRP antigens from various mammalian species may be isolated from natural sources. In other embodiments, the antigen is produced recombinantly or made using other synthetic methods known in the art.

The antibody selected will normally have a sufficiently strong binding affinity for the NRP antigen. For example, the antibody may bind hNRP with a $K_d$ value of no more than about 5 nM, preferably no more than about 2 nM, and more preferably no more than about 500 pM. Antibody affinities may be determined by a surface plasmon resonance based assay (such as the BIAcore assay as described in Examples); enzyme-linked immunoabsorbent assay (ELISA); and competition assays (e.g. RIA's), for example.

Also, the antibody may be subject to other biological activity assays, e.g., in order to evaluate its effectiveness as a therapeutic. Such assays are known in the art and depend on the target antigen and intended use for the antibody. Examples include the HUVEC inhibition assay (as described in the Examples below); tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062).

To screen for antibodies which bind to a particular epitope on the antigen of interest, a routine cross-blocking assay such as that described in *Antibodies, A Laboratory Manual*, Cold Spring Harbor Laboratory, Ed Harlow and David Lane (1988), can be performed. Alternatively, epitope mapping, e.g. as described in Champe et al. (1995) *J. Biol. Chem.* 270:1388-1394, can be performed to determine whether the antibody binds an epitope of interest.

Generation of Anti-NRP Antibodies from Synthetic Antibody Phage Libraries

In a preferred embodiment, the anti-NRP antibodies are selected using a unique phage display approach. The approach involves generation of synthetic antibody phage libraries based on single framework template, design of sufficient diversities within variable domains, display of polypeptides having the diversified variable domains, selection of candidate antibodies with high affinity to target NRP antigen, and isolation of the selected antibodies.

Details of the phage display methods can be found, for example, in WO03/102157 published Dec. 11, 2003.

In one aspect, the antibody libraries can be generated by mutating the solvent accessible and/or highly diverse positions in at least one CDR of an antibody variable domain. Some or all of the CDRs can be mutated using the methods provided herein. In some embodiments, it may be preferable to generate diverse antibody libraries by mutating positions in CDRH1, CDRH2 and CDRH3 to form a single library or by mutating positions in CDRL3 and CDRH3 to form a single library or by mutating positions in CDRL3 and CDRH1, CDRH2 and CDRH3 to form a single library.

A library of antibody variable domains can be generated, for example, having mutations in the solvent accessible and/or highly diverse positions of CDRH1, CDRH2 and CDRH3. Another library can be generated having mutations in CDRL1, CDRL2 and CDRL3. These libraries can also be used in conjunction with each other to generate binders of desired affinities. For example, after one or more rounds of selection of heavy chain libraries for binding to a target antigen, a light chain library can be replaced into the population of heavy chain binders for further rounds of selection to increase the affinity of the binders.

Preferably, a library is created by substitution of original amino acids with variant amino acids in the CDRH3 region of the variable region of the heavy chain sequence. The resulting library can contain a plurality of antibody sequences, wherein the sequence diversity is primarily in the CDRH3 region of the heavy chain sequence.

In one aspect, the library is created in the context of the humanized antibody 4D5 sequence, or the sequence of the framework amino acids of the humanized antibody 4D5 sequence. Preferably, the library is created by substitution of at least residues 95-100a of the heavy chain with amino acids encoded by the DVK codon set, wherein the DVK codon set is used to encode a set of variant amino acids for every one of these positions. An example of an oligonucleotide set that is useful for creating these substitutions comprises the sequence (DVK)$_7$. In some embodiments, a library is created by substitution of residues 95-100a with amino acids encoded by both DVK and NNK codon sets. An example of an oligonucleotide set that is useful for creating these substitutions comprises the sequence (DVK)$_6$ (NNK). In another embodiment, a library is created by substitution of at least residues 95-100a with amino acids encoded by both DVK and NNK codon sets. An example of an oligonucleotide set that is useful for creating these substitutions comprises the sequence (DVK)$_5$ (NNK). Another example of an oligonucleotide set that is useful for creating these substitutions comprises the sequence (NNK)$_6$. Other examples of suitable oligonucleotide sequences can be determined by one skilled in the art according to the criteria described herein.

In another embodiment, different CDRH3 designs are utilized to isolate high affinity binders and to isolate binders for a variety of epitopes. The range of lengths of CDRH3 generated in this library is 11 to 13 amino acids, although lengths different from this can also be generated. H3 diversity can be expanded by using NNK, DVK and NVK codon sets, as well as more limited diversity at N and/or C-terminal.

Diversity can also be generated in CDRH1 and CDRH2. The designs of CDR-H1 and H2 diversities follow the strategy of targeting to mimic natural antibodies repertoire as described with modification that focus the diversity more closely matched to the natural diversity than previous design.

For diversity in CDRH3, multiple libraries can be constructed separately with different lengths of H3 and then combined to select for binders to target antigens. The multiple libraries can be pooled and sorted using solid support selection and solution sorting methods as described previously and herein below. Multiple sorting strategies may be employed. For example, one variation involves sorting on target bound to a solid, followed by sorting for a tag that may be present on the fusion polypeptide (eg. anti-gD tag) and followed by another sort on target bound to solid. Alternatively, the libraries can be sorted first on target bound to a solid surface, the eluted binders are then sorted using solution phase binding with decreasing concentrations of target antigen. Utilizing combinations of different sorting methods provides for minimization of selection of only highly expressed sequences and provides for selection of a number of different high affinity clones.

High affinity binders for the target NRP antigen can be isolated from the libraries. Limiting diversity in the H1/H2 region decreases degeneracy about $10^4$ to $10^5$ fold and allowing more H3 diversity provides for more high affinity binders. Utilizing libraries with different types of diversity in CDRH3 (eg. utilizing DVK or NVT) provides for isolation of binders that may bind to different epitopes of a target antigen.

Of the binders isolated from the pooled libraries as described above, it has been discovered that affinity may be further improved by providing limited diversity in the light chain. Light chain diversity is generated in this embodiment as follows in CDRL1: amino acid position 28 is encoded by RDT; amino acid position 29 is encoded by RKT; amino acid position 30 is encoded by RVW; amino acid position 31 is encoded by ANW; amino acid position 32 is encoded by THT; optionally, amino acid position 33 is encoded by CTG; in CDRL2: amino acid position 50 is encoded by KBG; amino acid position 53 is encoded by AVC; and optionally, amino acid position 55 is encoded by GMA; in CDRL3: amino acid position 91 is encoded by TMT or SRT or both; amino acid position 92 is encoded by DMC; amino acid position 93 is encoded by RVT; amino acid position 94 is encoded by NHT; and amino acid position 96 is encoded by TWT or YKG or both.

In another embodiment, a library or libraries with diversity in CDRH1, CDRH2 and CDRH3 regions is generated. In this embodiment, diversity in CDRH3 is generated using a variety of lengths of H3 regions and using primarily codon sets XYZ and NNK or NNS. Libraries can be formed using individual oligonucleotides and pooled or oligonucleotides can be pooled to form a subset of libraries. The libraries of this embodiment can be sorted against target bound to solid. Clones isolated from multiple sorts can be screened for specificity and affinity using ELISA assays. For specificity, the clones can be screened against the desired target antigens as well as other nontarget antigens. Those binders to the target NRP1 antigen can then be screened for affinity in solution binding competition ELISA assay or spot competition assay. High affinity binders can be isolated from the library utilizing XYZ codon sets prepared as described above. These binders can be readily produced as antibodies or antigen binding fragments in high yield in cell culture.

In some embodiments, it may be desirable to generate libraries with a greater diversity in lengths of CDRH3 region. For example, it may be desirable to generate libraries with CDRH3 regions ranging from about 7 to 19 amino acids.

High affinity binders isolated from the libraries of these embodiments are readily produced in bacterial and eukaryotic cell culture in high yield. The vectors can be designed to readily remove sequences such as gD tags, viral coat protein component sequence, and/or to add in constant region sequences to provide for production of full length antibodies or antigen binding fragments in high yield.

A library with mutations in CDRH3 can be combined with a library containing variant versions of other CDRs, for example CDRL1, CDRL2, CDRL3, CDRH1 and/or CDRH2. Thus, for example, in one embodiment, a CDRH3 library is combined with a CDRL3 library created in the context of the humanized 4D5 antibody sequence with variant amino acids at positions 28, 29, 30, 31, and/or 32 using predetermined codon sets. In another embodiment, a library with mutations to the CDRH3 can be combined with a library comprising variant CDRH1 and/or CDRH2 heavy chain variable domains. In one embodiment, the CDRH1 library is created with the humanized antibody 4D5 sequence with variant amino acids at positions 28, 30, 31, 32 and 33. A CDRH2 library may be created with the sequence of humanized antibody 4D5 with variant amino acids at positions 50, 52, 53, 54, 56 and 58 using the predetermined codon sets.

Anti-NRP Antibody Mutants

The anti-NRP antibody generated from phage libraries can be further modified to generate antibody mutants with improved physical, chemical and or biological properties over the parent antibody. Where the assay used is a biological activity assay, the antibody mutant preferably has a biological activity in the assay of choice which is at least about 10 fold better, preferably at least about 20 fold better, more preferably at least about 50 fold better, and sometimes at least about 100 fold or 200 fold better, than the biological activity of the parent antibody in that assay. For example, an anti-NRP1 antibody mutant preferably has a binding affinity for NRP which is at least about 10 fold stronger, preferably at least about 20 fold stronger, more preferably at least about 50 fold stronger, and sometimes at least about 100 fold or 200 fold stronger, than the binding affinity of the parent anti-NRP antibody.

To generate the antibody mutant, one or more amino acid alterations (e.g. substitutions) are introduced in one or more of the hypervariable regions of the parent antibody. Alternatively, or in addition, one or more alterations (e.g. substitutions) of framework region residues may be introduced in the parent antibody where these result in an improvement in the binding affinity of the antibody mutant for the antigen from the second mammalian species. Examples of framework region residues to modify include those which non-covalently bind antigen directly (Amit et al. (1986) *Science* 233:747-753); interact with/effect the conformation of a CDR (Chothia et al. (1987) *J. Mol. Biol.* 196:901-917); and/or participate in the $V_L$-$V_H$ interface (EP 239 400B1). In certain embodiments, modification of one or more of such framework region residues results in an enhancement of the binding affinity of the antibody for the antigen from the second mammalian species. For example, from about one to about five framework residues may be altered in this embodiment of the invention. Sometimes, this may be sufficient to yield an antibody mutant suitable for use in preclinical trials, even where none of the hypervariable region residues have been altered. Normally, however, the antibody mutant will comprise additional hypervariable region alteration(s).

The hypervariable region residues which are altered may be changed randomly, especially where the starting binding affinity of the parent antibody is such that such randomly produced antibody mutants can be readily screened.

One useful procedure for generating such antibody mutants is called "alanine scanning mutagenesis" (Cunningham and Wells (1989) *Science* 244:1081-1085). Here, one or more of the hypervariable region residue(s) are replaced by alanine or polyalanine residue(s) to affect the interaction of the amino acids with the antigen from the second mammalian species. Those hypervariable region residue(s) demonstrating functional sensitivity to the substitutions then are refined by introducing further or other mutations at or for the sites of substitution. Thus, while the site for introducing an amino acid sequence variation is predetermined, the nature of the mutation per se need not be predetermined. The ala-mutants produced this way are screened for their biological activity as described herein.

Normally one would start with a conservative substitution such as those shown below under the heading of "preferred substitutions". If such substitutions result in a change in biological activity (e.g. binding affinity), then more substantial changes, denominated "exemplary substitutions" in the following table, or as further described below in reference to amino acid classes, are introduced and the products screened.
Preferred Substitutions:

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Even more substantial modifications in the antibodies biological properties are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr, asn, gln;
(3) acidic: asp, glu;
(4) basic: his, lys, arg;
(5) residues that influence chain orientation: gly, pro; and
(6) aromatic: trp, tyr, phe.

Non-conservative substitutions will entail exchanging a member of one of these classes for another class.

In another embodiment, the sites selected for modification are affinity matured using phage display (see above).

Nucleic acid molecules encoding amino acid sequence mutants are prepared by a variety of methods known in the art. These methods include, but are not limited to, oligonucleotide-mediated (or site-directed) mutagenesis, PCR mutagenesis, and cassette mutagenesis of an earlier prepared mutant or a non-mutant version of the parent antibody. The preferred method for making mutants is site directed mutagenesis (see, e.g., Kunkel (1985) *Proc. Natl. Acad. Sci. USA* 82:488).

In certain embodiments, the antibody mutant will only have a single hypervariable region residue substituted. In other embodiments, two or more of the hypervariable region residues of the parent antibody will have been substituted, e.g. from about two to about ten hypervariable region substitutions.

Ordinarily, the antibody mutant with improved biological properties will have an amino acid sequence having at least 75% amino acid sequence identity or similarity with the amino acid sequence of either the heavy or light chain variable domain of the parent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e same residue) or similar (i.e. amino acid residue from the same group based on common side-chain properties, see above) with the parent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

Following production of the antibody mutant, the biological activity of that molecule relative to the parent antibody is determined. As noted above, this may involve determining the binding affinity and/or other biological activities of the antibody. In a preferred embodiment of the invention, a panel of antibody mutants is prepared and screened for binding affinity for the antigen such as NRP1 or a fragment thereof. One or more of the antibody mutants selected from this initial screen are optionally subjected to one or more further biological activity assays to confirm that the antibody mutant(s) with enhanced binding affinity are indeed useful, e.g. for preclinical studies.

The antibody mutant(s) so selected may be subjected to further modifications, oftentimes depending on the intended use of the antibody. Such modifications may involve further alteration of the amino acid sequence, fusion to heterologous polypeptide(s) and/or covalent modifications such as those elaborated below. With respect to amino acid sequence alterations, exemplary modifications are elaborated above. For example, any cysteine residue not involved in maintaining the proper conformation of the antibody mutant also may be substituted, generally with serine, to improve the oxidative stability of the molecule and prevent aberrant cross linking. Conversely, cysteine bond(s) may be added to the antibody to improve its stability (particularly where the antibody is an antibody fragment such as an Fv fragment). Another type of amino acid mutant has an altered glycosylation pattern. This may be achieved by deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Vectors, Host Cells and Recombinant Methods

The anti-Nrp antibodies of the invention can be produced recombinantly, using techniques and materials readily obtainable.

For recombinant production of an anti-NRP antibody, the nucleic acid encoding it is isolated and inserted into a replicable vector for further cloning (amplification of the DNA) or for expression. DNA encoding the antibody is readily isolated or synthethized using conventional procedures (e.g., by using oligonucleotide probes that are capable of binding specifically to DNAs encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(i) Signal Sequence Component

The antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native antibody signal sequence, the signal sequence is substituted by a prokaryotic signal sequence selected, for example, from the group of the alkaline phosphatase, penicillinase, 1 pp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2µ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al. (1979) *Nature* 282:39). The trp1 gene provides a selection marker for a mutant strain of yeast lacking the ability to grow in tryptophan, for example, ATCC No. 44076 or PEP4-1. Jones (1977) *Genetics* 85:12. The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 µm circular plasmid pKD1 can be used for transformation of *Kluyveromyces* yeasts. Alternatively, an expression system for large-scale production of recombinant calf chymosin was reported for *K. lactis*. Van den Berg (1990) *Bio/Technology* 8:135. Stable multi-copy expression vectors for secretion of mature recombinant human serum albumin by industrial strains of *Kluyveromyces* have also been disclosed. Fleer et al. (1991) *Bio/Technology* 9:968-975.

(iv) Promoter Component

Expression and cloning vectors usually contain a promoter that is recognized by the host organism and is operably linked to the antibody nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419, 446. A modification of this system is described in U.S. Pat. No. 4,601,978. See also Reyes et al. (1982) *Nature* 297:598-601 on expression of human β-interferon cDNA in mouse cells under the control of a thymidine kinase promoter from herpes simplex virus. Alternatively, the rous sarcoma virus long terminal repeat can be used as the promoter.

(v) Enhancer Element Component

Transcription of a DNA encoding the antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv (1982) *Nature* 297:17-18 on enhancing elements for activation of eukaryotic promoters. The enhancer may be spliced into the vector at a position 5' or 3' to the antibody-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al. (1977) *J. Gen Virol.* 36:59); baby hamster kidney cells (BHK, ATCC CCL 10); Chinese hamster ovary cells/–DHFR (CHO, Urlaub et al. (1980) *Proc. Natl. Acad. Sci. USA* 77:4216); mouse sertoli cells (TM4, Mather (1980) *Biol. Reprod.* 23:243-251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al. (1982) *Annals N.Y. Acad. Sci.* 383:44-68); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al. (1979) *Meth. Enz.* 58:44, Barnes et al. (1980) *Anal. Biochem.* 102:255, U.S. Pat. Nos. 4,767,704; 4,657,866; 4,927,762; 4,560,655; or 5,122,469; WO 90/03430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Antibody Purification

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al. (1992) *Bio/Technology* 10:163-167 describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al. (1983) *J. Immunol. Meth.* 62:1-13). Protein G is recommended for all mouse isotypes and for human γ3 (Guss et al. (1986) *EMBO J.* 5:15671575). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Formulations

Therapeutic formulations of the antibody are prepared for storage by mixing the antibody having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Therapeutic Uses

It is contemplated that the antibody of the present invention may be used to treat a mammal. In one embodiment, the antibody is administered to a nonhuman mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the antibody or may be used to study toxicity of the antibody of interest. In each of these embodiments, dose escalation studies may be performed in the mammal. Where the antibody is an anti-NRP1 antibody, it may be administered to a host rodent in a solid tumor model, for example.

In addition, or in the alternative, the antibody is used to treat a human, e.g. a patient suffering from a disease or disorder who could benefit from administration of the antibody.

The present invention encompasses antiangiogenic cancer therapy, a novel cancer treatment strategy aimed at inhibiting the development of tumor blood vessels required for providing nutrients to support tumor growth. Because angiogenesis is involved in both primary tumor growth and metastasis, the antiangiogenic treatment provided by the invention is capable of inhibiting the neoplastic growth of tumor at the primary site as well as preventing metastasis of tumors at the secondary sites, therefore allowing attack of the tumors by other therapeutics. Examples of cancer to be treated herein include, but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. More particularly, cancers that are amenable to treatment by the antibodies of the invention include breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, melanoma, ovarian cancer, mesothelioma, and multiple myeloma.

It is contemplated that when used to treat various diseases such as tumors, the antibodies of the invention can be combined with other therapeutic agents suitable for the same or similar diseases. When used for treating cancer, antibodies of the present invention may be used in combination with conventional cancer therapies, such as surgery, radiotherapy, chemotherapy or combinations thereof.

In certain aspects, other therapeutic agents useful for combination cancer therapy with the antibody of the invention include other anti-angiogenic agents. Many anti-angiogenic agents have been identified and are known in the arts, including those listed by Carmeliet and Jain (2000).

In one aspect, the antibody of the invention is used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof. Alternatively, or in addition, two or more anti-NRP1 antibodies may be co-administered to the patient. In a more preferred embodiment, the anti-NRP1$^A$ or anti-NRP$^B$ antibody of the invention is used in combination with an anti-VEGF antibody to generate additive or synergistic effects. Preferred anti-VEGF antibodies include those that bind to the same epitope as the anti-hVEGF antibody A4.6.1. More preferably the anti-VEGF antibody is bevacizumab or ranibizumab.

In some other aspects, other therapeutic agents useful for combination tumor therapy with the antibody of the invention include antagonist of other factors that are involved in tumor growth, such as EGFR, ErbB2 (also known as Her2) ErbB3, ErbB4, or TNF. Preferably, the anti-NRP1 antibody of the invention can be used in combination with small molecule receptor tyrosine kinase inhibitors (RTKIs) that target one or more tyrosine kinase receptors such as VEGF receptors, FGF receptors, EGF receptors and PDGF receptors. Many therapeutic small molecule RTKIs are known in the art, including, but are not limited to, vatalanib (PTK787), erlotinib (TARCEVA®), OSI-7904, ZD6474 (ZACTIMA®), ZD6126 (ANG453), ZD1839, sunitinib (SUTENT®), semaxanib (SU5416), AMG706, AG013736, Imatinib (GLEEVEC®), MLN-518, CEP-701, PKC-412, Lapatinib (GSK572016), VELCADE®, AZD2171, sorafenib (NEXAVAR®), XL880, and CHIR-265.

The anti-Nrp antibody of the invention, either alone or in combination with a second therapeutic agent (such as an anti-VEGF antibody) can be further used in combination with one or more chemotherapeutic agents. A variety of chemotherapeutic agents may be used in the combined treatment methods of the invention. An exemplary and non-limiting list of chemotherapeutic agents contemplated is provided herein under "Definition".

When the anti-Nrp antibody is co-administered with a second therapeutic agent, the second therapeutic agent may be administered first, followed by the anti-Nrp antibody. However, simultaneous administration or administration of the anti-Nrp antibody first is also contemplated. Suitable dosages for the second therapeutic agent are those presently used and may be lowered due to the combined action (synergy) of the agent and anti-Nrp antibody.

For the prevention or treatment of disease, the appropriate dosage of antibody will depend on the type of disease to be treated, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to 50 mg/kg (e.g. 0.1-20 mg/kg) of antibody is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. In a preferred aspect, the antibody of the invention is administered every two to three weeks, at a dose ranged from about 5 mg/kg to about 15 mg/kg. More preferably, such dosing regimen is used in combination with a chemotherapy regimen as the first line therapy for treating metastatic colorectal cancer. In some aspects, the chemotherapy regimen involves the traditional high-dose intermittent administration. In some other aspects, the chemotherapeutic agents are administered using smaller and more frequent doses without scheduled breaks ("metronomic chemotherapy"). The progress of the therapy of the invention is easily monitored by conventional techniques and assays.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat a disease or disorder. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as used hereinbefore or about from 1 to 99% of the heretofore employed dosages. Generally, alleviation or treatment of a disease or disorder involves the lessening of one or more symptoms or medical problems associated with the disease or disorder. In the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. In some embodiments, a composition of this invention can be used to prevent the onset or reoccurrence of the disease or disorder in a subject or mammal.

Non-Therapeutic Uses

The antibodies of the invention may be used as affinity purification agents. In this process, the antibodies are immobilized on a solid phase such a Sephadex resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized antibody. Finally, the support is washed with another suitable solvent, such as glycine buffer, pH 5.0, that will release the antigen from the antibody.

The antibodies of this invention may also be useful in diagnostic assays, e.g., for detecting expression of an antigen of interest in specific cells, tissues, or serum.

For diagnostic applications, the antibody typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al. (1991) Ed. Wiley-Interscience, New York, N.Y., Pubs. for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al. (1981) Methods for the Preparation of Enzyme—Antibody Conjugates for use in Enzyme Immunoassay, in *Methods in Enzym.* (ed J. Langone & H. Van Vunakis), Academic press, New York 73:147-166.

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the antibody need not be labeled, and the presence thereof can be detected using a labeled antibody which binds to the antibody.

The antibodies of the present invention may be employed in any known assay method, such as competitive binding assays, direct and indirect sandwich assays, and immunoprecipitation assays. Zola, *Monoclonal Antibodies: A Manual of Techniques*, pp. 147-158 (CRC Press, Inc. 1987).

Competitive binding assays rely on the ability of a labeled standard to compete with the test sample analyze for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition, so that the standard and analyze that are bound to the antibodies may conveniently be separated from the standard and analyze which remain unbound.

Sandwich assays involve the use of two antibodies, each capable of binding to a different immunogenic portion, or epitope, of the protein to be detected. In a sandwich assay, the test sample analyze is bound by a first antibody which is immobilized on a solid support, and thereafter a second antibody binds to the analyze, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

The antibodies may also be used for in vivo diagnostic assays. Generally, the antibody is labeled with a radionuclide (such as $^{111}$In, $^{99}$Tc, $^{14}$C, $^{131}$I, $^{125}$I, $^{3}$H, $^{32}$P or $^{35}$S) or a dye so that the tumor can be localized using immunoscintigraphy.

In one embodiment, a method of detecting NRP1 in a biological sample (e.g., tissue, blood, sera, spinal fluid) or a prepared biological sample can comprise the step of contacting an antibody of this invention with the sample and observing the anti-NRP1 antibody bound to the NRP1 in the sample or determining the amount of the anti-NRP1 antibody bound to NRP1 in the sample. In another embodiment, a method of detecting NRP1 in a subject comprises the step of administering an antibody of this invention to the subject and observing the anti-NRP1 antibody bound to the NRP1 in the subject or determining the amount of the anti-NRP1 antibody bound to NRP1 in the subject (e.g., human, mouse, rabbit, rat, etc).

Diagnostic Kits

As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Articles of Manufacture

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The following examples are intended merely to illustrate the practice of the present invention and are not provided by way of limitation. The disclosures of all patent and scientific literatures cited herein are expressly incorporated in their entirety by reference.

EXAMPLES

Example 1

Construction and Function of Anti-Nrp1$^B$ and Anti-panNrp$^A$ antibodies

A strategy to develop phage-derived antibodies that selectively block binding of either semaphorin or VEGF to Nrp1 has been reported by Liang et al., *J Mol Biol* 366, 815-29 (2007) and Pan et al., *Cancer Cell* 11, 53-67 (2007). These monoclonal antibodies were designed as tools to discriminate between Nrp1-mediated responses to either ligand and to evaluate their potential as therapeutics in murine tumor models.

In brief, a human synthetic antibody phage library was designed that was built on a single consensus scaffold with VH/VL diversity. Details of the design and selection of this antibody library are described in Liang et al., supra, and can also be found in WO 03/102157 published on Dec. 11, 2003, the entire disclosure of which is incorporated herein by reference. From this library, functional blocking antibodies to human and murine NRP1 were generated. Antibodies mapping to the b1b2 domain of NRP1 could block the binding of VEGF and NRP1, and VEGF-induced HUVEC cell migration. The antibodies identified included a VEGF-blocking antibody (cloneYW107.4.87; anti-Nrp1$^B$) that binds Nrp1 with an affinity of 0.2 nM (Liang et al., supra; Pan et al., supra). Although this antibody blocks the interaction between VEGF and Nrp1, it does not antagonize Sema3A function. In vivo, anti-Nrp1$^B$ not only reduces vascular remodeling in the mouse retina, but also works additively with anti-VEGF therapy to slow tumor growth (Liang et al., supra and Pan et al., supra).

Figure 11:
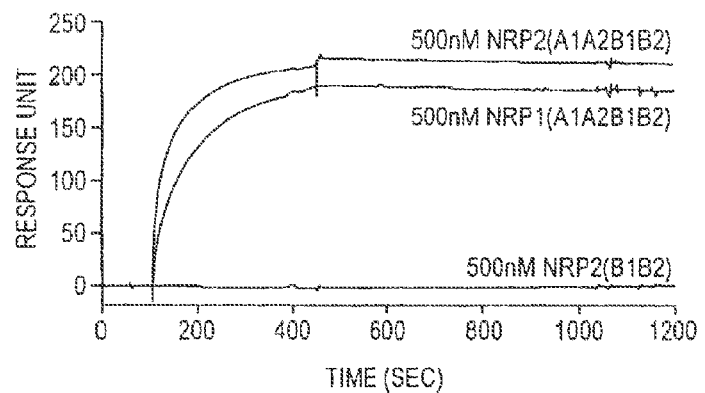
FIG. 11—Analysis of anti-Nrp antibody binding kinetics. BIAcore kinetic analysis of anti-panNrp[4] antibody. The sensograms for injection of 500 nM each human NRP protein at 25° C. over IgG immobilized BIAcore sensor chip demonstrate the binding specificity. anti-panNrp[4] binds Nrp1 and Nrp2 a1a2b1b2, but not the Nrp2 b1b2 domains.

Following the same approach, using a human synthetic antibody phage library built on a single consensus framework, an antibody (clone YW68.11.26, anti-panNrp$^A$) has been developed, which cross-reacts with both Nrp1 and Nrp2 with affinities of 0.21 and 0.15 nM, respectively (FIG. 11). The light and heavy chain variable domain sequences of YW68.11.26 and related YW68.11 are shown in FIGS. 7 and 8, respectively. The amino acid sequences of the Fab fragments of anti-panNrp$^A$ IgG1 antibodies YW68.11 and YW68.11.26 are shown in FIGS. 9A and 9B, respectively.

Figure 1B:
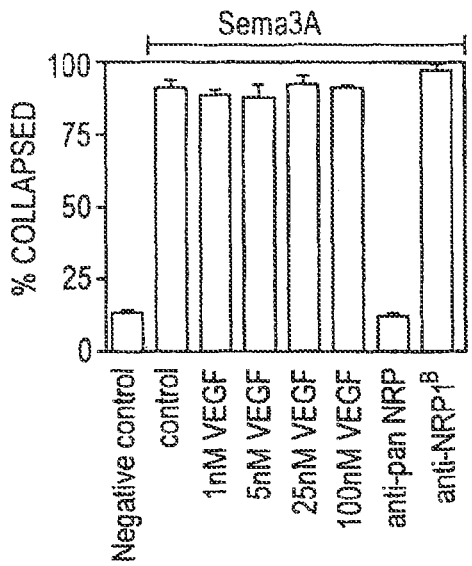

In contrast to anti-Nrp1$^B$, anti-panNrp$^A$ does not affect the binding of VEGF$_{165}$ or VEGF-C (data not shown). Evaluation of the capacity of both antibodies to inhibit the Sema3A-mediated collapse of axon growth cones from murine dorsal root ganglia (DRG) (FIG. 1). The addition of Sema3A results in the retraction of the actin processes with the DRG growth cones; this action is completely antagonized by anti-panNrp$^A$, but not by anti-Nrp1$^B$.

Example 2

Structural Studies of Neuropilin/Antibody Complexes

Materials and Methods

Functional Assays and Antibody Binding Affinities

Collapse assays and determination of anti-Nrp antibody binding affinities were performed as previously described (He, Z and Tessier-Lavigne, M., *Cell* 90, 739-51 (1997); Liang et al., supra and Pan et al., supra.

Protein Expression and Purification for Crystallography Studies

Nrp1-b1, Nrp1-b1b2, and Nrp2-b1b2 (see FIG. 11 for domain boundaries) were cloned into pET15b (Novagen) and expressed in *E. coli* following induction at 37° C. (Nrp1-b1 and -b1b2) or 16° C. (Nrp2-b1b2). All neuropilin type b fragments are expressed as soluble proteins without the need for a re-folding protocol. Following cell lysis, proteins were purified using nickel-nitrilotriacetic acid (Ni-NTA) resin in 50 mM Tris (pH 8.0), 300-500 mM NaCl, and 20 mM imidazole, and eluted in the same buffer plus 250 mM imidazole. The his$_6$-tags were removed with thrombin, and samples were further purified by gel filtration chromatography using a Superdex-75 column equilibrated in 25 mM Tris (pH 8.0) and 150 mM NaCl.

Recombinant baculoviruses were generated to facilitate the secretion of Nrp1-a2b1b2, Nrp2-a2b1b2, Nrp2-a1a2b1b2, and the full-length Nrp2-ECD (FIG. 11) from Hi5 cells. Nrp2-a1a2b1b2 and the full-length Nrp2-ECD were subcloned with the Nrp2 native secretion signal and a C-terminal His$_6$-tag into pENTR/D-TOPO (Invitrogen) and recombined into pDEST8 (Invitrogen) to generate a viral bacmid. Nrp1-a2b1b2 and Nrp2-a2b1b2 were cloned into pAcGP67B (Clonetech). Following infection, the culture media was collected and supplemented with 50 mM Tris (pH 8.0), 5 mM CaCl$_2$, and 1 mM NiCl$_2$; proteins were purified with Ni-NTA and gel filtration chromatography as described for bacterial-expressed neuropilin constructs.

The Fab fragments for anti-Nrp1$^B$ (YW107.4.87) and anti-panNrp$^A$ (YW68.11.26) were expressed in *E. coli*, captured on a Protein G column equilibrated in PBS, and eluted with 0.58% acetic acid. Protein fractions were further purified by ion exchange chromatography (SP-sepharose) in 20 mM MES (pH 5.5) and eluted with a gradient from 0 to 250 mM NaCl. Fab/Nrp complexes were typically mixed at 1:1 molar ratio and further purified using a Superdex-200 column equilibrated in 25 mM Tris-HCl (pH 7.5) and 200 mM NaCl. For crystallization, all unbound neuropilin and Nrp/Fab complex samples were concentrated as detailed in FIG. 11.

Crystallization, Structure Determination, and Refinement

All crystals were obtained by the vapor diffusion method at 19° C. by mixing equal volumes of protein plus well solution (see FIG. 11 for details). For cryoprotection, crystals were generally transferred to a solution of mother liquor plus 20% glycerol or ethylene glycol (FIG. 11). The Nrp1-b1/Fab complex crystals were transferred to 10 mM Hepes (pH 7.2), 25% PEG 1,500, and 10% ethylene glycol; allowed to de-hydrate overnight against 10 mM Hepes (pH 7.2), 25% PEG 1,500, and 20% ethylene glycol; and flash frozen in liquid nitrogen. Data sets were collected at the Advanced Light Source (beam-lines 5.0.1 or 5.0.2) or the Stanford Synchrotron Radiation Laboratory (beam-lines 9-2 or 11-1). Data were processed using Denzo and Scalepack from the HKL Suite (Otwinowski, Z & Minor, W., *Methods in Enzymology* 276, 307-326 (1997). Cell parameters and data statistics are summarized in FIG. 2C.

All crystal structures were solved by molecular replacement using Phaser (McCoy et al., *Acta Crystallogr D Biol Crystallogr* 61, 458-64 (2005). The Nrp1-b1b2 structure was solved using the Nrp1-b1 crystal structure (pdb accession no. 1KEX) (Lee, et al., *Structure* 11, 99-108 (2003)) as a search model for each coagulation factor domain. The refined co-ordinates of the Nrp1-b1b2 structure served as the search probe for the Nrp2-b1b2 structure. The monoclinic form of the Nrp2 a1a2b1b2/anti-panNrp$^A$-Fab complex was solved using the Nrp2-b1b2 structure and Fab fragments containing either the variable domains ($V_H/V_L$) or the constant domains ($C_{H1}/C_L$) from the B20-4/VEGF complex (pdb accession no. 2FJH). The a2 domain was identified by molecular replacement using the N-terminal CUB domain from MASP-2; the a1 domain could not be located by molecular replacement and was placed manually within the electron density. The Nrp1-b1/Fab complex was solved using the Nrp1-b1 crystal structure and the B20-4 Fab fragments described above. All remaining structures were solved using the refined co-ordinates of the b1b2 structures and the a2 CUB domain from the Nrp2-a1a2b1b2/Fab complex. Atomic models were built using Coot (Emsley, P. & Cowtan, K. Coot, *Acta Crystallogr D Biol Crystallogr* 60, 2126-32 (2004)) and refined with Refmac (Murshudov, et al., *Acta Crystallographica* D53, 240-255 (1997)).

Crystallization of Nrp1, Nrp2, and Neurophilin/Fab Complexes

Figure 2A:
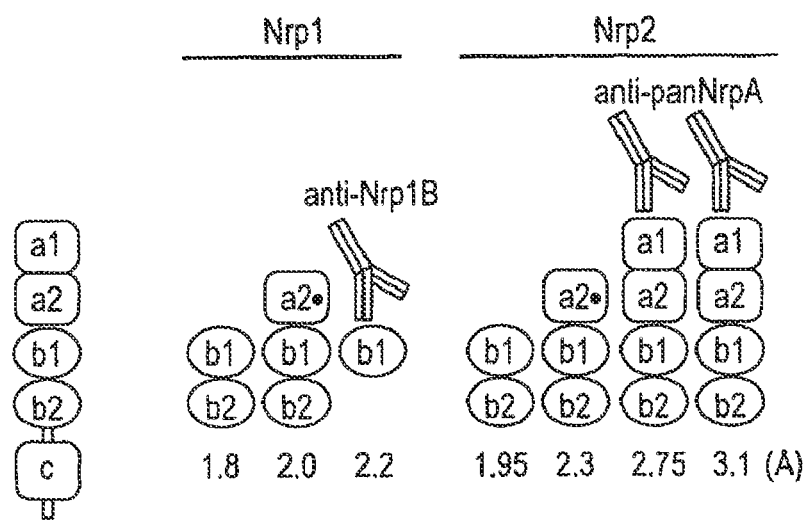
FIG. 2—Summary of the Neuropilin Crystal Structures. A) The Nrp ectodomain is comprised of tandem CUB (a1a2), tandem coagulation factor V/VIII (b1b2), and one MAM (c1) domain. Cartoon representation of the seven crystal structures presented in this report with the resolution limits listed below. Orange spheres indicate a bound calcium ion in the a2 domain. B) Sequence alignment of the a1a2b1b2 domains of human Nrp1 and Nrp2. Secondary structure elements refer to the Nrp2-a1a2b1b2 structure (blue, a1; green, a2; yellow, b1; red, b2) and are named according to conventions adopted for the spermadhesin CUB domain (Romero, A. et al., Nat Struct Biol 4, 783-8 (1997)) and the coagulation factor V C2 domainMacedo-Ribeiro, S. et al., Nature 402, 434-9 (1999)). Residues boxed in blue and yellow delineate the antibody epitopes for anti-panNrp[4] and anti-Nrp1[B], respectively. Amino acids highlighted in orange indicate the $Ca^{2+}$ binding site in a2, while residues in red represent a putative $Ca^{2+}$ binding site in the a1 domain. Residues shaded in green highlight the positions of amino acid substitutions that disrupt interactions between Sema3A and Nrp1 (Gu, C. et al., J Biol Chem 277, 18069-76 (2002)). This alignment was produced with EsPript (Gouet, P. et al., Nuclei Acids Res 31, 3320-3 (2003)).
FIG. 2C—Data Collection and Refinement Statistics
Figure 2B:
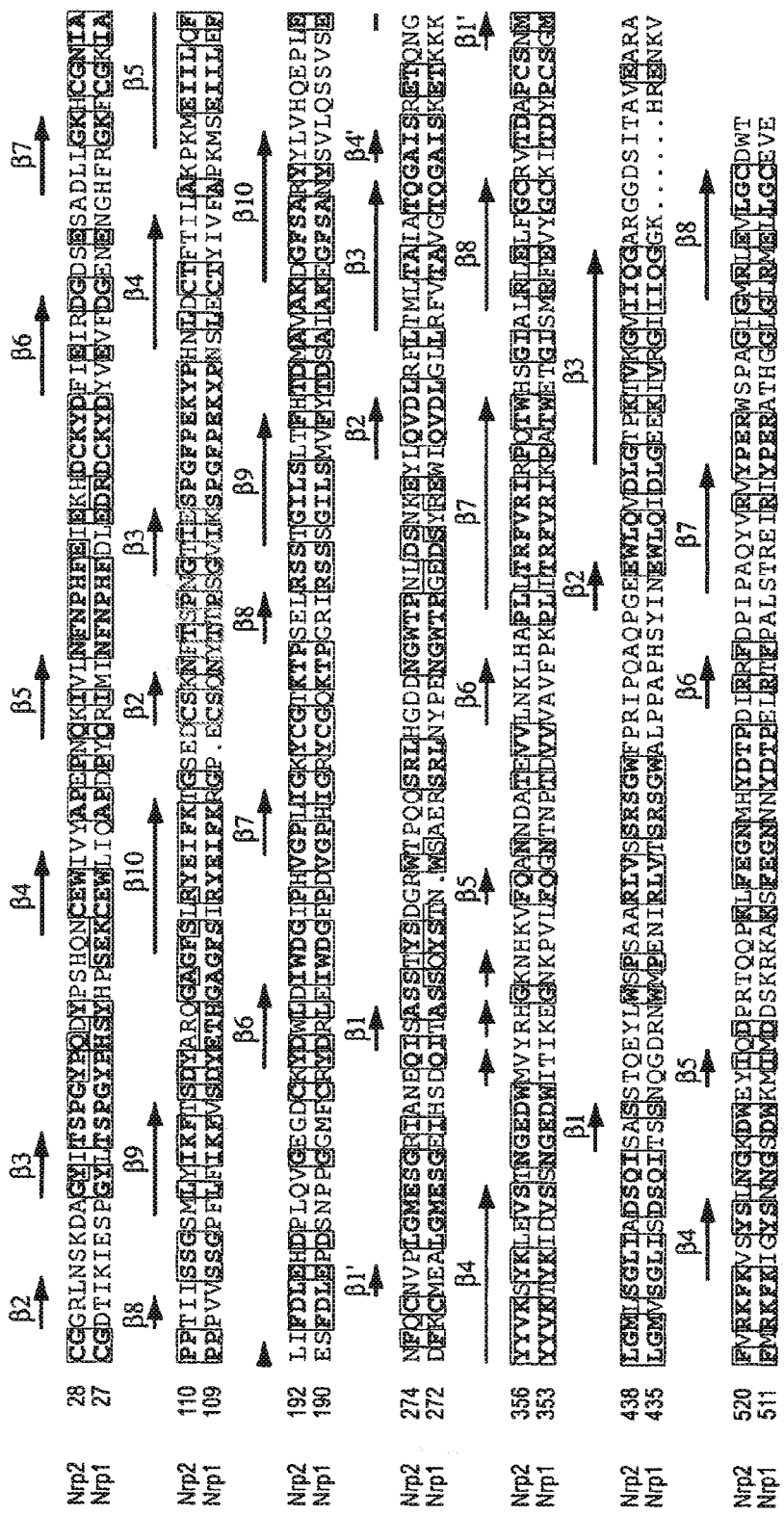
Figure 3A:
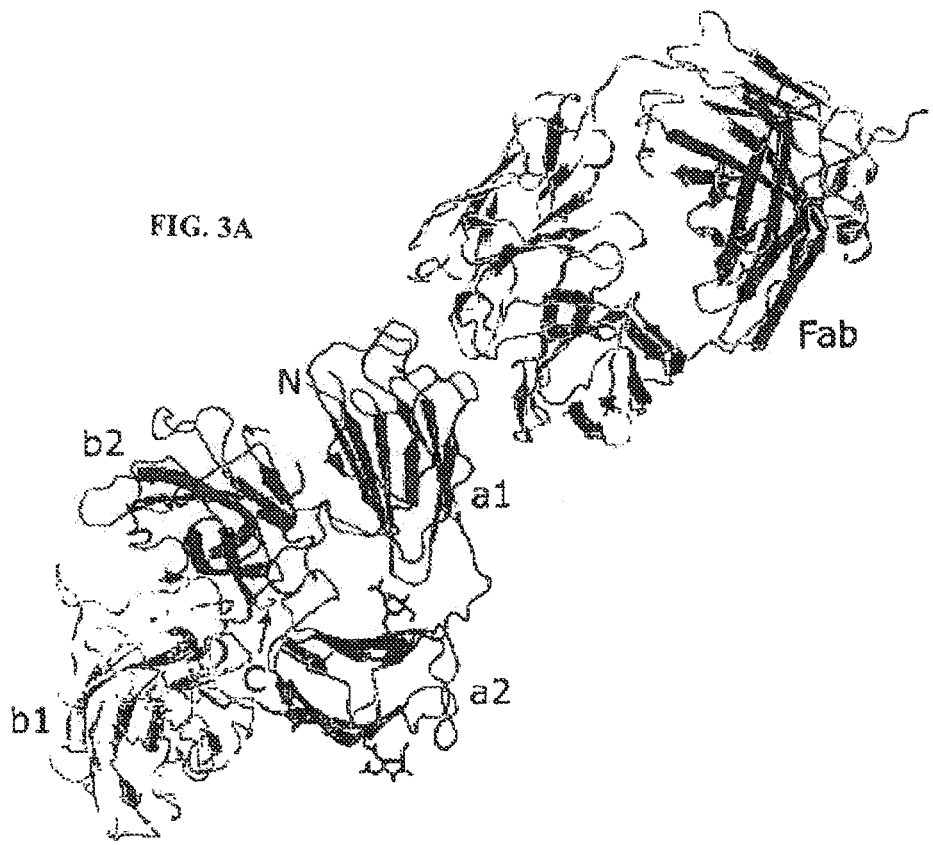
FIG. 3—Overall Domain Architecture of Neuropilins A) Domain organization of Nrp2 (blue, a1; green, a2; yellow, b1; red, b2) in complex with the Fab fragment of anti-panNrp[4] (light orange, heavy chain; grey, light chain). N-glycosylated residues are indicated in magenta. B) Ribbon representation of the Nrp1 and Nrp2 a2b1b2 structures; the orange spheres highlight a bound calcium ion. C) Superposition of the Nrp2/Fab complex from two different crystal forms based on the a2b1b2 domains. Note the poor superposition of the a1 domains in comparison to the a2b1b2 region. All structure figures were produced with PyMol (http://www.pymol.org).
Figure 3B:
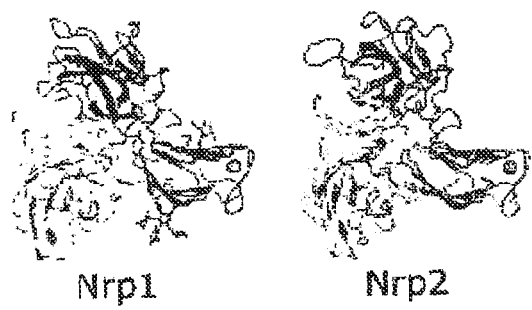

Two different strategies were used to produce protein for structural studies. The smaller neuropilin fragments that only include the type b domains were expressed in *E. coli* while the larger Nrp constructs required production as secreted proteins from baculovirus-infected insect cells. An overview of the seven structures is presented in FIG. 2. Briefly, crystals of the VEGF binding portion (b1b2) of Nrp1 and Nrp2 diffracted to a maximum resolution of 1.8 and 1.95 Å, respectively. Crystals of the a2b1b2 domains of Nrp1 and Nrp2 were refined to 2.0 and 2.3 Å resolution, respectively and the b1 domain of Nrp1 in complex with the VEGF-blocking Fab, anti-Nrp1$^B$, diffracted to 2.2 Å resolution. Finally, the crystal structure of the Nrp2 a1a2b1b2 domains was solved in complex with the semaphorin-blocking Fab, anti-panNrp$^A$; two crystal forms of this complex were identified that diffracted to 2.75 and 3.1 Å. All structures were solved by molecular replacement and are reported with final $R_{work}/R_{free}$ values below 20/25% with good stereochemistry (FIG. 2C). The Nrp1 a2b1b2 structures have two N-linked glycosylation sites on opposite sides of the a2 domain (FIG. 3B). The monoclinic form of the Nrp2/Fab complex also shows two glycosylation sites within the a2 domain (FIG. 3A); however, these sugars moieties are not well defined in the electron density of the Nrp2-a2b1b2 structure and therefore are not modeled (FIG. 3B).

The Overall Domain Architecture of the Neurophilin Ectodomain

The neuropilin extracellular region is often divided into three units that describe the primary semaphorin-binding (a1a2), VEGF-binding (b1b2), and dimerization domains (c), respectively (Ellis, L. M., *Mol Cancer Ther* 5, 1099-107 (2006)). Indeed, the recent crystal structure of rat Nrp1 b1b2 (Vander Kooi, C. W., et al., *Proc Natl Acad Sci USA* 104, 6152-6157 (2007)), identified a large interface between the b1 and b2 domains and as the residues buried between domains are conserved in sequence, this b1b2 domain arrangement was recognized as a general feature of the Nrp family. Here, four crystal structures of Nrp that include the a2, b1, and b2 domains have been solved (FIG. 2,3) from a variety of crystallization conditions (FIG. 10). Two models include the a1 domains bound to Fab fragments while two others include calcium ions in the a2 domains. Despite these differences, the three domains (a2, b1, and, b2) share the same arrangement in all crystal structures and pack tightly around a pseudo 3-fold axis (FIG. 3). The Nrp1 and Nrp2 a2b1b2 structures are very similar and superimpose with an r.m.s.d. (root mean square deviation) of 1.2 Å over 317 Cα atoms. The interface between b1 and b2 is conserved between both neuropilins, burying about 1200-1500 Å$^2$ of solvent accessible surface. Interestingly, the interface between the a2 domain and the b1b2 is conserved in all structures as well and buries more than 2000 Å$^2$ of solvent accessible surface, indicating that all three domains form a rigid structural unit (FIG. 3).

Figure 3C:
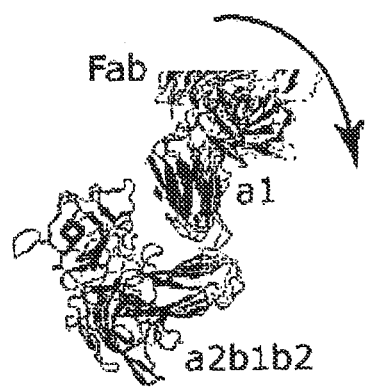

In contrast, the domain arrangement between a1 and a2b1b2 is not preserved between the two crystal forms of the Nrp2/anti-panNrp$^A$-Fab complex. When superimposing the a2b1b2 cores of the receptors, the a1 domains are displaced by about 7 Å with respect to each other. The interface between a1 and a2b1b2 is small (~800 Å$^2$ buried surface area) and not conserved. The lack of strong interactions identifies flexibility of the a1 domain, suggesting that it can undergo conformational changes in respect to the remainder of Nrp in solution or upon receptor binding (FIG. 3C).

Nrp CUB Domains Include Calcium- and Semaphorin-Binding Sites

The a1 and a2 domains of Nrp1 and Nrp2 are CUB domains (Ellis, L. M, *Mol Cencer Ther* 5, 1099-107 (2006)). In the CUB domain prototype, spermadhesin (Romero, A., et al., *Nat Struct Biol* 4, 783-8 (1997), the fold comprises two 5-stranded β-sheets that form a β-sandwich. Strands β2, β4, β9, β6 and β7 form one β-sheet with the other sheet containing strands β1, β3, β10, β5 and β8; however, strands β1 and β2 are frequently absent in CUB domains from several complement family proteins (Feinberg, H. et al., *EMBO J* 22, 2348-59 (2003); Gregory, L. A. et al., *J Biol Chem* 278, 32157-64 (2003); Gregory, L. A. et al., *J Bol Chem* 279, 29391-7 (2004)). Similar to these proteins, the a1 and a2 domains of Nrps lack the β1 strand (FIG. 4). Overall, CUB domains display a high degree of similarity. For example, the Nrp a2 domain is structurally similar to the Nrp1 a2 domain (r.m.s.d. of 0.9 Å), the Nrp2 a1 domain (r.m.s.d. of 0.9 Å), and the CUB domain from spermadhesin (Romero, A. et al., supra) (r.m.s.d. of 1.4 Å).

Figure 4A:
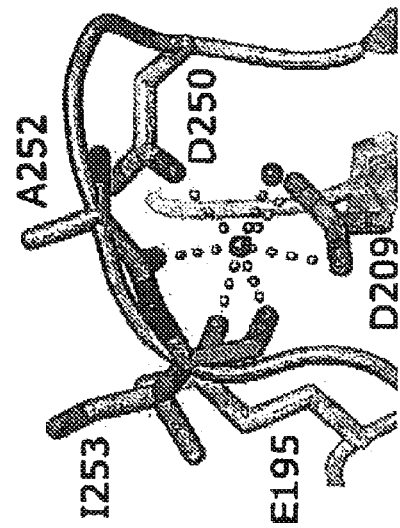
FIG. 4—Molecular Details of the Neuropilin CUB Domains. A) In the a2b1b2 structures, the a2 domain includes a bound calcium ion (orange). The Nrp a1 (see panel C) and a2 domains lack the b1 strand found in spermadhesin (Romero et al, supra). B) The calcium ion of the Nrp1 a2 domain is co-ordinated by three negatively-charged amino acids, two main-chain carbonyl oxygens, and a water molecule. These interactions are highly conserved among Nrps (See FIG. 12, 13). C) (left panel) Amino acids are colored according to the percentage of solvent-accessible surface that is buried at the Nrp2/Fab interface (red, 75-100%; orange, 50-74%; yellow, 25-49%). Anti-panNrp[4] is cross-reactive for Nrp1 and Nrp2, and eleven of the fourteen residues in the structural epitope are identical (black text, identical; white text, non-conserved; asterisks indicate residues in which the side chain points toward the a1 protein core). Residues outlined in green represent the positions of amino acid substitution that are necessary for interactions between Nrp1 and Sema3A[23]. (right panel) The Cα atoms of these amino acid substitutions are indicated as green spheres. Cα atoms shaded in purple represent a putative calcium-binding site. D) The anti-panNrp[4]/Nrp2 interface. Nrp2 is shown as a molecular surface according to the electrostatic potential (red, acidic; blue, basic). The antibody contact residues are dominated by aromatic resides from CDRs H2, H3, and L3.
Figure 4B:
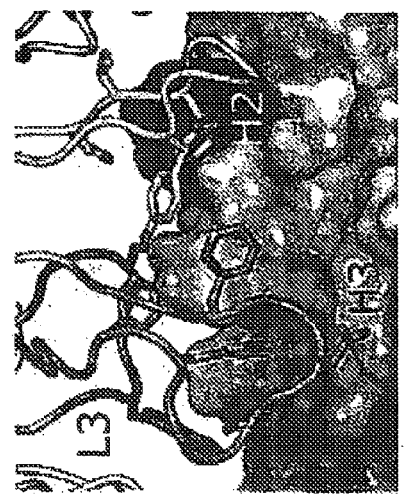
Figure 12A:
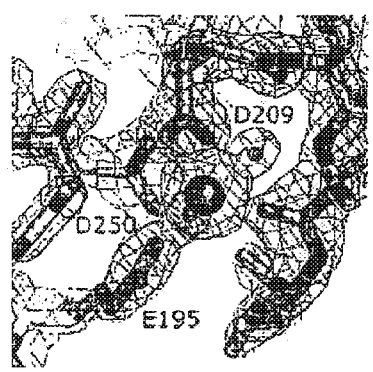
FIG. 12—Nrp CUB domains include a conserved calcium-binding site. A) Electron density around the calcium ion in the Nrp1 a2b1b2 structure (final $2F_o$-$F_c$ map contoured at 1.5σ. B) The calcium ion of the Nrp2 a2 domain C) Three negatively-charged amino acids (shaded in orange), which delineate the calcium-binding site, are conserved in the CUB domains from Nrp1 and Nrp2.
Figure 12B:
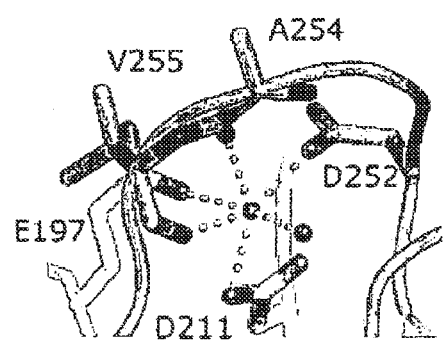
Figure 12C:
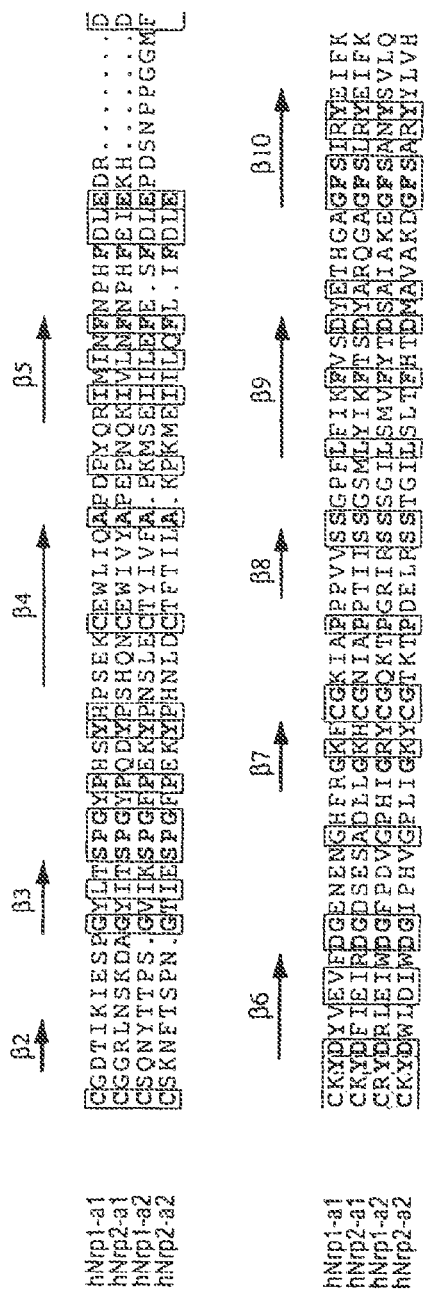
Figure 13A:
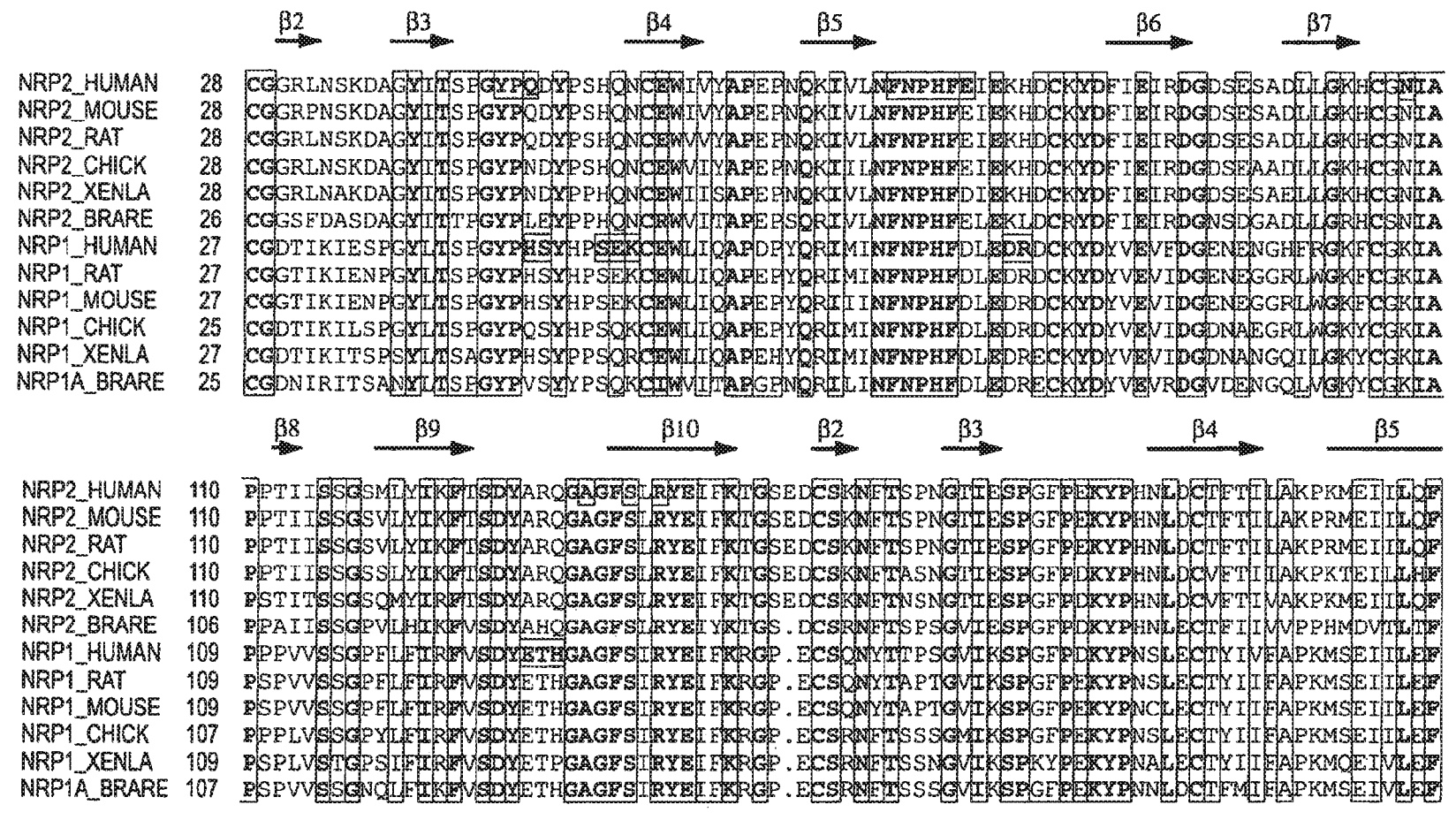
Figure 13B:
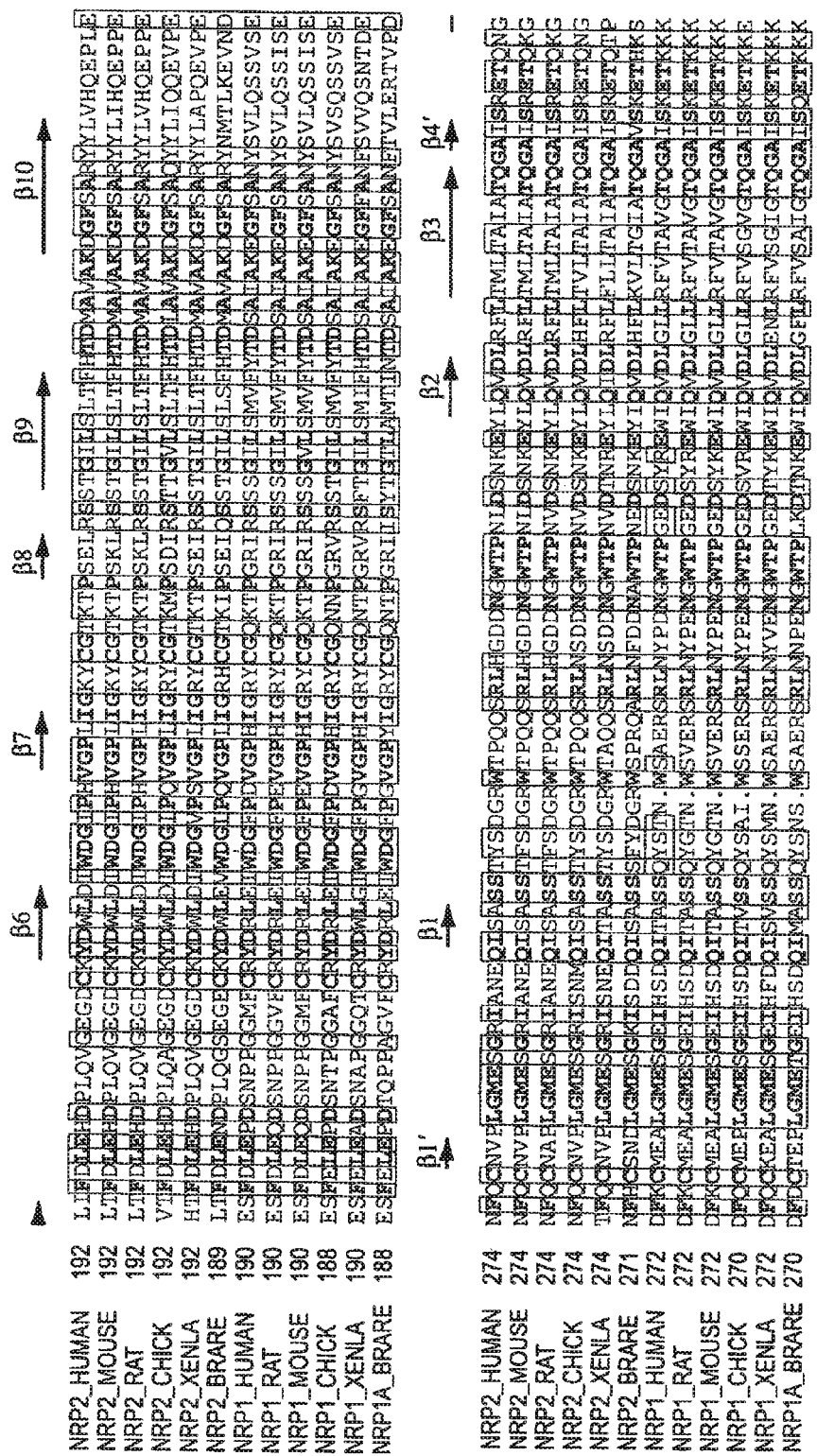
FIG. 13—Sequence Alignment of the Neuropilins. Full-length sequence alignment of the a1a2b1b2 domains from human, mouse, rat, zebrafish (BRARE), frog (XENLA), and chicken Nrp1 and Nrp2. This figure is colored using the same scheme as FIG. 2B and was produced with EsPript (Gouet P. et al., supra).
Figure 13C:
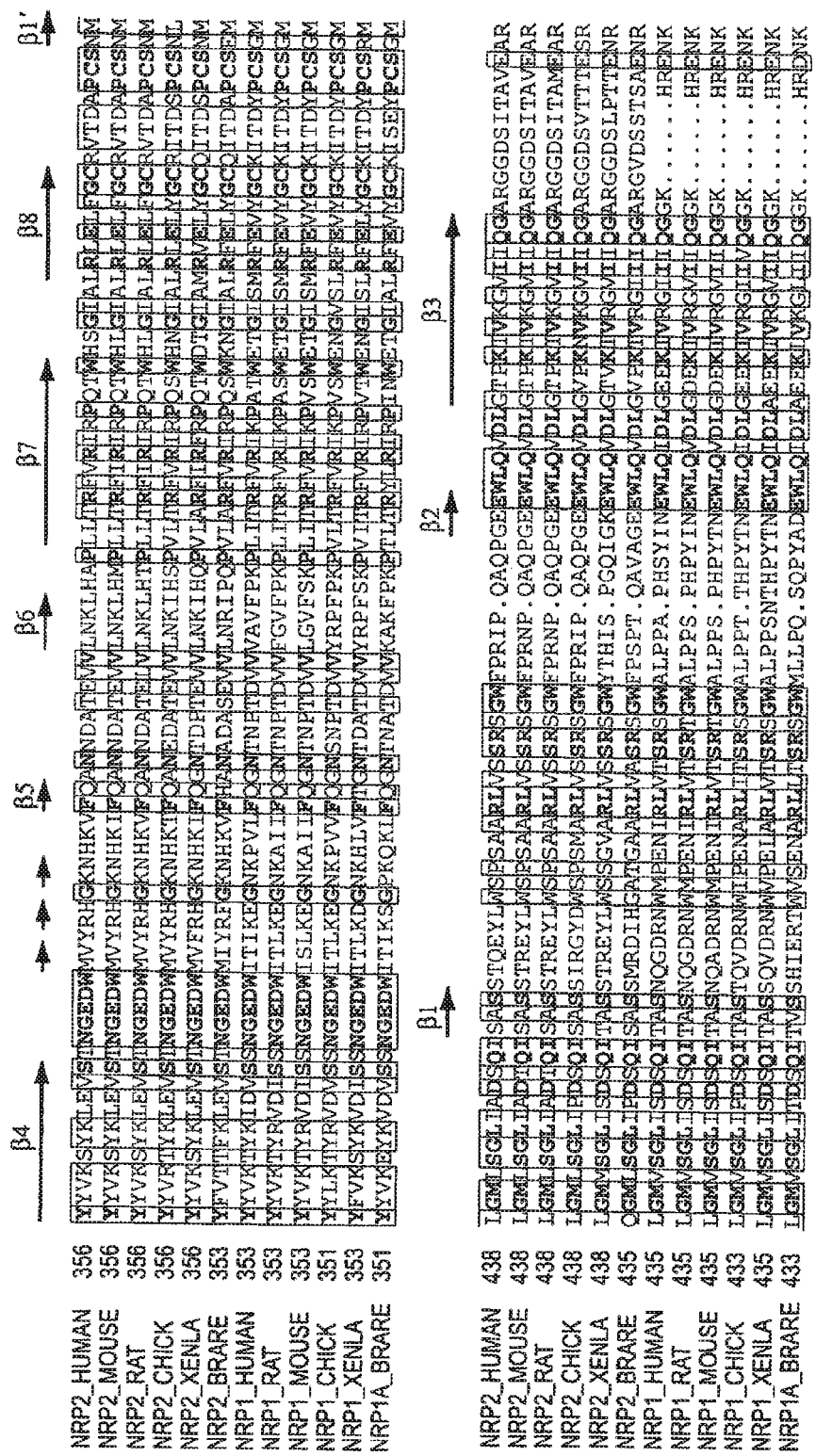
Figure 13D:
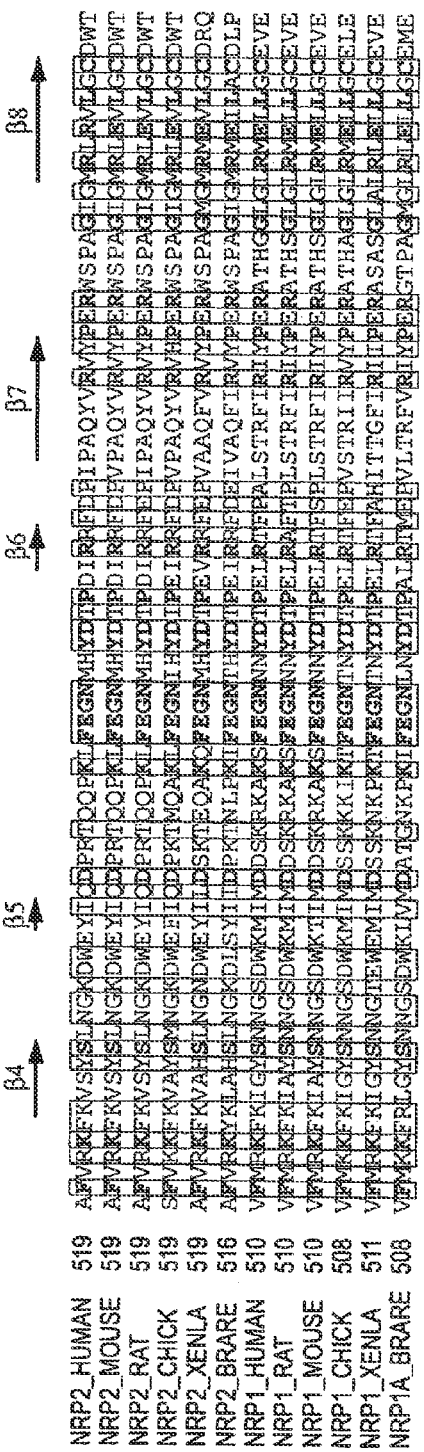

The crystal structures of CUB domains from the complement family proteins C1s and MASP-2[36,37] contain a calcium-binding site at one end of the sandwich. The Nrp1 and Nrp2 a2b1b2 structures also contain a bound ion at this location within domain a2 (FIG. 3B,4A). In the Nrp1 structure, the ion is clearly observed in the electron density (FIG. 12) even though no divalent cations were included during crystallization (FIG. 10). In Nrp1, the calcium ion is co-ordinated by three negatively-charged side chains (Glu$^{195}$, Asp$^{209}$, and Asp$^{250}$), two carbonyl oxygens (Ala$^{252}$ and Ile$^{253}$), and a water molecule (FIG. 4B). Similarly, the calcium co-ordination involves three negatively-charged amino acids in Nrp2 (Glu$^{197}$, Asp$^{211}$, and Asp$^{252}$; see FIG. 12); these three residues are absolutely conserved in the a2 domains from twelve distantly related species (FIG. 13)

A sequence alignment among the a1 and a2 domains of Nrps (FIG. 12) shows that this triad of charged residues is also strictly conserved within the a1 domain of the Nrps. However, in the Nrp2/anti-Nrp$^A$-Fab complex, there is no indication of a bound ion in the a1 domain. The loops contributing the residues that define the putative a1 Ca$^{2+}$ binding site are poorly ordered, suggesting that Ca$^{2+}$ plays a role in stabilizing the fold of the domain. Based on the high degree of sequence conservation, it is likely that calcium binding represents a shared feature of Nrp CUB domains.

Neuropilins function as co-receptors for select members of the class 3 family of semaphorins. The N-terminus contains the signature "Sema" domain, a 7-bladed β-propeller (Antipenko, A., et al., *Neuron* 39, 589-98 (2003)) which is required for binding the a1a2 domains of neuropilins. Anti-panNrp$^A$ blocks binding of Sema3 to both Nrp1 and Nrp2 (FIG. 1), but does not affect VEGF binding (data not shown). In the structure of the Nrp2/anti-panNrp$^A$-Fab complex (FIG. 4C), the Fab fragment contacts only the a1 domain of Nrp2 on the β8-5-10-3 face of the sandwich burying approximately 1400

Figure 4C:
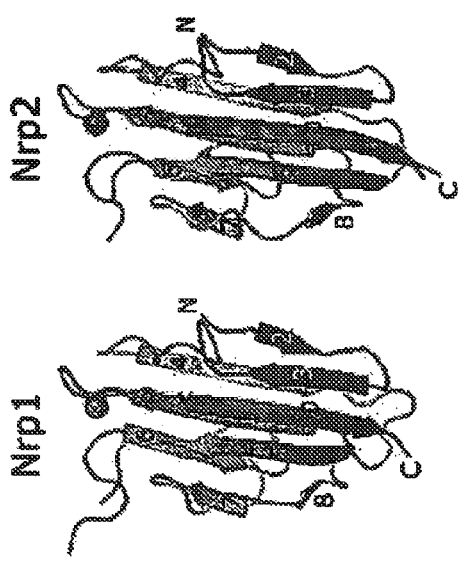

Å² of solvent accessible surface. The interface recognized by this antibody is well conserved between Nrp1 and Nrp2 as 11 of the 14 Nrp2 residues that have more than 25% of their accessible surface buried in the interface are identical between the two receptors (FIG. 4C). The recognition of an epitope that is conserved between Nrp1 and Nrp2 explains the ability of the antibody to bind both receptors with affinities in the sub-nanomolar range (FIG. 11).

Figure 4D:
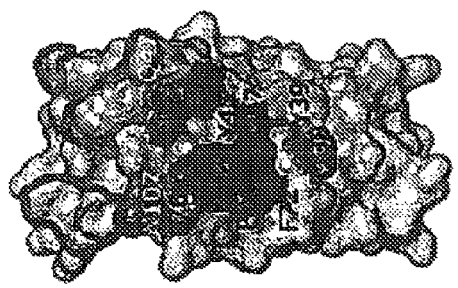

On the antibody side, 11 side chains contact Nrp2 from CDRs L3, H2 and H3, 7 of which are aromatic in character (FIG. 4D). Previous studies outlined the semaphorin binding site of Nrp1 using site directed mutagenesis (Gu, C. et al., *J Biol Chem* 277, 18069-76 (2002). Based on a model of spermadhesin, putatively solvent exposed residues on the surface of the a1 domain were selected for amino acid substitutions. Using this approach, a number of mutants were identified that disrupt the interactions between Sema3A and Nrp1 (Gu et al., supra) and when mapped onto a model of Npr1 a1, they are located on the loops at one pole of the a1 β-sandwich (FIG. 4C). Substitutions at the other end of the domain had no affect on Sema3A binding (Gu et al., supra). The mutations disrupting Sema3A binding are adjacent to the epitope recognized by the Sema3A-blocking Fab (FIG. 4C), strongly suggesting that the sema domain binds the loops and the 8-5-10-3 face of the sandwich within the Nrp2 a1 domain. The location of the semaphorin-binding site is also adjacent to the putative calcium-binding site of the a1 domain (FIG. 4C), suggesting that calcium binding may play a role in the interactions between the ligand and receptor.

Nrp Type B Domains Contain the Heparin- and VEGF-Binding Sites

The b domains from the human neuropilin b1b2 structures (FIG. 5A and Vander Koo et al., supra, Lee et al., supra) share significant homology with the phospholipid-binding (type C2) modules from coagulation factors V and VIII (F5/8) (Macedo-Ribeiro et al., *Nature* 402, 434-9 (1999); Pratt, K. P., et al., *Nature* 402, 439-42 (1999)) and to the galactose-binding domain of bacterial sialidase (Gaskell, A. et al., *Structure* 3, 1197-205 (1995)). Collectively, these domains define the discoidin fold that is topologically classified as a distorted jelly-roll β-barrel composed of eight core β-strands. One pole of the domain contains three extended "spikes" or loops that typically constitute the ligand-binding site for discoidin family members (Macedo-Ribeiro et al., supra; Pratt et al., supra; Gaskell et al., supra. The b1b2 fragment of Nrp1 and Nrp2 share 50% sequence identity and superimpose with an r.m.s.d. of 2.3 Å over 307 Cα atoms (FIG. 5A). While the b1 domains of Nrp1 and Nrp2 are nearly indistinguishable (r.m.s.d.=0.6 Å), the b2 domains superimpose less well (r.m.s.d.=2.7 Å) with the differences largely stemming from different conformations of the "spikes" (FIG. 5A). As these spikes frequently define binding sites within the discoidin family (Vander Kooi et al., supra; Lee et al., supra; Macedo-Ribeiro et al., supra; Pratt et al., supra; Gaskell et al., supra, the dissimilarity between Nrp1 and Nrp2 may represent one way for Nrps to recognize distinct binding partners.

Despite the differences between the b2 domains of the Nrp1 and Nrp2, the b domains are tightly packed and form a rigid scaffold (FIG. 5). The interdomain junction form a deep cleft that runs roughly perpendicular to the long axis of the two b domains (FIG. 5). This cleft, created by the β4:β5 loop of b1 and the β5:β6 loop of b2, is surrounded by a number of positively charged residues, which based on mutagenesis experiments on rat Nrp1 (Vander Koo et al., supra, represents the heparin-binding site of Nrps. The electropositive patch is present in the structure of both human Nrps as well (FIG. 5B). The C-terminal domain of $VEGF_{165}$ (also known as $VEGF_{55}$) (Fairbrother et al., *Structure* 6, 637-48 (1998)) also contains a heparin binding site. As heparin increases the affinity of b1b2 for $VEGF_{165}$ up to 100-fold (Mamluk, R. et al., *J Biol Chem* 277, 24818-25 (2002); Fuh, G. et al., *J Biol Chem* 275, 26690-5 (2000)), it is feasible that Nrps use heparin to recruit $VEGF_{165}$ to this region.

Figure 14A:
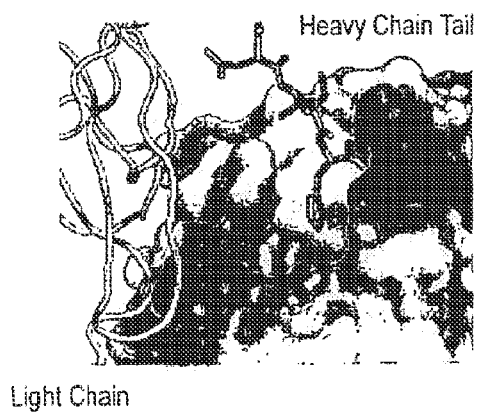
FIG. 14—Comparison between the Nrp1/Tufstin and the b1/Fab Structures A) In the nrp1-b1/anti-Nrp1$^B$-Fab complex, the C-terminal tail (purple) of the heavy chain from a symmetry-related molecule occupies the Tuftsin-binding site (Nrp2, molecular surface by electrostatic potential; orange, antibody heavy chain; grey, antibody light chain). B) Location of Tuftsin (green) in complex with rat Nrp1 b1b2 (PDB accession no. 2ORZ) (Vander Kooi, et al., supra). C) Superposition of the two structure highlighted in panel A. The antibody and Tuftsin peptide are colored as in the previous panels with human Nrp1 b1 colored in yellow and rat Nrp1 b1b2 colored in cyan.
Figure 14B:
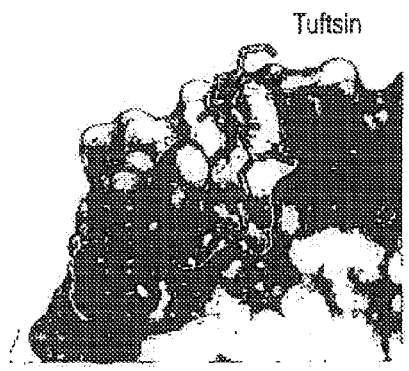
Figure 14C:

In addition to this heparin mediated interaction between exon 7 of $VEGF_{165}$, the C-terminal tail of VEGF (CDK-$PRR_{COOH}$) encoded by exon 8 can bind directly to Nrps. In the crystal structure of rat Nrp1-b1b2 in complex with Tuftsin (Vander Kooi et al., supra), a tetrapeptide mimetic (TK-$PR_{COOH}$) of the VEGF tail (von Wronski, M. A. et al., *J Biol Chem* 281, 5702-10 (2006)), the C-terminal arginine is tucked tightly into an acidic groove created by residues from the conserved "spikes" of the b1 domain. In several of our structures, including all three Fab complexes, the C-terminal residue (a histidine) from a symmetry-related molecule occupies the same acidic pocket of the Tuftsin peptide (FIG. 14).

To further detail potential residues involved in VEGF binding, the surface conservation of Nrp residues on the b1b2 surface was examined (FIG. 5C). Two contiguous patches are conserved among twelve Nrp1 and Nrp2 proteins (FIG. 13). One of these sites maps directly to the Tuftsin-binding site, while the second site includes residues on the edge of the heparin-binding patch, suggesting an additional area for interactions between Nrp and VEGF.

In the crystal structure the Nrp1-b1/anti-Nrp1$^B$-Fab complex (FIG. 5D), the Fab contacts an epitope located between these two putative VEGF binding sites and partially overlaps with the Tuftsin binding cleft. The epitope of this VEGF blocking antibody is unusual, involving only residues from CDRs L1 and H3. On average, Fab/antigen interfaces bury 1680 Å² of solvent exposed surface (Lo Conte et al., *J Mol Biol* 285, 2177-98 (1999)), however only 900 Å² are shielded at the Nrp1-b1/Fab interface. Despite the small interface, anti-Nrp1$^B$ binds tightly to Nrp1 with an affinity of 0.2 nM (Liang et al., supra; Pan et al., supra).

VEGF and Sema3A do not Compete for Nrp Binding

Figure 15A:
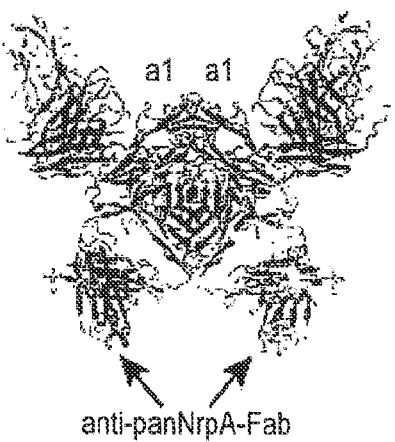
FIG. 15—The Nrp2 Dimer Interface A) Ribbon representation of the Nrp2-a1a2b1b2/Fab dimer as seen in the monoclinic form of the structure. B) Superposition of the Nrp1-b1/anti-Nrp1$^B$-Fab structure onto the Nrp2/Fab crystal structure. C) Amino acids buried at the a1/a1 interface are colored according to the percentage of solvent accessible surface that is buried upon dimerization (red, 75-100%; orange, 50-74%; yellow, 25-49%).
Figure 15B:
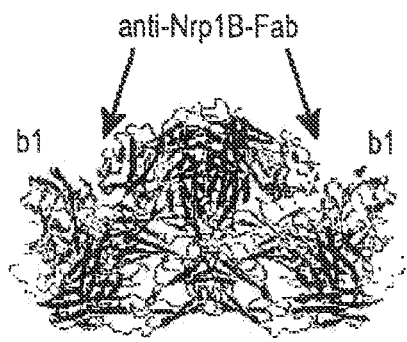
Figure 15C:
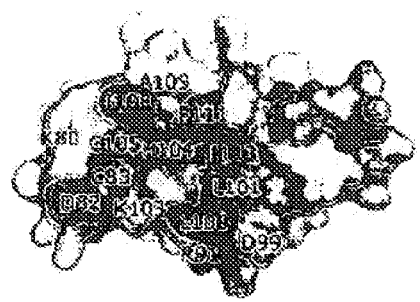

In the Nrp/Fab crystal structures of the present invention, the binding epitopes blocking VEGF and Semaphorin binding are separated by 65 Å and located on opposite sites of the Nrp (FIG. 15). Several studies have reported that VEGFs and semaphorins compete for binding on the cell surface and that this competition involves a partially overlapping binding site on the b1 domain (Gu et al., supra; Miao, H. Q. et al., *J Cell Biol* 146, 2177-98 (1999); Narazaki, M. & Tosato, G., *Blood* 107, 3892-901 (2006)). As the carboxyl tail of $VEGF_{165}$ and class 3 semaphorins are both rich in basic residues, it was suggested that these tails might compete for the electronegative groove created by the "spikes" in the b1 domain (Vander Kooi et al., supra; Lee et al., supra). The recent b1b2/Tuftsin crystal structure identified that the $VEGF_{165}$ tail likely occupies this binding site. We have previously shown that anti-NRP1$^B$ does not antagonize Sema3A-mediated collapse of axons from dorsal root ganglia (DRG) (Liang et al., supra; Pan et al., supra) suggesting that the C-terminal tails of Sema3 do not bind the same groove.

Previous competition experiments (Gu et al., supra; Miao et al., supra; Narazaki et al., supra) employed VEGFs and semaphorins that contained that contained heterologous tag (such as alkaline phosphatase) at the C-terminus of the protein. It is possible that the observed competition is a result of steric clashes from the tags rather than direct competition between the VEGF and Sema3 tail. We examined the ability of $VEGF_{165}$ to antagonize Sema3-mediated collapse of axonal growth from DRG. Even at concentrations of 100 mM, $VEGF_{165}$ did not affect the ability of Sema3A to cause the retraction of actin processes (FIG. 1). These data demonstrate that Sema3 does not compete with VEGF for binding to the b1 domain and that the tail of semaphorins contacts a different site within this domain.

Models for Neuropilin Dimerization

Figure 6A:
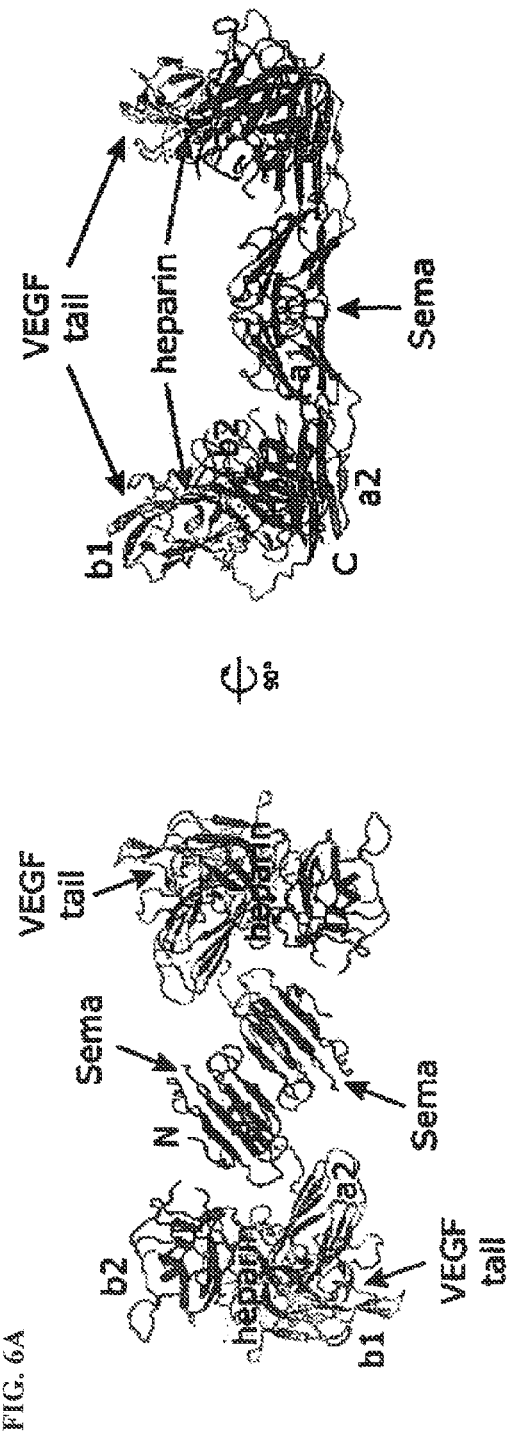
FIG. 6—A Nrp2 Crystallographic Dimer Suggests Models for VEGF and Semaphorin binding A) Nrp2 forms a saddle-shaped dimer in both crystal forms of the Nrp2/Fab complex. This figure highlights the Nrp2 a1a2b1b2 domains from the monoclinic form of the Fab complex. The putative VEGF tail-, heparin-, and semaphorin-binding sites are indicated. B) Potential models of VEGF/Nrp and semaphorin/Nrp complexes based upon the Nrp a1-mediated dimer in the crystal structures.
Figure 6B:
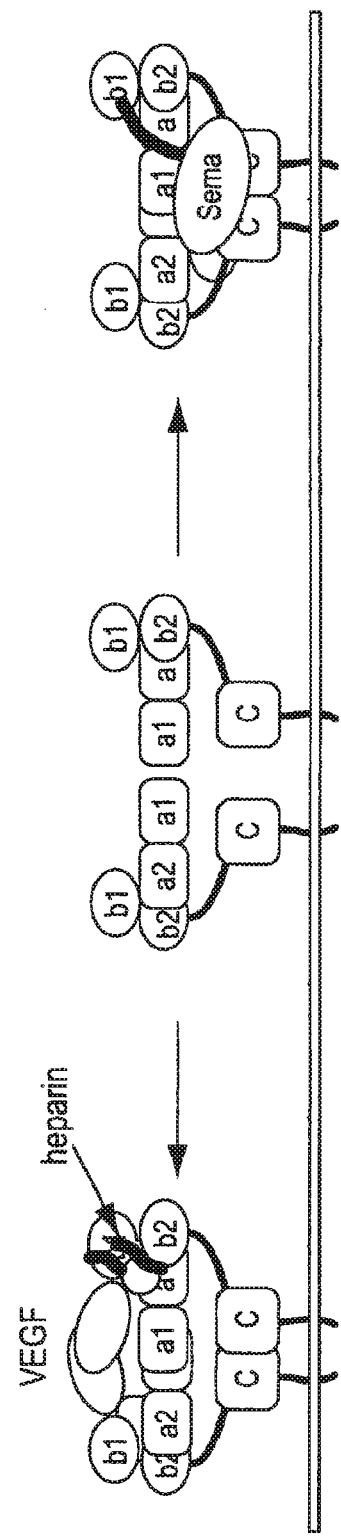

Nrp1 and Nrp2 can form homo- or hetero-multimers even in the absence of ligand (Takahashi, L. et al., *Cell* 99, 59-69 (1999); Chen, H. et al., *Neuron* 21, 1283-90 (1998); Giger, R. J. et al., *Neuron* 21, 1079-92 (1998); Takahashi et al., *Nat Neurosci* 1, 487-93 (1998))) and although the exact stoichiometry of neuropilin complexes has not yet been established, it is widely presumed that Nrps form homodimers upon ligand binding. Current data shows that the c domain is necessary but not sufficient for Nrp oligomerization since truncation mutants lacking this domain display reduced mutimerization relative to the full-length ECD (Takahashi et al., *Cell* 99, 59-69 (1999); Chen et al., supra; Giger et al., supra; Nakamura et al., *Neuron* 21, 1093-100 (1998)). Neuropilin constructs that include the a1a2 and b1b2 domains have higher affinity for some VEGF isoforms than constructs that span only the b1b2 domains (Mamluk, R. et al., *J. Biol. Chem.* 277, 24818-25 (2002); Karpanen, T. et al., *FASEB J* 20, 1462-72 (2006); Giger, R. J. et al., *Neuron* 25, 29-41 (2000) even though the a1a2 domains do not bind VEGF. It is therefore feasible that the a1a2 domains contribute directly to Nrp dimerization and thus strengthen interactions between Nrp and the VEGF dimer by stabilizing the 2:2 complex. Interestingly, the crystal structures of Nrp2-a1a2b1b2 from two different crystal forms (FIG. 2C) contain a conserved, crystallographic interface that is mediated by a1. In this dimer, the a1 domains align in a roughly anti-parallel arrangement along β7 and β8 strands. The interface buries approximately 1200 Å$^2$ of solvent accessible surface area and is dominated by hydrophobic interactions (FIG. 15). Interestingly, similar dimers have been observed for other CUB domain family members (Romero et al., supra). However, examination of the molecular masses of three Nrp2 constructs (a2b1b2, a1a2b1b2, and a1a2b1b2c) by multi-angle light scattering revealed that all three Nrp2 constructs are monomeric in solution (data not shown). These data imply that the homodimerization of Nrps is very weak in solution, even in the presence of the MAM domain, and that receptor dimerization may only occur upon ligand binding. The orientation of crystallographic Nrp2 dimer suggests a model for VEGF binding. The a1 interface creates a saddle-shaped dimer with a width of approximately 70 Å (FIG. 6), large enough to accommodate a VEGF$_{109}$-dimer with dimensions of about 35×60 Å. Importantly, the Tuftsin binding sites and the heparin binding patches are found on the inner surface of the saddle. Heparin could stabilize interactions between the heparin binding sites of Nrp and VEGF and further facilitate the association of the VEGF tail with the "spikes" of b1. This arrangement would also be able to accommodate VEGFR binding via the VEGF receptor-binding domain for downstream signaling. Therefore, although the a1 domains do not directly engage VEGF, they could enhance VEGF binding of Nrps as they facilitate Nrp dimerization. This dimer could further accommodate Sema3 binding (FIG. 6). In the Sema3A crystal structure (Antipenko, A. et al., *Neuron* 39, 589-98 (2003)), two "sema" domains pack tightly together at an interface. Upon Nrp binding, the sema domains of Sema3A dissociate to allow interactions with the primary binding site on a1a2 (Antipenko, et al., supra). In the model of the a1-mediated Nrp dimer presented here, the two putative Sema3A binding sites are located on opposite sides, and distant enough to accommodate the large β-propellers of two bound Sema3 molecules (FIGS. 6 and 15).

The present structural analysis provides the first detailed picture of both, the VEGF (b1b2) and semaphorin-binding (a1a2) portions of the Nrp ECD. The antibody complexes (FIGS. 3-5) along with previous mutagenesis studies (Gu et al., supra; Vander Kooi et al., supra) delineate the Nrp binding sites for the Sema domain of Semaphorins, and the Heparin binding domain of VEGF. These structures provide a basis for future mutagenesis experiments and provide strategies to elucidate the structures of Nrps in complex with their ligands and signaling receptors VEGF, VEGFR, semaphorins, and plexins. In addition, the crystal structures and other information provided by the present invention enable the design of VEGF and/or semaphorin antagonists and agonists, and can be used in screening assay to identify such antagonists or agonists.

Although in the foregoing description the invention is illustrated with reference to certain embodiments, it is not so limited. Indeed, various modifications of the invention in addition to those shown and described herein will become apparent to those skilled in the art from the foregoing description and fall within the scope of the appended claims.

All references cited throughout the specification, and the references cited therein, are hereby expressly incorporated by reference in their entirety.

TABLE 1

|  | Nrp1$_{b1b2}$ | Nrp1$_{a2b1b2}$ | Nrp1$_{b1}$/Fab | Nrp2$_{b1b2}$ | Nrp2$_{a2b1b2}$ | Nrp2$_{a1a2b1b2}$/Fab | Nrp2$_{a1a2b1b2}$/Fab |
|---|---|---|---|---|---|---|---|
| Data collection | | | | | | | |
| Space group | P2$_1$2$_1$2$_1$ | P2$_1$ | H3 | P2$_1$2$_1$2$_1$ | P2$_1$ | C2 | P3$_2$21 |
| Cell domensions | | | | | | | |
| a, b, c, (Å) | 65.9, 66.7, 74.7 | 53.2, 68.2, 66.6 | 213, 213, 45.3 | 36.5, 70.5, 122 | 50.1, 193, 66.2 | 148, 106, 92.4 | 121, 121, 203 |
| αβγ (°) | 90, 90, 90 | 90, 102, 90 | 90, 90, 120 | 90, 90, 90 | 90, 90.1, 90 | 90, 98.8, 90 | 90, 90, 120 |
| Wavelength (Å) | 0.979 | 0.979 | 0.979 | 1.00 | 1.00 | 1.00 | 1.00 |
| Resolution (Å) | 50-1.8 | 50-2.0 | 50-2.2 | 50-1.95 | 50-2.3 | 50-2.75 | 50-3.1 |
| Rmerge | 5.0 (51.5) | 8.6 (32.2) | 9.6 (48.5) | 8.9 (53.0) | 5.6 (34.4) | 10.4 (52.7) | 6.1 (51.5) |
| I/σI | 26.9 (3.2) | 13.8 (2.4) | 14.3 (2.2) | 16.8 (3.1) | 20.7 (3.7) | 10.9 (3.3) | 18.3 (2.6) |
| Completeness (%) | 97.6 (99.3) | 97.5 (88.7) | 99.0 (98.0) | 99.8 (99.9) | 94.5 (85.6) | 99.6 (100) | 99.6 (98.9) |
| Redindancy | 4.6 (4.6) | 3.5 (3.0) | 4.4 (3.6) | 5.3 (5.2) | 4.2 (4.1) | 4.2 (4.2) | 3.8 (3.6) |
| Refinement | | | | | | | |
| Resolution (Å) | 20-1.8 | 20-2.0 | 20-2.2 | 20-1.95 | 20-2.3 | 20-2.75 | 20-3.1 |
| No. Reflections | 29,017 | 29,213 | 37,085 | 22,404 | 49,667 | 34,437 | 30,187 |
| Rwork/Rfree | 0.160/0.1.999 | 0.186/0.245 | 0.163/0.208 | 0.175/0.233 | 0.193/0.236 | 0.194/0.245 | 0.202/0.241 |

TABLE 1-continued

|  | Nrp1$_{b1b2}$ | Nrp1$_{a2b1b2}$ | Nrp1$_{b1}$/Fab | Nrp2$_{b1b2}$ | Nrp2$_{a2b1b2}$ | Nrp2$_{a1a2b1b2}$/Fab | Nrp2$_{a1a2b1b2}$/Fab |
|---|---|---|---|---|---|---|---|
| No. Atoms |  |  |  |  |  |  |  |
| Protein | 2,552 | 3,480 | 4,540 | 2,495 | 6,768 | 7,568 | 7,681 |
| Ligand/ion | 6 | 101 | 8 | 6 | 2 | 28 | 0 |
| Water | 267 | 187 | 234 | 234 | 233 | 0 | 0 |
| B-factors (Å$^2$) | 27.3 | 35.9 | 39.4 | 25.8 | 18.3 | 89.6 | 111 |
| R.m.s deviations |  |  |  |  |  |  |  |
| Bond lengths (Å) | 0.012 | 0.012 | 0.011 | 0.011 | 0.012 | 0.010 | 0.008 |
| Bond angles (°) | 1.5 | 1.5 | 1.3 | 1.3 | 1.4 | 1.2 | 1.2 |

TABLE S1

|  | Nrp Residue Range | Final Conc. (mg/mL) | Protein Buffer | Crystallization Buffer | Cryoprotectant |
|---|---|---|---|---|---|
| Nrp1$_{b1b2}$ | Phe$^{273}$-Glu$^{586}$ | 15 | 10 mM Tris-HCl (pH 7.5) 50 mM NaCl | 20% PEG 3,350 0.2M Sodium Fluoride | Well solution + 20% glycerol |
| Nrp1$_{a2b1b2}$ | Phe$^{141}$-Glu$^{586}$ | 11 | 10 mM Tris-HCl (pH 7.5) 50 mM NaCl | 0.1M MES (pH 6.5) 12% PEG 20,000 | Well solution + 20% ethylene glycol |
| Nrp1$_{b1}$/Fab (anti-Nrp1$^B$) | Phe$^{273}$-Thr$^{427}$ | 15 | 10 mM Hepes (pH 7.2) 100 mM NaCl | 25% PEG 1,500 4% tert-butanol | 10 mM Hepes (pH 7.2) 25% PEG 1,500 10% ethylene glycol |
| Nrp2$_{b1b2}$ | Phe$^{275}$-Thr$^{595}$ | 12 | 25 mM Tris-HCl (pH 7.5) 150 mM NaCl | 0.1M Bis-Tris (pH 6.5) 20% PEG 5,000 MME | Well solution + 20% glycerol |
| Nrp2$_{a2b1b2}$ | Gly$^{145}$-Thr$^{595}$ | 15 | 20 mM Tris-HCl (pH 7.5) 300 mM NaCl 1 mM CaCl$_2$ | 0.1M Hepes (pH 7.5) 10% PEG 8,000 | Well solution + 20% ethylene glycol |
| Nrp2$_{a1a2b1b2}$/Fab (anti-panNrp$^A$) Monoclinic form | Met$^1$-Thr$^{595}$ | 13 | 25 mM Tris-HCl (pH 7.5) 200 mM NaCl | 0.1M Hepes (pH 7.5) 22% polyacrylic acid 5100 0.02M MgCl$_2$ | Well solution + 20% glycerol |
| Nrp2$_{a1a2b1b2}$/Fab (anti-panNrp$^A$) Trigonal form | Met$^1$-Thr$^{595}$ | 13 | 25 mM Tris-HCl (pH 7.5) 200 mM NaCl | 10% PEG 1,000 10% PEG 8,000 | Well solution + 20% glycerol |

What is claimed:

1. An anti-pan Neurophilin$^A$ (anti-panNrp$^A$) antibody, or an antigen binding fragment thereof, comprising:
    (a) a light chain variable domain sequence of SEQ ID NO: 4 or SEQ ID NO: 5 and/or a heavy chain variable domain sequence of SEQ ID NO: 7, or
    (b) the CDRL1 sequence of SEQ ID NO: 28, the CDRL2 sequence of SEQ ID NO: 30, and the CDRL3 sequence of SEQ ID NO:32 or 33 and/or the CDRH1 sequence of SEQ ID NO: 35, the CDRH2 sequence of SEQ ID NO: 37, and the CDRH3 sequence of SEQ ID NO: 39.

2. The anti-panNrp$^A$ antibody or antigen binding fragment of claim 1, comprising the CDRL1 sequence of SEQ ID NO: 28, the CDRL2 sequence of SEQ ID NO: 30, and the CDRL3 sequence of SEQ ID NO: 32 or 33 and the CDRH1 sequence of SEQ ID NO: 35, the CDRH2 sequence of SEQ ID NO: 37, and the CDRH3 sequence of SEQ ID NO: 39.

3. The anti-panNrp$^A$ antibody or antigen binding fragment of claim 1, comprising the light chain variable domain sequence of SEQ ID NO: 4 or SEQ ID NO: 5 and the heavy chain variable domain sequence of SEQ ID NO: 7.

4. The anti-panNrp$^A$ of claim 1, or antigen binding fragment thereof, comprising the sequence shown in FIG. 9A (SEQ ID NO: 9).

5. The anti-panNrp$^A$ antibody of claim 4, wherein the antigen binding fragment is selected from the group consisting of Fab, Fab', F(ab')$_2$, scFv, (scFv)$_2$, linear antibody, single-chain antibody molecule, minibody, diabody, and multispecific antibody formed from antibody fragments.

6. The anti-panNrp$^A$ antibody of claim 5, wherein the antigen binding fragment is a Fab fragment.

7. The anti-panNrp$^A$ of claim 1, or antigen binding fragment thereof, comprising the sequence shown in FIG. 9B (SEQ ID NO: 10).

8. The anti-panNrp$^A$ antibody of claim 7, wherein the antigen binding fragment is selected from the group consisting of Fab, Fab', F(ab')$_2$, scFv, (scFv)$_2$, linear antibody, single-chain antibody molecule, minibody, diabody, and multispecific antibody formed from antibody fragments.

9. The anti-panNrp$^A$ antibody of claim 8, wherein the antigen binding fragment is a Fab fragment.

10. The anti-panNrp$^A$ antibody of claim 1 that binds to both Nrp1 and Nrp2.

11. The anti-panNrp$^A$ antibody of claim 10 having a binding affinity of at least about 0.10 nM for both Nrp1 and Nrp2.

12. The anti-panNrp$^A$ antibody of claim 10 having a binding affinity of at least about 0.15 nM for both Nrp 1 and Nrp2.

13. The anti-panNrp$^A$ antibody of claim 10 having a binding affinity of at least about 0.20 nM for both Nrp1 and Nrp2.

14. The anti-panNrp$^A$ antibody of claim 10 having a binding affinity of at least about 0.25 nM for both Nrp1 and Nrp2.

15. The anti-panNrp$^A$ antibody of claim 10 having a binding affinity of at least about 0.30 nM for both Nrp1 and Nrp2.

16. The anti-panNrp$^A$ antibody of claim 1 which is capable of blocking Sema3 binding to both Nrp1 and Nrp2.

17. The anti-panNrp$^A$ antibody of claim 1 that does not block VEGF binding to Nrp1 or Nrp2.

18. The anti-panNrp$^A$ antibody of claim 16 or claim 17 which is capable of inhibiting semaphorin biological activity in vitro.

19. The anti-panNrp$^A$ antibody of claim 16 or claim 17 which is capable of inhibiting semaphorin biological activity in vivo.

* * * * *